US010446259B2

(12) United States Patent
Pirhaji et al.

(10) Patent No.: US 10,446,259 B2
(45) Date of Patent: Oct. 15, 2019

(54) SYSTEMS, APPARATUS, AND METHODS FOR ANALYZING AND PREDICTING CELLULAR PATHWAYS

(71) Applicant: Massachusetts Institute of Technology, Cambridge, MA (US)

(72) Inventors: Leila Pirhaji, Cambridge, MA (US); Ernest Fraenkel, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 443 days.

(21) Appl. No.: 15/233,246

(22) Filed: Aug. 10, 2016

(65) Prior Publication Data

US 2017/0046476 A1 Feb. 16, 2017

Related U.S. Application Data

(60) Provisional application No. 62/203,292, filed on Aug. 10, 2015, provisional application No. 62/368,715, filed on Jul. 29, 2016.

(51) Int. Cl.
| | |
|---|---|
| *G16B 5/00* | (2019.01) |
| *G16B 20/00* | (2019.01) |
| *G01N 33/50* | (2006.01) |
| *G01N 33/68* | (2006.01) |
| *G06F 19/10* | (2011.01) |

(52) U.S. Cl.
CPC ............ *G16B 5/00* (2019.02); *G01N 33/5038* (2013.01); *G01N 33/6848* (2013.01); *G01N 33/6896* (2013.01); *G16B 20/00* (2019.02); *G01N 2800/2835* (2013.01)

(58) Field of Classification Search
None
See application file for complete search history.

(56) References Cited

U.S. PATENT DOCUMENTS

| | | | |
|---|---|---|---|
| 8,612,160 B2 | 12/2013 | Fraenkel et al. | |
| 2008/0097939 A1 | 4/2008 | Guyon et al. | |
| 2010/0250143 A1 | 9/2010 | Fraenkel et al. | |
| 2011/0173189 A1 | 7/2011 | Singh et al. | |
| 2012/0185227 A1 | 7/2012 | Nikolskaya et al. | |

FOREIGN PATENT DOCUMENTS

| | | |
|---|---|---|
| EP | 2577535 | 10/2014 |
| WO | 2011153372 A2 | 12/2011 |

OTHER PUBLICATIONS

Razick et al. BMC Bioinformatics (9)(1):405 (2008).*
Hecker et al. (Biosystems vol. 96(1):86-103 (2009).*
Rolland et al. in Cell vol. 159:1212-1226 (2014).*
Barabasi et al. in Nature Reviews: Genetics vol. 12:56-68 (2011).*
Huang (A Constraint Optimization Framework for Discovery of Cellular Signaling and Regulatory Networks; Mass. Institute of Tech. PhD Thesis (2011).*
Beger et al., "Metabolomics enables precision medicine: A White Paper, Community Perspective," Metabolomics, 12:149, (2016), 15 pages.
Cai et al., "Network marker selection for untargeted LC-MS metabolomics data," Journal of Proteome Research, vol. 16, pp. 1261-1269, (2017).
Cho et al., "Integration of untargeted metabolomics with transcriptomics reveals active metabolic pathways," Metabolomics, vol. 11, pp. 503-517, (2015).
Krumsiek, J. et al., "Mining the unknown: a systems approach to metabolite identification combining genetic and metabolic information," PLoS Genetics, vol. 8, Issue 10, (Oct. 2012), 14 pages.
Li, S. et al., "Predicting network activity from high throughput metabolomics," PLoS Computational Biology, vol. 9, Issue 7, (Jul. 2013), 11 pages.
Quell et al., "Automated pathway and reaction prediction facilitates in silico identification of unknown metabolites in human cohort studies," ScienceDirect, Journal of Chromatography B, pp. 1-10, (2017).
Tuncbag et al., "Simultaneous reconstruction of multiple signaling pathways via the prize-collecting Steiner forest problem," Springer Science + Business Media B.V., 46 pages, (Feb. 5, 2013).
International Search Report and Written Opinion in International Application No. PCT/US2016/46289, dated Nov. 2, 2016, 12 pages.
Gosline, et al., "SAMNet: a network-based approach to integrate multi-dimensional high throughput datasets", *Integr. Biol.*, 2012, vol. 4, No. 11, pp. 1415-1427.

(Continued)

*Primary Examiner* — Lori A. Clow
(74) *Attorney, Agent, or Firm* — Smith Baluch LLP

(57) ABSTRACT

Integrative analysis of metabolites is essential to obtain a comprehensive view of dysregulated biological pathways leading to a disease. Despite the great potential of metabolites their system level analysis has been limited. Global measurements of the metabolites by liquid chromatography-mass spectrometry (MS) detects metabolites features changing in a disease. However, identification of each feature is a bottleneck in metabolomics, in which a fraction of them are identified via tandem MS. Consequently, the scarcity of these data add additional barriers to decipher their biological meaning, especially in relation to other 'omic data such as proteomics. To address these challenges, a novel network-based approach called PIUMet is described. PIUMet infers dysregulated pathways and components from the differential metabolite features between control and disease systems without the need for the prior identification. The application of PIUMet is demonstrated by integrative analysis of untargeted lipid profiling data of a cell line model of Huntington's disease. The results show that PIUMet inferred dysregulation of sphingolipid metabolism in the disease cells. Additionally, PIUMet identified disease-modifying metabolite in the pathway that remained undetected experimentally. Furthermore, the lipidomic data of these cell lines was integrated with global phospho-proteomic ones. Integrative analysis of these data using PIUMet was shown to systematically lead to identifying dysregulated proteins in the disease cells that cannot be distinguished with individual analysis of each dataset.

14 Claims, 32 Drawing Sheets

(56) References Cited

OTHER PUBLICATIONS

Pirhajil, et al., "Revealing Disease-Associated Pathways by Netwrok Integration of Untargeted Metabolomics", Nature Methods, Jan. 8, 2016, vol. 13, No. 9, pp. 1-12.
Vidal, et al., " Interactome Networks and Human Disease", Mar. 18, 2011, vol. 144, No. 6, pp. 1-25.
Alfarano et al., "The Biomolecular Interaction Network Database and Related Tools 2005 Update," Nucleic Acids Res. 33(Database issue):D418-424 (2005).
Aranda et al., "PSICQUIC and PSISCORE: Accessing and Scoring Molecular Interactions," Nat. Methods 8:528-529 (2011).
Babnigg et al., "A Database of Unique Protein Sequence Identifiers for Proteome Studies," Proteomics 6 (16):4514-4522 (2006).
Bader et al., "BIND: The Biomolecular Interaction Network Database," Nucleic Acids Res. 31(1):248-250 (2003).
Bailly-Bechet et al., "Inference of Sparse Combinatorial-Control Networks from Gene-Expression Data: A Message Passing Approach," BMC Bioinformatics 11:355 (2010), 12 pages.
Baker et al., "Metabolomics: From Small Molecules to Big Ideas," Nat. Methods 8:117-121 (2011).
Block et al., "Altered Cholesterol and Fatty Acid Metabolism in Huntington Disease," J. Clin. Lipidol. 4:17-23 (2010).
Bornstein et al., "LibSBML: An API Library for SBML," Bioinformatics 24:880-881 (2008).
Brown, "Jurisica I: Online Predicted Human Interaction Database," Bioinformatics 21(9):2076-2082 (2005).
Chatraryamontri et al., "MINT: TThe Molecular INTeraction Database," Nucleic Acids Res. 35(Database issue): D572-574 (2007).
Cho et al., "After the Feature Presentation: Technologies Bridging Untargeted Metabolomics and Biology," Curr. Opin. Biotechnol. 28:143-48 (2014).
DeBerardinis et al., "Cellular Metabolism and Disease: What Do Metabolic Outliers Teach Us?" Cell 148:1132-44 (2012).
Deogracias et al., "Fingolimod, a Sphingosine-1 Phosphate Receptor Modulator, Increases BDNF Levels and Improves Symptoms of a Mouse Model of Rett Syndrome," Proc. Natl. Acad. Sci. 109:14230-35 (2012).
Di Menna et al., "Fingolimod Protects Cultured Cortical Neurons Against Excitotoxic Death," Pharmacol. Res. 67:1-9 (2013).
Di Pardo et al., "FTY720 (Fingolimod) Is a Neuroprotective and Disease Modifying Agent in Cellular and Mouse Models of Huntington Disease," Hum. Mol. Genet. 23:2251-65 (2014).
Dunn et al., "Mass Appeal: Metabolite Identification in Mass Spectrometry-Focused Untargeted Metabolomics," Metabolomics 9:44-66 (2013).
Extended European Search Report in European Application No. 16835817.4 dated Apr. 23, 2019, 10 pages.
Frolkis et al., "SMPDB: The Small Molecule Pathway Database," Nucleic Acids Res. 38, D480-D487 (2010).
Gnad et al., "PHOSIDA 2011: The Posttranslational Modification Database," Nucleic Acids Res. 39:D253-60 (2011).
Grapov et al., "MetaMapR: Pathway Independent Metabolomic Network Analysis Incorporating Unknowns," Bioinformatics 31:2757-60 (2015).
Guldener et al., "MPact: The MIPS Protein Interaction Resource on Yeast," Nucleic Acids Res. 34(Database issue): D436-441 (2006).
Hermjakob et al., "IntAct: An Open Source Molecular Interaction Database," Nucleic Acids Res. 32(Database issue): D452-455 (2004).
Huang et al., "Integrating Proteomic, Transcriptional, and Interactome Data Reveals Hidden Components of Signaling and Regulatory Networks," Sci. Signaling 2:81 (Jul. 28, 2009), available at www.sciencesignaling.org (ra40), 11 pages.
Huang et al., "Linking Proteomic and Transcriptional Data Through the Interactome and Epigenome Reveals a Map of Oncogene-Induced Signaling," PLoS Comput. Biol. 9:2 (Feb. 2013), available at www.ploscompbiol.org (e1002887), 21 pages.
Hucka et al., "SBML Forum. The Systems Biology Markup Language (SBML): A Medium for Representation and Exchange of Biochemical Network Models," Bioinformatics 19:524-31 (2003).
Johnson et al., "Bioinformatics: The Next Frontier of Metabolomics," Anal. Chem. 87:147-156 (2015).
Karnovsky et al., "Metscape 2 Bioinformatics Tool for the Analysis and Visualization of Metabolomics and Gene Expression Data," Bioinformatics 28:373-80 (2012).
Kerrien et al., "IntAct—Open Source Resource for Molecular Interaction Data," Nucleic Acids Res. 35(Database issue): D561-565 (2007).
Khurana et al., "Genome-Scale Networks Link Diverse Neurodegenerative Disease Genes to Alpha-Synuclein Through Distinct Cellular Pathologies" (unpublished) (on file with Applicant), Cell Systems(2017) vol. 4:157-170.
Kreilaus et al., "Brain Cholesterol Synthesis and Metabolism Is Progressively Disturbed in the R6/1 Mouse Model of Huntington's Disease: A Targeted GC-MS/MS Sterol Analysis," J. Huntingtons Dis. 4:305-18 (2015).
Kuo et al., "3Omics: A Web-Based Systems Biology Tool for Analysis, Integration and Visualization of Human Transcriptomic, Proteomic and Metabolomic Data," BMC Syst. Biol. 7:64 (2013), 15 pages.
Li et al., "Huntingtin-Protein Interactions and the Pathogenesis of Huntington's Disease," Trends Genet. 20:146-54 (2004).
Ljubić et al. "An algorithmic framework for the exact solution of the prize-collecting Steiner tree problem." Mathematical programming 105.2-3 (2006): 427-449.
López et al., "Brain Lipogenesis and Regulation of Energy Metabolism," Curr. Opin. Clin. Nutr. Metab. Care 11:483-90 (2008).
Maceyka et al., "Sphingosine-1-phosphate Signaling and Its Role in Disease," Trends Cell Biol. 22:50-60 (2012).
Mishra et al., "Human Protein Reference Database—2006 Update," Nucleic Acids Res. 34(Database issue):D411-414 (2006).
NCBI Resource Coordinators, "Database Resources of the National Center for Biotechnology Information," Nucleic Acids Res. 41:D8-D20 (2013).
Ng et al., "Extensive Changes in DNA Methylation Are Associated with Expression of Mutant Huntingtin," Proc. Natl. Acad. Sci. 110:2354-59 (2013).
Pagel et al., "The MIPS Mammalian Protein-Protein Interaction Database," Bioinformatics 21(6):832-834 (2005).
Patti et al., "Innovation: Metabolomics: The Apogee of the Omics Trilogy," Nat. Rev. Mol. Cell Biol. 13:263-69 (2012).
Peri et al., "Development of Human Protein Reference Database as an Initial Platform for Approaching Systems Biology in Humans," Genome Res. 13(10):2363-2371 (2003).
Puri et al., "Ethyl-EPA in Huntington Disease: A Double-Blind, Randomized, Placebo-Controlled Trial," Neurol. 65:286-92 (2005).
Puri et al., "Reduction in Cerebral Atrophy Associated with Ethyl-eicosapentaenoic Acid Treatment in Patients with Huntington's Disease," J. Int. Med. Res. 36:896-905 (2008).
Ruepp et al., "CORUM: The Comprehensive Resource of Mammalian Protein Complexes," Nucleic Acids Res. 36 (Database issue):D (Jan. 1, 2008), 5 pages.
Saghatelian et al., "Assignment of Endogenous Substrates to Enzymes by Global Metabolite Profiling," Biochem. 43:14332-39 (2004).
Salwinski et al., "The Database of Interacting Proteins: 2004 Update," Nucleic Acids Res. 32(Database issue): D449-451 (2004).
Schreiber et al., "Rapid Detection of Octamer Binding Proteins with 'Mini-Extracts,' Prepared from a Small Number of Cells," Nucleic Acids Res. 17:6419 (1989), 1 page.
Stark et al., "BioGRID: A General Repository for Interaction Datasets," Nucleic Acids Res. 34(Database issue): D535-539 (2006).
Stevnsner et al., "The Role of Cockayne Syndrome Group B (CSB) Protein in Base Excision Repair and Aging," Mech. Ageing Dev. 129:441-48 (2008).
Subba Rao, "Mechanisms of Disease: DNA Repair Defects and Neurological Disease," Nat. Clin. Pract. Neurol. 3:162-72 (2007).
Tautenhahn et al., "XCMS Online: A Web-Based Platform to Process Untargeted Metabolomic Data," Anal. Chem. 84:5035-39 (2012).
Thiele et al., "A Community-Driven Global Reconstruction of Human Metabolism," Nat. Biotechnol. 31:419-25 (2013).

(56) References Cited

OTHER PUBLICATIONS

Trettel et al., "Dominant Phenotypes Produced by the Huntington's Disease Mutation in STHdh(Q111) Striatal Cells," Hum. Mol. Genet. 9:2799-809 (2000).
Valenza et al., "Emerging Roles for Cholesterol in Huntington's Disease," Trends Neurosci. 34:474-86 (2011).
Wishart et al., "HMDB 3.0—The Human Metabolome Database in 2013," Nucleic Acids Res. 41(D1):D801-7 (Jan. 2013).
Yeger-Lotem, et al., "Bridging High-Throughput Genetic and Transcriptional Data Reveals Cellular Responses to Alpha-Synuclein Toxicity," Nat. Genet. 41:316-23 (2009).
Yehuda et al., "Essential Fatty Acids and the Brain: From Infancy to Aging," Neurobiol. Aging 26(Suppl. 1):98-102 (2005).

\* cited by examiner

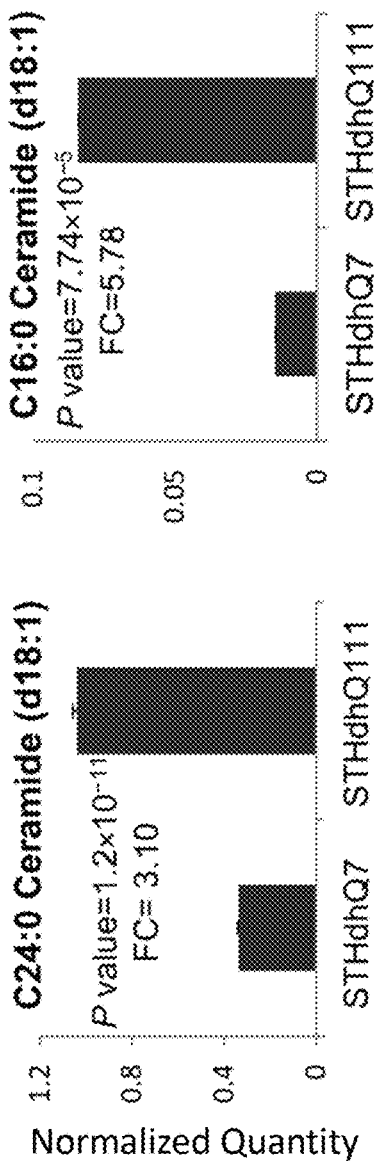
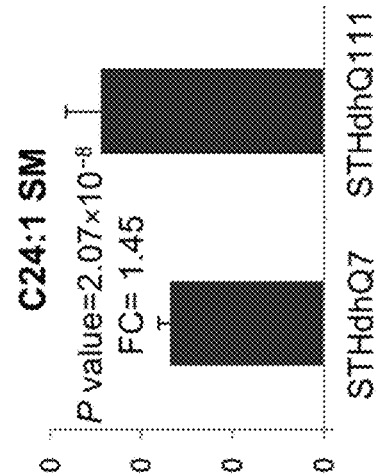
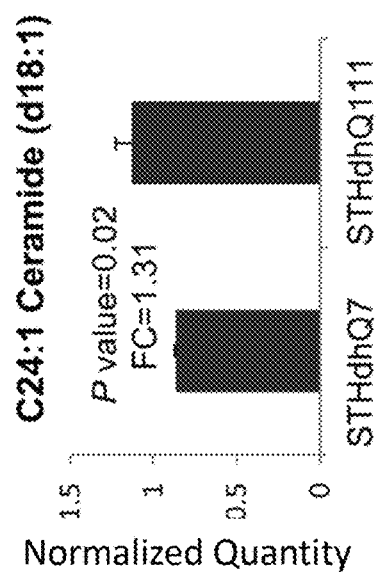
FIG. 15A
FIG. 15B
FIG. 15C
FIG. 15D

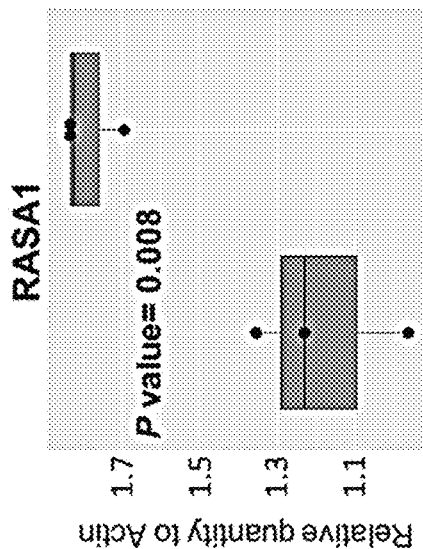
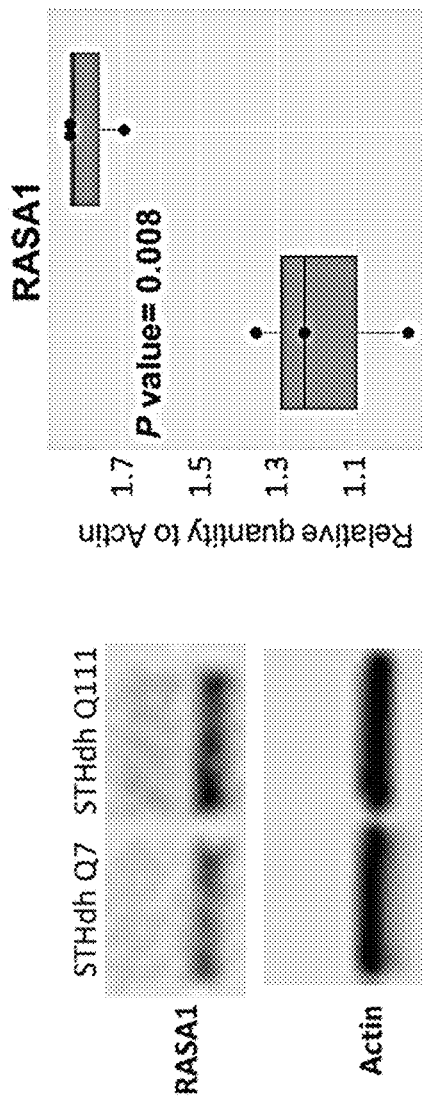
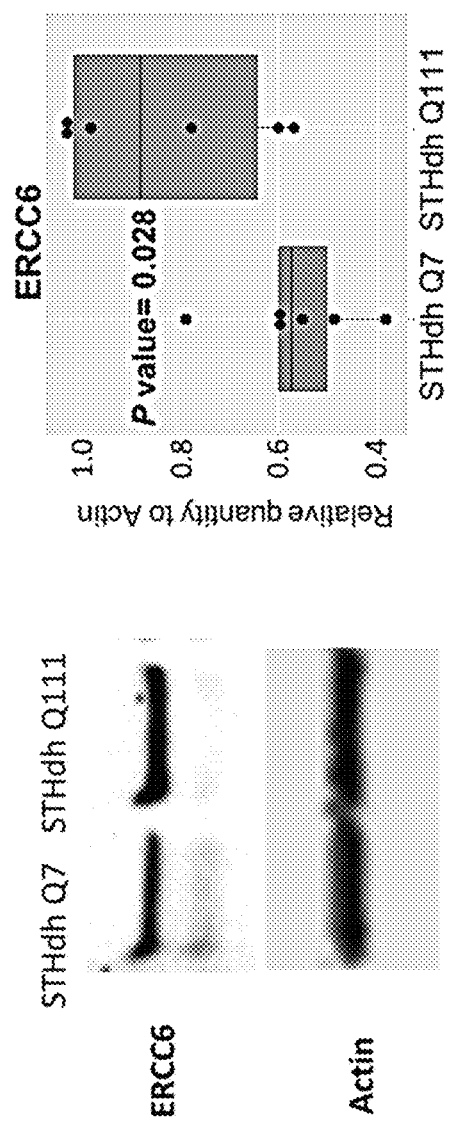

SYSTEMS, APPARATUS, AND METHODS FOR ANALYZING AND PREDICTING CELLULAR PATHWAYS

CROSS-REFERENCE TO RELATED APPLICATIONS

This application claims priority to and the benefit of U.S. Provisional Application No. 62/203,292, entitled, "Systems, Apparatus, and Methods for Analyzing and Predicting Cellular Pathways," filed Aug. 10, 2015, and U.S. Provisional Application No. 62/368,715, entitled, "Systems, Apparatus, and Methods for Analyzing and Predicting Cellular Pathways," filed Jul. 29, 2016, both of which applications are incorporated herein by reference in their entirety.

GOVERNMENT SUPPORT

This invention was made with Government support under Grant Nos. R01-GM089903, U54-NS091046, and U01-CA184898, each of which was awarded by the National Institutes of Health; and Grant Nos. U54-CA112967 and P30-CA014051, each of which was awarded by the National Cancer Institute. The Government has certain rights in the invention.

TECHNICAL FIELD

The present disclosure relates generally to systems, apparatus, and methods for analyzing cellular biology. More specifically, the present disclosure relates to systems, apparatus, and methods for integrating, analyzing, and/or predicting proteomic, transcriptomic, metabolomic, phenomic, genomic, and/or other cellular biology information, including various high throughput experimental data.

BACKGROUND

Various high-throughput experiments may be used to measure alterations in DNA, RNA, protein, and metabolite levels between disease and control systems. In order to understand the pathogenesis of a disease, analysis and prediction of one or more underlying mechanisms causing and/or linking changes in various classes of molecules may be helpful for understanding, preventing, and/or treating disease.

Metabolomics, the study of chemical processes involving metabolites, represents one important aspect of cellular function. A metabolome represents the collection of all metabolites, which are the end products of cellular processes, in a biological cell, tissue, organ, or organism. Untargeted metabolomics involves measuring relative levels of metabolite features between disease and control systems. For example, untargeted metabolomics may include affinity purification of metabolites then using liquid chromatography-mass spectrometry (LC-MS), an analytical chemistry technique that combines the physical separation capabilities of liquid chromatography (LC) with the mass analysis capabilities of mass spectrometry (MS).

SUMMARY

The development of effective therapeutic approaches may be facilitated by a system-level understanding of the molecules altered in a disease, as well as complex interactions among them. Among various classes of molecules, metabolites are small, downstream products of genes, mRNA, and proteins. Consequently, metabolite levels more directly reflect the functional status of the cells. Metabolites may be considered chemical fingerprints left by specific cellular processes that correlate well with cellular phenotypes. A "metabolome" is used herein to refer to a collection of all metabolites in a biological cell, tissue, organ, or organism. Because global metabolite measurements reflect disease-associated cellular biochemical activities that are not detected by transcriptional analysis or other "omic" experiments, integrative analysis of metabolomics with other omic data is a crucial step to identifying disease etiology.

However, despite the great potential of metabolites, their system level analysis has been limited due to difficulty in global measurements of metabolites and deciphering their relation to other molecular data. Unbiased identification and quantification of metabolites in cellular systems is one of the challenges associated with global metabolomic studies. Global measurements of metabolites or untargeted metabolomics are performed by affinity purification of metabolites using liquid chromatography-mass spectrometry (LC-MS), which detects thousands of metabolite "peaks" or "features," defined by a unique combination of mass-to-charge ratio m/z and retention time RT. However, LC-MS experiments measure relative levels of metabolite features, and despite the high mass accuracy of modern instruments, several metabolites can match one peak. The inventors have recognized and appreciated that LC-MS is not conducive for high-throughput screening. For further untargeted metabolomic profiling, tandem mass spectrometry (MS/MS) is used to perform fragmentation of differential metabolite peaks between disease and control systems. Despite being expensive and time-consuming, MS/MS experiments characterize relatively few features, and the majority of features remain unknown. Spectral libraries obtained via MS/MS must be interpreted and mapped to various databases to identify any metabolites. If a metabolite is identified, additional pathway enrichment analysis may be needed to infer which metabolomic pathways were disturbed; however, the mechanisms causing these changes are not provided.

Current approaches for analyzing metabolomic data including network and pathway tools rely on the metabolite features that have been further characterized via MS/MS. A first step toward analyzing uncharacterized metabolite features involved inferring potential identities of metabolite features using a Gaussian graphical model that leverages genomics; however, that approach only applies to large sets of samples with genomic data. The Mummichog algorithm uses metabolic networks to resolve some unknown metabolite features but fails to link the data to other system-level molecular information. Thus, the sparsity of identified metabolites remains a major obstacle to interpretation of metabolomic data.

According to some embodiments, systems, apparatus, and methods described herein are based on a novel systems biology approach for more efficiently analyzing untargeted metabolomic data. The systems, apparatus, and methods described herein reduce the need for additional experiments for metabolic identification, and also may be used to predict, through integration with other biological data (e.g., various high-throughput experimental data like metabolomic reactions and protein-protein interaction data), one or more high probability networks that represent cellular mechanisms or pathways that are or should be activated to prevent or treat disease. For example, a network-based approach to integrate data regarding the presence and/or absence of metabolites) with known protein-protein, protein-metabolite, protein-drug interactions, etc., may be used to unbiasedly identify proteins, genotypes, phenotypes, drugs, etc., that alter a level of a metabolite in a disease model, enable applications in targeted drug discovery, and/or repurpose existing drugs.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Other systems, processes, and features will become apparent to those skilled in the art upon examination of the following drawings and detailed description. It is intended that all such additional systems, processes, and features be included within this description, be within the scope of the present invention, and be protected by the accompanying claims.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIGS. 15A-15D are bar plots comparing altered sphingolipids in STHdh Q111 cells to STHdh Q7 cells in accordance with some embodiments.

FIGS. 24A and 24C are series of images comparing altered Western blot results in STHdh Q111 cells to STHdh Q7 cells in accordance with some embodiments, and FIGS. 24B and 24D are bar plots comparing protein levels in STHdh Q111 cells to STHdh Q7 cells in accordance with some embodiments.

FIG. 26A plots degree distribution of all phospho-proteins in a PPMI network, and FIG. 26B plots degree distribution of differential phospho-proteins between wild-type and mutated STHdh cell lines.

DETAILED DESCRIPTION

The present disclosure relates to systems, apparatus, and methods for integrating, analyzing, and/or predicting proteomic, transcriptomic, metabolomic, phenomic, genomic, and/or other cellular biology information, including various high throughput experimental data.

Figure 1:
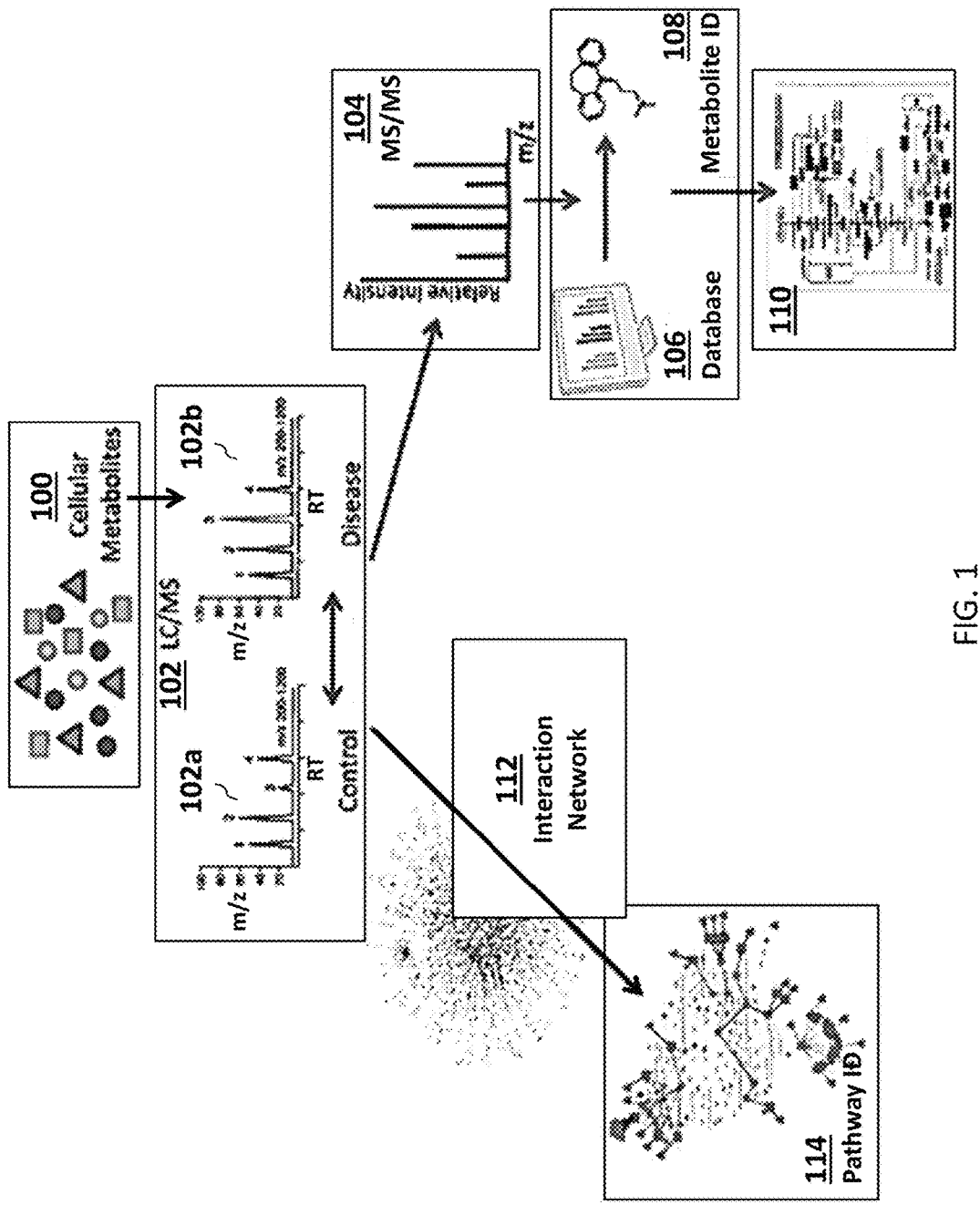
FIG. 1 is a flow diagram comparing a typical approach for analyzing untargeted metabolomics to an approach utilized in accordance with some embodiments.

FIG. 1 is a flow diagram comparing a typical approach for analyzing untargeted metabolomics to an approach utilized by systems, apparatus, and methods described herein according to some embodiments. For example, in FIG. 1, control samples and disease samples of cellular metabolites are obtained 100. In step 102, relative levels of metabolite features between the control samples and the disease samples are determined using affinity purification of metabolites and liquid chromatography-mass spectrometry (LC-MS) experiments. In plot 102a of mass-to-charge intensity m/z and retention time RT, the four elative peaks indicate at least four different metabolites (i.e., each peak may match multiple metabolites) in the control samples. In plot 102b of mass-to-charge intensity m/z and retention time RT, the four relative peaks indicate at least four different metabolites (i.e., each peak may match multiple metabolites) in the disease samples.

Under the typical approach, tandem mass spectrometry (MS/MS) 104 is performed to differentiate the peaks identified in the control samples from the peaks identified in the disease samples. In step 106, one or more resulting spectral libraries are interpreted and mapped to one or more databases to attempt to identify the metabolites 108 associated with the peaks of interest. After metabolite identification is attempted 108, additional pathway enrichment analysis 110 may be used to infer disturbed metabolomic pathways; however, these results do not provide the actual cellular mechanisms or interactions causing these changes between the control samples and the disease samples.

Under the novel systems biology approach described herein, known or existing biological data, such as metabolomics reactions and protein-protein interaction data, is integrated into a network. For example, in FIG. 1, network 112 may be formed from existing biological data regarding, for example, protein-protein interactions and protein-metabolite interactions, and used to identify or predict one or more high probability biological response pathways that represent cellular mechanisms. In some embodiments, systems, apparatus, and methods described herein include identifying a mechanism associated with a cellular response by identifying molecules participating in the cellular response, such as in step 102 in FIG. 1; accessing a network representing information characterizing molecular interactions, such as network 112 in FIG. 1; and determining pathways connecting the identified molecules participating in the cellular response, such as in step 114 of FIG. 1.

Creation of Interaction and/or Association Networks

To overcome challenges in integrative analysis of untargeted metabolomics, an interaction and/or association network may be created to predict one or more high probability pathways that represent cellular mechanisms.

A variety of different types of molecules participating in a cellular mechanism or response may be identified. Among these are proteins, mRNAs, DNA sequences, and protein-protein complexes. For example, one or more proteins participating in a cellular response may include one or more phosphorylated proteins, one or more proteins encoded by a gene that, when deleted, causes a change in an organism's phenotype, and/or one or more proteins that are present in an amount that changes during the cellular response. In some embodiments, the cellular response is a signaling event and the destination node represents a target gene of the signaling event. In other embodiments, the cellular response is a metabolic event and the destination node represents a target metabolite of the metabolic event.

Figure 2:
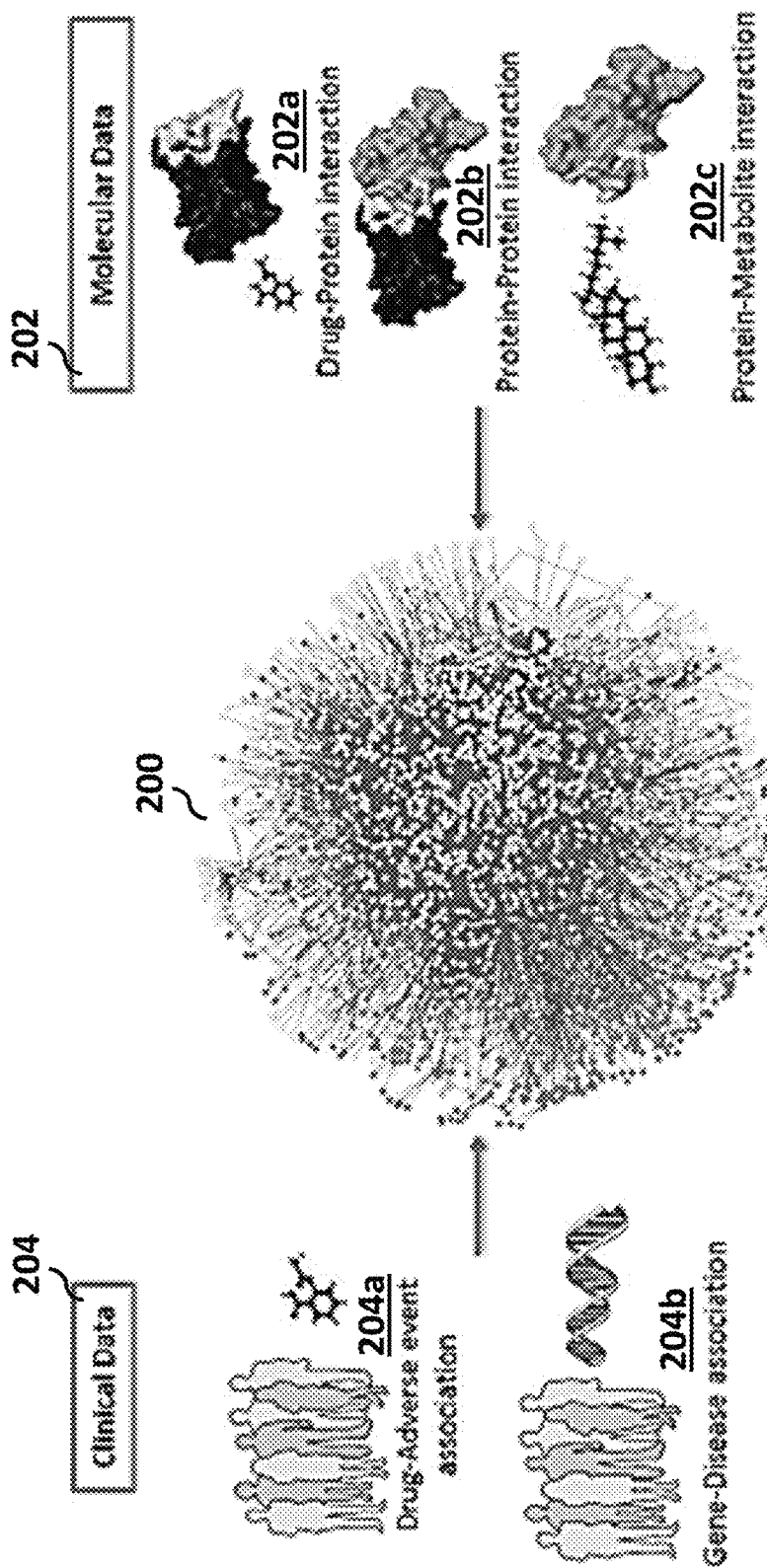
FIG. 2 is a diagram illustrating integration of data from different sources to form an interaction and/or association network in accordance with some embodiments.

FIG. 2 is a diagram illustrating integration of data from different sources to form an interaction and/or association network in accordance with some embodiments. Data may be sourced from known or existing data (e.g., various databases, including databases identified herein) and/or supplemented with experimental data. In FIG. 2, network 200 may be created from molecular data 202 and/or clinical data 204. Molecular data 202 may include, but is not limited to, data about one or more drug-protein interactions 202a, one or more protein-protein interactions 202b, and/or one or more protein-metabolite interactions 202c. Clinical data 204 may include, but is not limited to, data about one or more drug-disease associations, one or more drug-adverse event associations 204a, and/or one or more gene-disease associations 204b.

Some specific examples of source databases are listed below in TABLE 1. For example, source database "iRefIndex 13 PPI Network" (iRefIndex) maintains 181,499 interactions between 17,457 proteins; however, at least prior to later versions, iRefIndex failed to provide any metabolite information. By integrating iRefIndex with, for example, "The Union MPPI Network" (Union MPPI), at least 24,506 new metabolite nodes and at least five times as many interactions or edges are available.

TABLE 1

| Source Database | No. of Nodes (N) | No. of Proteins (P) | No. of Metabolites (M) | No. of Edges (E) |
|---|---|---|---|---|
| iRefIndex 13 PPI Network (available online from irefindex.org) | 17,457 | 17,457 | 0 | 181,499 |

TABLE 1-continued

| Source Database | No. of Nodes (N) | No. of Proteins (P) | No. of Metabolites (M) | No. of Edges (E) |
|---|---|---|---|---|
| HMDB 3.5 MPI Network (available online from www.hmdb.ca) | 26,670 | 5,008 | 21,662 | 843,547 |
| Recon 2 MPI Network (available online from vmh.uni.lu) | 5,157 | 1,660 | 3,448 | 20,402 |
| The Union MPPI Network (available online from mips.helmholtz-muenchen.de/proj/ppi) | 42,550 | 18,044 | 24,506 | 1,042,151 |

In some embodiments, network data is represented as an interactome including nodes and edges. Nodes may represent molecules, and edges may connect pairs of nodes to represent an interaction and/or association between the molecules represented by the nodes.

According to some embodiments, a network pathway (e.g., a signaling pathway) may include two or more nodes, each node representing a molecule, and one or more edges, each edge connecting a respective pair of nodes and representing an interaction between the molecules represented by the respective pair of nodes. A subset of nodes in the network may represent molecules identified as participating in a cellular response.

In some embodiments, one or more nodes are weighted by a penalty value or "node cost." Each node in an interactome may be associated with a node cost. A node cost may represent, for example, an anticipated performance of a molecule associated with the node during a signaling event.

In some embodiments, one or more edges are weighted by a penalty value or "edge cost." Each edge in an interactome may be associated with an edge cost. An edge cost may represent, for example, a reliability of an interaction between molecules connected by the edge.

In some embodiments, biochemical reactions are integrated with physical interactions to form a network (e.g., a bipartite graph) of protein-protein and protein-metabolite interactions (PPMI). A PPMI network may be defined according to the following:

$$PPMI = (P, M, E) \quad (1)$$

where P represents protein nodes, M represents metabolite nodes, and E represents interactome edges. A PPMI network may include two sets each of metabolite and protein nodes. The set of interactome edges may represent physical interactions among proteins as well as enzymatic and transport reactions between metabolites and proteins.

According to some embodiments, a PPMI network has the following features:

$$L = \{l | l \in M \wedge 100 \leq MW_l \leq 1500 \wedge l \in \text{Lipid Superclass}\} \quad (2)$$

where L represents a set of metabolites, such that each metabolite l is an element of metabolite nodes M, has a molecular weight $MW_l$ (e.g., between 100 and 1500), and is an element of a lipid super class;

$$LP = \{l_p | l_p \in N_{MPPI}(L)\} \quad (3)$$

where LP represents a set of associated proteins, such that each associated protein $l_p$ is an element of a network $N_{MPPI}$ based on the set of metabolites L; and $$B_L = LP \cup \{p | p \in P \wedge \text{weighted shortest path length}(p, LP) \leq \varepsilon\} \quad (4)$$

where $B_L$ is a set of proteins that are in the set of associated proteins LP and/or in a set of proteins, such that each protein p is an element of protein nodes P and has a weighted shortest path length (based on the protein p and the set of associated proteins LP) that is less than or equal to a constant ε.

In one embodiment, a PPMI network was constructed by combining interactions obtained from three existing databases and integrating the knowledge of biochemical reactions with the physical interactions among proteins. The integrated databases were represented as a weighted bipartite graph of protein-protein and protein-metabolite interaction, in which metabolites and proteins are represented as nodes and physical interactions between proteins and enzymatic and/or transporter reactions are represented as edges. The edges connect reaction substrates to reaction enzymes and the reaction enzymes to reaction products. In this embodiment, the PPMI network includes over 42,000 nodes connected via over one million edges. The node degree distribution of the network is similar to other biological networks, following power law degree distribution, in which many low degree nodes are connected to each other via highly connected nodes. Further details are described below.

Protein-protein interactions were obtained from iRefIndex version 13 (available from irefindex.org; see Razick et al., "iRefIndex: A Consolidated Protein Interaction Database with Provenance," *BMC Bioinformatics* 9(1):405 (2008)). Metabolite information and biochemical reactions were obtained from the Human Metabolome Database (HMDB) version 3 (available from hmdb.ca; see Wishart et al., "HMDB 3.0—The Human Metabolome Database in 2013," *Nucleic Acids Res.* 41(D1):D801-7 (January 2013)) and the human metabolic reconstruction resource Recon 2 (available from vmh.uni.lu; see Thiele et al., "A Community-Driven Global Reconstruction of Human Metabolism," *Nat. Biotechnol.* 31:419-25 (2013)).

iRefIndex is a unified database of known protein-protein interaction (PPI) databases (now including BIND, BioGRID, CORUM, DIP, HPRD, InnateDB, IntAct, MatrixDB, MINT, MPact, MPIDB and MPPI), from which PPIs redundant among the underlying databases have been removed. In this embodiment, the iRefIndex database was downloaded in the provided PSI-MITAB format. No interactions were filtered based on the source of their inference; instead, a scoring function was used to calculate a confidence score for each interaction. For example, PSISCORE Java API33 and the MIscore algorithm may be used to calculate these scores (see Aranda et al., "PSICQUIC and PSISCORE: Accessing and Scoring Molecular Interactions," *Nat. Methods* 8:528-529 (2011)). The MIscore algorithm considers the number of publications, the type of interaction, and the used experiments to calculate confidence scores for molecular interactions.

HMDB is a comprehensive resource of human metabolites including information for over 40,000 detected and expected metabolites. HMDB also includes the association of transporters and enzymes with metabolites, obtained from KEGG and SMPDB34 pathways. In this embodiment, HMDB was downloaded in XML format. Information about metabolites was then parsed from the XML files using an application program interface (API). For example, the ElementTree XML API module (available from Python Software Foundation, Wilmington, Del.) was used to implement an API for parsing and creating XML data in the Python™ programming language. The parsed metabolite information may include but is not limited to super class, molecular weight, chemical composition, and associated proteins. For example, TABLE 2 below lists metabolite super classes and the number of corresponding metabolites in each class in the HMDB 3.5 databases.

TABLE 2

| Super Classes | No. of Metabolites |
|---|---|
| Lipids | 28235 |
| Nucleosides, Nucleotides, and Analogues | 244 |
| Carbohydrates and Carbohydrate Conjugates | 1093 |
| Aromatic Homomonocyclic Compounds | 1762 |
| Aromatic Heteromonocyclic Compounds | 544 |
| Tannins | 214 |
| Aliphatic Homomonocyclic Compounds | 157 |
| Organophosphorus Compounds | 170 |
| Aromatic Heteropolycyclic Compounds | 3025 |
| Amino Acids, Peptides, and Analogues | 1385 |
| Aliphatic Acyclic Compounds | 882 |
| Aliphatic Heteropolycyclic Compounds | 258 |
| Aliphatic Heteromonocyclic Compounds | 399 |
| Organic Acids and Derivatives | 457 |
| Homogeneous Metal Compounds | 52 |
| Polyketides | 1023 |
| Alkaloids and Derivatives | 166 |
| Lignans and Norlignans | 176 |
| Aromatic Homopolycyclic Compounds | 24 |
| None | 11 |
| Homogeneous Non-metal Compounds | 71 |
| Mixed Metal/Non-metal Compounds | 19 |
| Organic Halides | 21 |
| Aliphatic Homopolycyclic Compounds | 30 |
| Inorganic Compounds | 2 |
| Prenol Lipids | 1 |
| Tannins | 1 |
| Organometallic Compounds | 6 |
| Ahydrolyzable Tannins | 1 |
| Hydrolyzable Tannins | 1 |
| Organic Acids | 1 |

In this embodiment, a network was constructed to represent the links between metabolites and associated enzymes and/or transporters from HMDB. For example, the NetworkX software package (available from Python Software Foundation, Wilmington, Del.) was used to create and manipulate the network.

Recon2 is a comprehensive database of metabolic reactions. In this embodiment, Recon2 was downloaded in Systems Biology Markup Language (SBML) format, which is a standard XML-based format for communicating and storing computational models of biological processes such as metabolic reactions. Information about the database entities such as enzymes, metabolites, and metabolic reactions was then parsed using an API. For example, the LibSBML API module (available from Python Software Foundation, Wilmington, Del.) was used to implement an API for parsing and creating SBML data in the Python™ programming language. In this embodiment, a network representation of metabolic reactions was created.

According to some embodiments, each edge in a PPMI network has a weight indicating the confidence score associated with each interaction. The associated confidence scores with the PPMI edges may be obtained from a source database. For example, Recon2 provides a confidence score of zero to four for each metabolic reaction. A score of zero indicates no supporting data about the confidence, whereas a score of four indicates evidence of biochemical data. However, the scale of the scoring may differ between sources. Thus, in some embodiments, all edge weights are scaled to the same distribution in order to have the same scale of edge weights for the entire PPMI network.

In one embodiment, edges were weighted based on reaction confidence scores from more than one database, but scaled to a PPI confidence score distribution. For this purpose, Recon2 metabolic reactions with a confidence score of four were scaled to the maximum PPI score, and metabolic reactions with confidence scores of 3, 2, and 1 were scaled to the PPI third quartile, median, and second quartile scores, respectively. As there was no confidence score associated with interactions obtained from HMDB, edges based on HMDB were arbitrarily assigned edge weights as the median of the PPI confidence score. The inference of robust results in spite of uncertainties in the PPMI edge weights is addressed further below.

Figure 3:
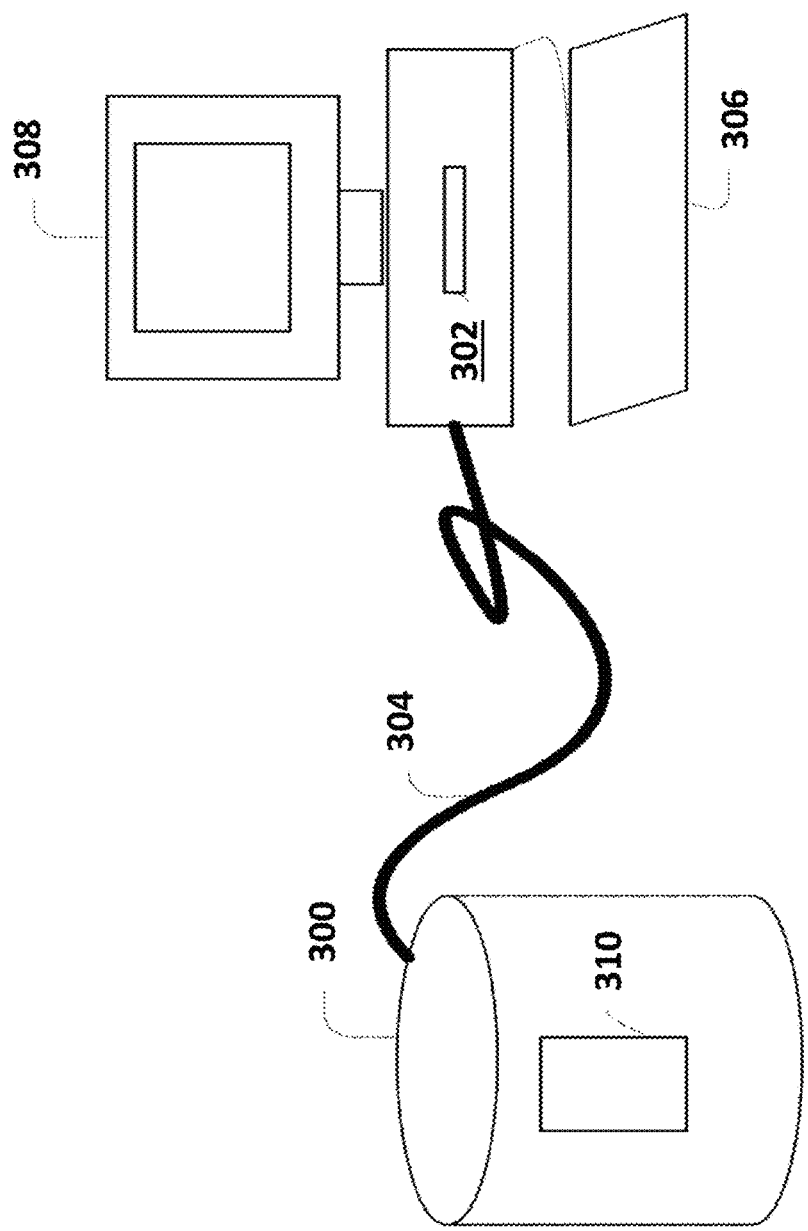
FIG. 3 is a system diagram in accordance with some embodiments.

FIG. 3 is a system diagram in accordance with some embodiments. FIG. 3 shows at least one computer-readable data storage medium 300 (storing, e.g., molecular and/or clinical data) and at least one processing unit 302. The at least one processing unit 302 may be communicatively coupled via at least one communication interface 304 (e.g., wired and/or wireless) to the at least one storage medium 300, at least one input device 306 (e.g., a keyboard), and at least output device 308 (e.g., a monitor). The at least one storage medium 300 may be configured to store information representative of cellular interactions and/or pathways. The at least one input device and the at least one output device may allow for a user to communicate with the system.

In particular, FIG. 3 shows a computer-readable data storage medium 300 tied to a microprocessor 302 via a data communication path 304 according to some embodiments. The data storage medium 300 may store information representative of signaling pathways. An input device 306 in communication with a processing element may provide a way to control the microprocessor 302, and an output device 308 in communication with the microprocessor 302 provides tangible output for inspection, or a pathway for communicating with the data storage medium 300 to which the microprocessor 302 is coupled.

In operation, the microprocessor 302 causes transformations to various electronic components within it, including transistors, diodes and resistors. Ultimately, the microprocessor 302 causes a physically measurable transformation of matter within the data storage medium 300 to which it is tied.

Such software may be tied to a particular computer or to multiple particular computers at one site or distributed across multiple sites and interconnected by a communication network. Accordingly, such software can be deployed at or executed by a particular computer or on multiple particular computers at one site or distributed across multiple sites and interconnected by at least one communication network.

To provide for interaction with a user, the techniques described herein can be implemented on, for example, a computer having a display device, e.g., a cathode ray tube (CRT) or a liquid crystal display (LCD) monitor, for displaying information to the user and a keyboard and a pointing device, e.g., a mouse or a trackball, by which the user can provide input to the computer (e.g., interact with a user interface element by, for example, clicking a button on such a pointing device). Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Some embodiments or components or functions thereof may be distributed over a number of different storage devices, processors, and other components. For example, a web-based interface may be provided to operate a program configured for identifying signaling pathways for cellular events. Data representing the output of some embodiments or components or functions thereof may be communicated, displayed, and/or stored in an electronic format that is computer- and/or human-readable.

Network-Based Optimization Algorithms

In some embodiments, the identification of a mechanism associated with a cellular response includes determining relative levels of molecular features between disease and control samples using affinity purification and LC-MS. However, unlike past approaches, an optimization problem may be defined to determine a subset of the molecules and interactions having a minimum aggregate cost.

In some embodiments, a pathway corresponding to a cellular mechanism and/or response in a network has an aggregate cost based on the aggregation of node and edge costs. In the case of alternative possible pathways, a pathway or a subset of interactions and/or associates may have a minimum aggregate cost. To identify a pathway or a subset of interactions and/or associations with a minimum aggregate cost may involve solving an optimization problem associated with the network.

In some embodiments, a solution to such an optimization problem requires identifying one subset of the originally identified nodes as an input subset containing input nodes and a separate subset of the originally identified nodes as an output subset containing output nodes; identifying a source node representing a source of flow; identifying a destination node representing a destination of flow; and associating a quantity of flow with the source of flow. A pathway may include one or more intermediate nodes between the source node and the destination node. Each node that participates in the cellular response may be assigned a node cost, and each edge may be assigned an edge cost. An objective function for the optimization problem may be formed based on the cost values of the edges connecting the input and output nodes and the quantity of flow traversing these edges from the source node to the destination node. The solution to the optimization problem then may entail identifying at least one sub-network of nodes and edges that minimizes the aggregate cost of the objective function.

Figure 4:
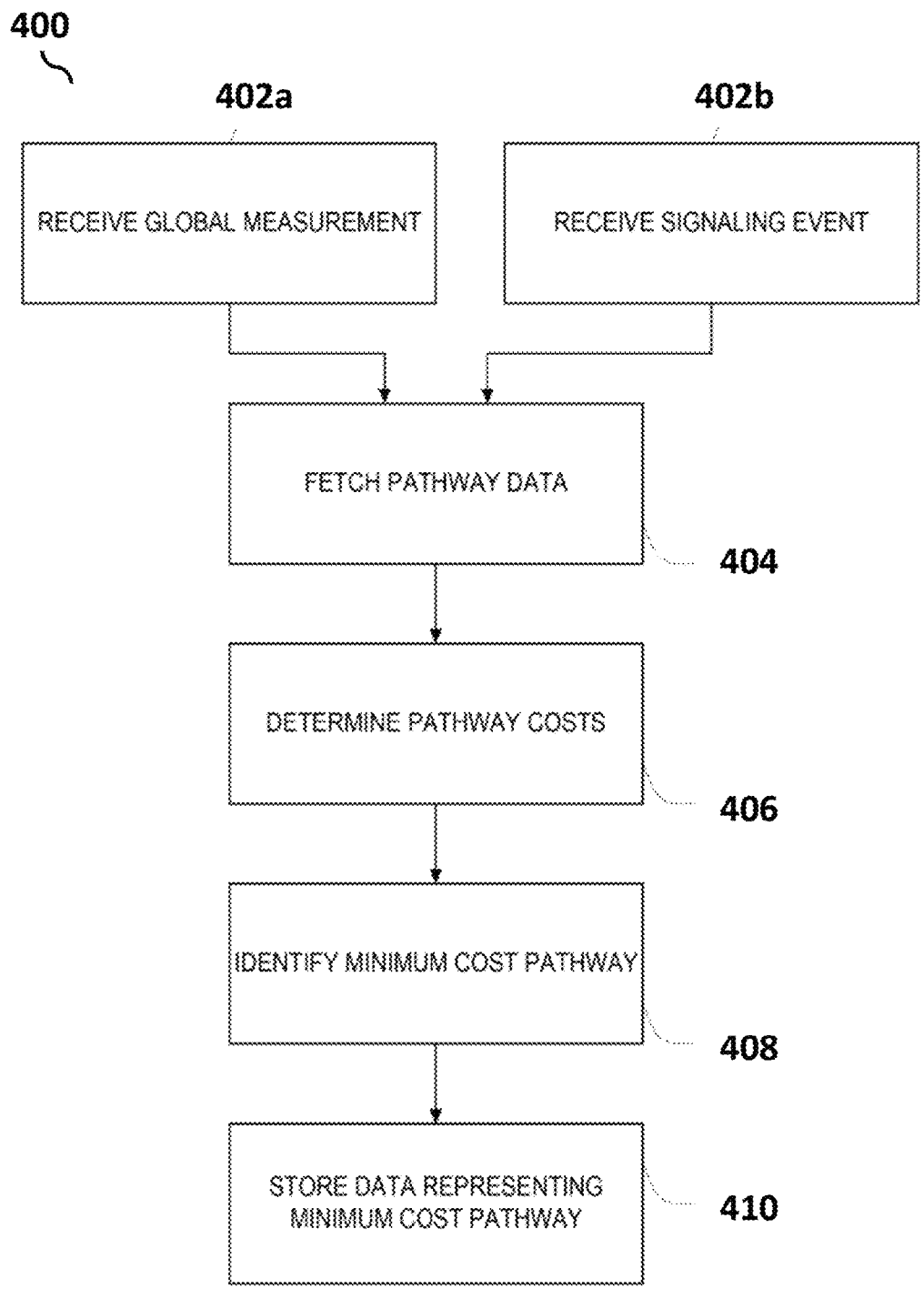
FIG. 4 is a flow diagram illustrating a method for identifying a pathway in accordance with some embodiments.

FIG. 4 is a flow diagram illustrating a method for identifying a pathway in accordance with some embodiments. Method 400 begins with step 402a, in which global measurement data representing activity within a cell is obtained, and/or step 402b, in which a signaling event is obtained. In step 404, pathway data representing the various interactions within the cell is retrieved. The pathway data may or may not be consistent with the global measurement data. In some embodiments, both consistent and inconsistent pathway data is retrieved and/or classified as such after retrieval. In other embodiments, only pathway data that is consistent with global measurement data is retrieved. In step 406, the pathway costs (i.e., the aggregate costs of the individual interactions) are determined. In step 408, the pathway, which may include one or more interactions, with the lowest cost, that is, the minimum aggregate cost is identified. Output representing the minimum cost pathway may be stored in a computer-readable data storage medium in step 410.

Figure 5:
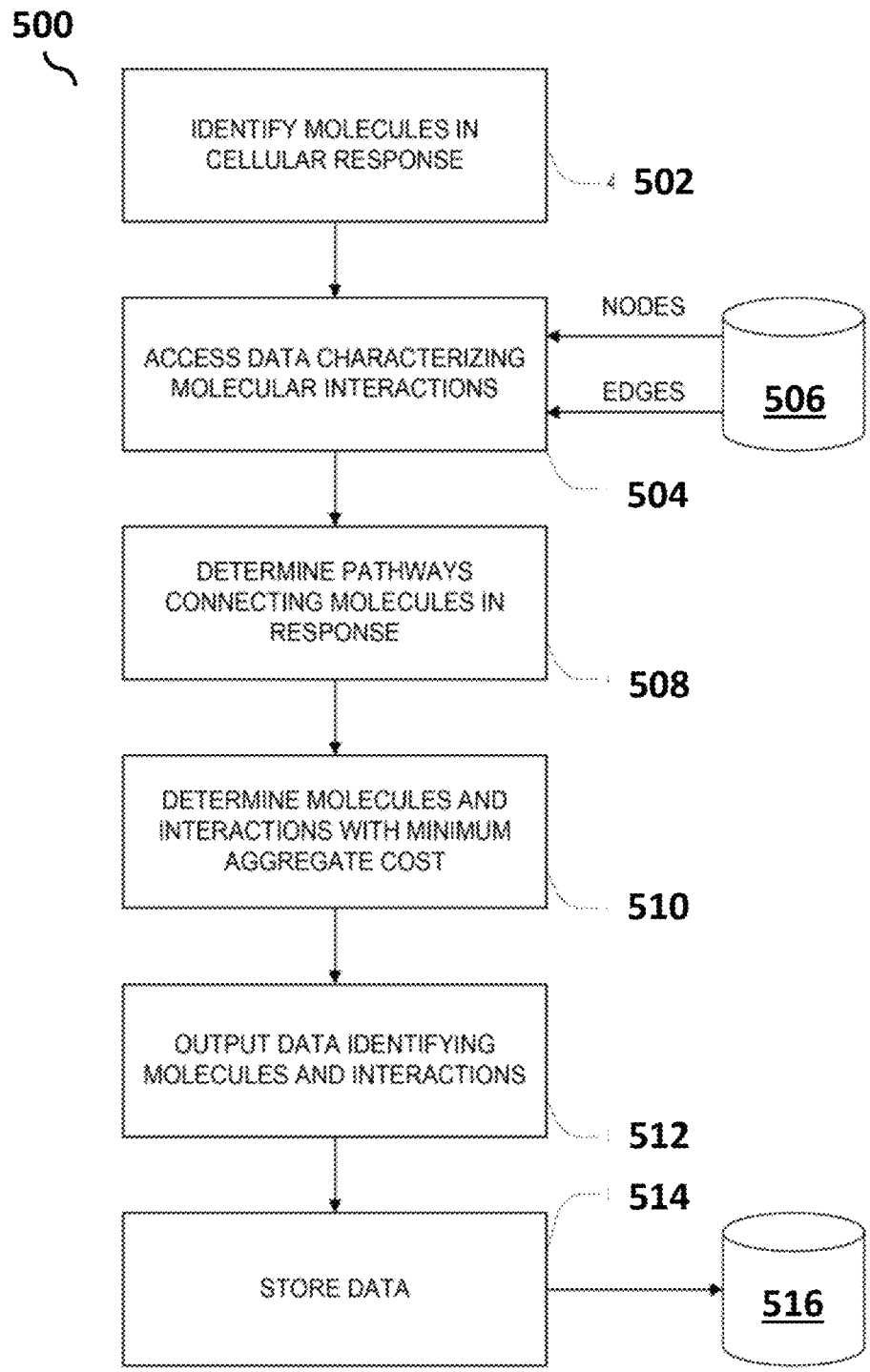
FIG. 5 is a flow diagram illustrating a network-based method for determining molecules and interactions in a cellular response in accordance with some embodiments.

FIG. 5 is a flow diagram illustrating another method for identifying molecules and interactions in accordance with some embodiments. Method 500 begins with step 502, in which molecules that participate in a cellular response are identified. Then, data characterizing interactions between the identified molecules is obtained (e.g., retrieved or created) in step 504. This data may include a network or interactome including a plurality of nodes representing the participating molecules and a plurality of edges connecting the nodes based on their molecular interactions. Weights or cost values associated with an edge represent the extent of interaction between the molecules connected by that edge. Once this data is obtained in step 504, for example, from one or more memory devices 506, a plurality of potential pathways connecting the molecules/nodes in the cellular response are identified in step 508. A subset of the molecules/nodes and the interactions/edges are identified as having a minimum aggregate cost in step 510. Data identifying this subset may be output in step 512 and/or stored in step 514 on one or more memory devices 516, which may or may not include one or more memory devices 506.

In some embodiments, a graph-based approach is used to resolve the ambiguous identity of peaks identified by untargeted metabolomic experiments. These peaks or features are characterized by a unique mass-to-charge ratio m/z and retention time RT. In some embodiments, an algorithm represents these peaks as nodes and connects each peak to the metabolites in a PPMI network with a mass matching the m/z value of the feature, after considering the weight of ionic adducts. The algorithm then may search for subnetworks that are enriched in these metabolites by solving the prize-collecting Steiner forest (PCSF) optimization problem. The networks may be evaluated using randomization strategies to identify results that are robust to choices of parameters.

PCSF optimization identifies an optimum forest (a set of trees) representing simultaneously dysregulated pathways in a disease. This forest is a subnetwork of the PPMI interactome in which experimentally detected dysregulated molecules (terminal set) are linked via undetected molecules (Steiner set); these nodes are connected by known molecular interactions. The optimum subnetwork is inferred by first assigning a prize to each node in the terminal set and costs to the PPMI edges. In addition, to obtain independent simultaneous pathways, an artificial node is connected to the terminal nodes via edges with weight ω. The algorithm then infers a forest solution F, with $N_F$ nodes and $E_F$ edges, by minimizing the following objective function using an established message passing approach:

$$f'(F) = \beta \Sigma_{n \notin N_F} p(n) + \Sigma_{e \in E_F} c(e) + \omega \times k \qquad (5)$$

where p(n) shows the associated prize to each node $n \in N_F$, c(e) shows the cost of each edge $e \in E_F$ in the resultant forest F, and k shows the number of trees in the forest F. Here the terminal nodes' prizes p(n) are equal to −log (P value) of the significance of their alteration in the disease, calculated by two-tailed student's t-test. The costs associated to each edge c(e) are one minus the PPMI edges' weights. Additionally, β is a tuning parameter that controls the size of the resultant forest, which here is considered equal to 4. Weight ω is further a tuning parameter regulating the size of k or the number of trees in the forest solution. To choose a value of ω, the size of the resulting networks and the number of connected terminals may be considered. In one embodiment, different values of ω were considered in the range of 10 to 25, based on the input terminal sets. Smaller values were examined first. Increasing ω results in a larger network that connects more terminals. In some embodiments, the value of ω may be selected to maximize the number of connected terminals. In addition to these parameters, the variable w is an equal and arbitrary weight that may be assigned to edges between disease features and potentially matching metabolites. In one embodiment, w was set equal to 0.99, which is the same as the maximum PPMI edge weight, whereas sensitivity analysis on the value of w resulted in more than 88% robust results (results on file with Applicant).

A prize-collecting Steiner forest algorithm for integrative analysis of untargeted metabolomics (PIUMet) algorithm was developed to address challenges in system-level analysis of metabolomics. According to some embodiments, a PIUMet algorithm adapts the prize-collecting Steiner forest algorithm for integrative analysis of untargeted metabolomics. Untargeted metabolomic experiments generate thousands of metabolite features (or peaks) characterized by an m/z value and a retention time RT. Typically, each feature matches several metabolites with masses in the right range. The raw features that significantly differ between samples and controls using a user-selected statistical test may be the input, at least in part, to a PIUMet algorithm. A PIUMet algorithm may use a machine-learning approach that leverages a database of protein-protein and protein-metabolite interactions to infer a network of dysregulated metabolic pathways. This approach has been demonstrated in the context of uncovering pathways associated with disease, and altered metabolite peaks are referred to disease features. In this context, a PIUMet algorithm output may include disease-associated proteins and/or metabolites.

One or more components of a network, the identity of which were unknown before running a PIUMet algorithm, are referred to herein as "hidden" components. Hidden metabolites directly connected to disease features represent their putative identities, and the remaining hidden metabolites and proteins identified by a PIUMet algorithm are disease-associated proteins and Q2 metabolites that had not been measured directly by experiments. A PIUMet algorithm may perform multi-omic analysis to reveal links between metabolomic dysregulation and other molecules such as proteins. Although some embodiments are directed toward disease-related data, a PIUMet algorithm may be applied to many biological settings.

Figure 6:
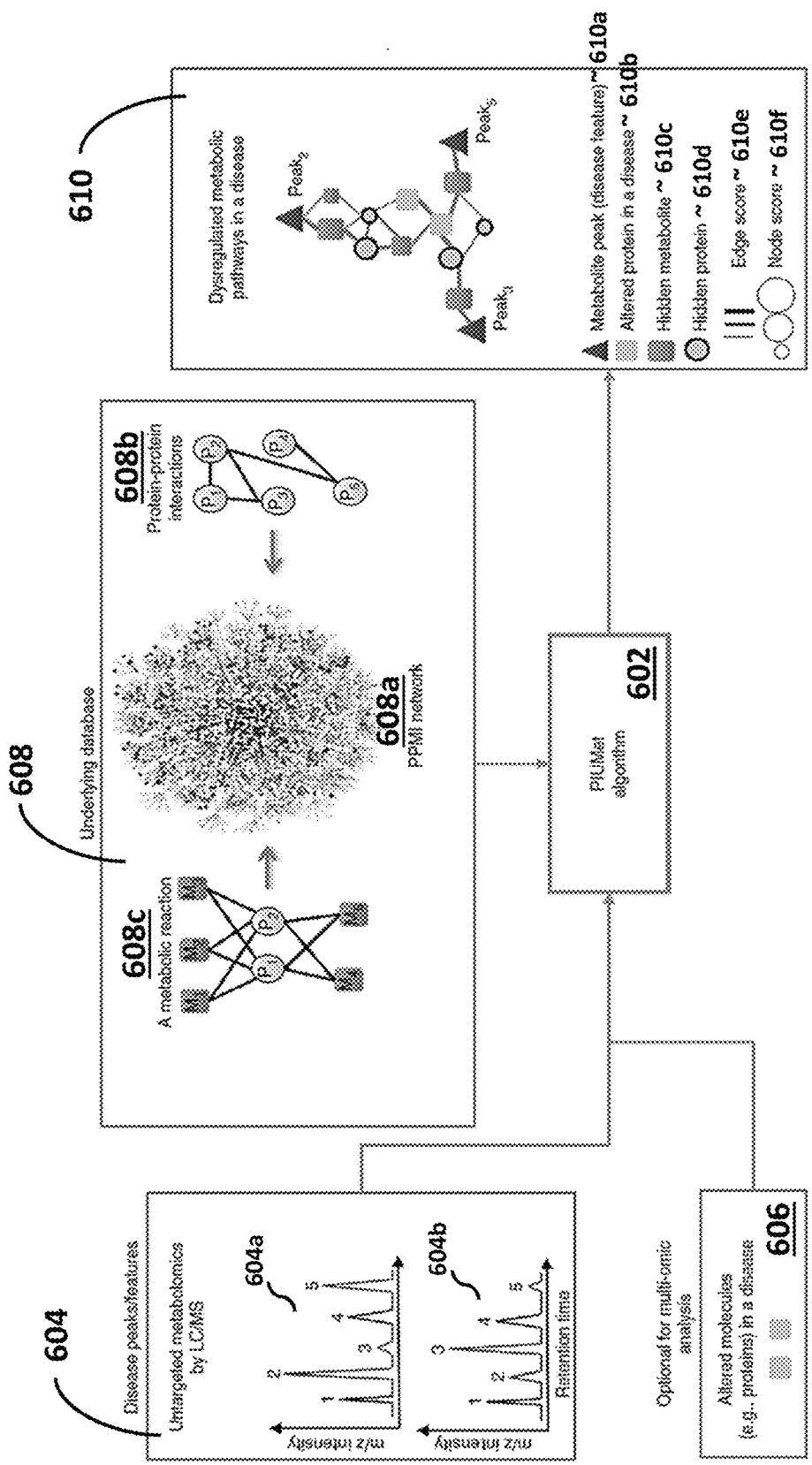
FIG. 6 is a flow diagram illustrating a network-based approach for integrative analysis of untargeted metabolomics in accordance with some embodiments.

FIG. 6 is a flow diagram illustrating a network-based approach for integrative analysis of untargeted metabolomics in accordance with some embodiments. In FIG. 6, machine-learning PIUMet algorithm 602 is used to identify disease-associated pathways and hidden components from untargeted metabolomic data 604. The input to PIUMet algorithm 602 may include metabolomic peaks or features that differ between disease samples 604a and control samples 604b (e.g., differential metabolite peaks 2, 3, and 5 detected by LC/MS in the examples shown). Optionally for multi-omic analysis, PIUMet algorithm 602 also may accept other omic data about altered molecules (e.g., proteomics) as an optional input 606.

PIUMet algorithm 602 then searches underlying database 608. Underlying database 608 may include a PPMI network 608a. PPMI nodes may include proteins (represented as, e.g., circle nodes) and/or metabolites (represented as, e.g., square nodes). These nodes are connected via edges representing physical interactions among proteins 608b (e.g., protein $P_2$ interacts with proteins $P_1$, $P_3$, and $P_5$), as well as substrate-enzyme and product-enzyme associations of metabolic reactions 608c (e.g., metabolite substrates $M_1$, $M_2$, and $M_3$; protein enzymes $P_1$ and $P_2$; and metabolite products $M_4$ and $M_5$).

The output from PIUMet algorithm 602 is an optimum PPMI subnetwork 610 that connects disease peaks or features 610a (e.g., peaks 2, 3, and 5). Subnetwork 610 represents dysregulated metabolic pathways in diseased cells including altered proteins 610b. Components of subnetwork 610 reveal hidden metabolites 610c and hidden proteins 610d that had not been detected in experiments. Hidden metabolites 610c directly connected to disease features 610a represent the putative identity of these features 610a. Additionally, the resulting edges and/or nodes may be assigned edge scores 610e and/or node scores 610f, respectively, based on their robustness to uncertainty in the underlying database 608. Thus, the application of PIUMet algorithm 602 facilitates identification of a metabolite with the highest probability of corresponding to a peak as well as a network pathway regulating the level of that metabolite.

In one embodiment, a PIUMet database (e.g., a PPMI network) includes more than 42,000 nodes connected by over one million edges. The network was built by integrating knowledge of biochemical reactions with curated interactions among proteins taken from three established databases. The result was a weighted graph, in which the nodes represent either metabolites or proteins, and the edges show the interactions between proteins as well as enzymatic and transporter reactions. Each edge has a weight reflecting confidence in the reliability of the interaction.

Figure 7:
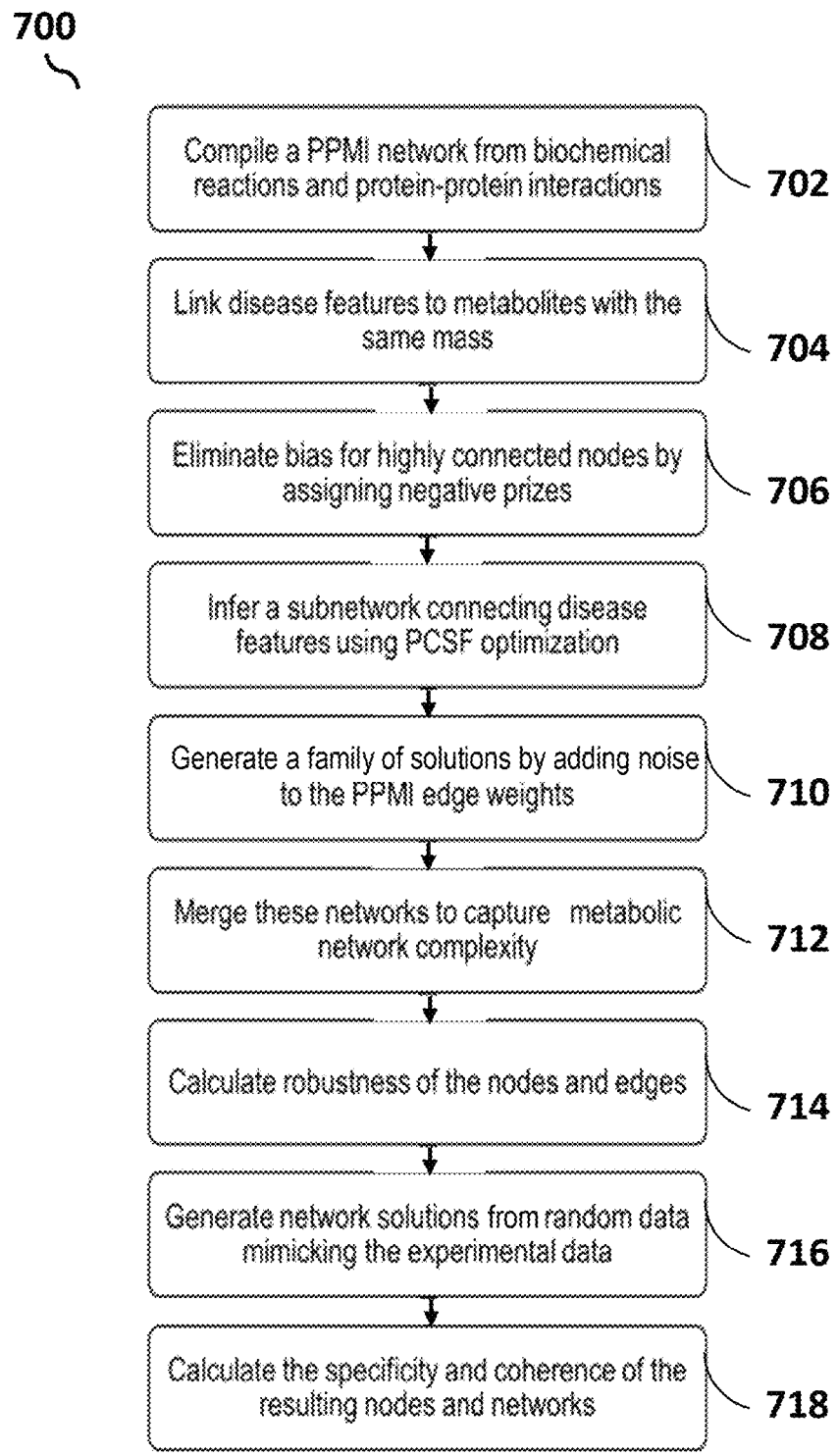
FIG. 7 is a flow chart illustrating a network-based approach for integrative analysis of untargeted metabolomics in accordance with some embodiments.

FIG. 7 is a flow chart illustrating a network-based approach for integrative analysis of untargeted metabolomics in accordance with some embodiments. PIUMet algorithm 700 comprises at least one or more steps of compiling a PPMI network from biochemical reactions and protein-protein interactions 702; linking disease features to metabolites with the same mass 704; eliminating bias for highly connected nodes by assigning negative prizes 706; inferring a subnetwork connecting disease features using PCSF optimization 708; generating a family of solutions by adding noise to the PPMI edges weights 710; merging these networks to capture metabolic network complexity 712; calculating robustness of the nodes and edges 714; generating network solutions from random data mimicking the experimental data 716; and calculating the specificity and coherence of the resulting nodes and networks 718.

To decipher the context of disease features, a PIUMet algorithm does not require their prior identification; instead, it embraces the ambiguous identity of features. A PIUMet algorithm may represent each disease feature as a node, connected to all metabolites with masses similar to the disease features. The connecting edges may be assigned an arbitrary and equal weight. In some embodiments, using network optimization techniques described below, a PIUMet algorithm identifies the subset of these metabolites most likely to correspond to disease features. It further calculates a robustness score R for each one of the resulting metabolites indicating the degree to which its identification is robust to network parameters w and the PPMI edge weights.

A PIUMet algorithm may search a PPMI interactome for a subnetwork connecting disease features using high-probability protein-protein and protein-metabolite interactions. The PIUMet algorithm may optimize the network using the prize-collecting Steiner forest algorithm, assigning prizes to disease features and costs to edge weights. Node prizes reflect the significance of feature dysregulation (as determined by the user), and edge costs are anticorrelated with the edge confidence scores. The optimum solution balances the desire to include as many disease features as possible with a reluctance to use low-confidence edges. Specifically, a sum of the prizes from connected disease features was maximized, while the edge costs included in the final network are minimized.

Figure 8:
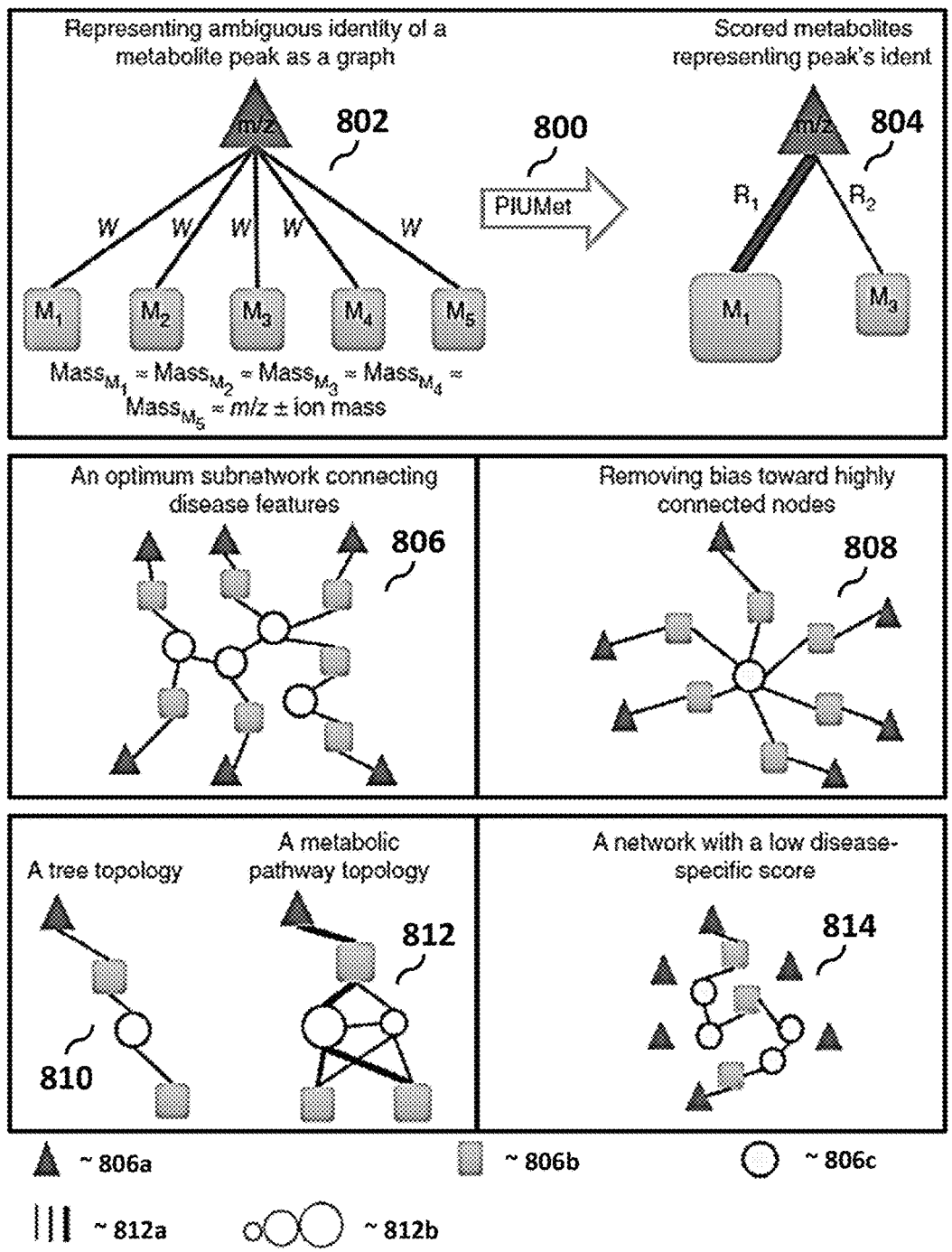
FIG. 8 is a series of network diagrams illustrating network-based approaches for integrative analysis of untargeted metabolomics in accordance with some embodiments.

FIG. 8 is a series of network diagrams illustrating network-based approaches for integrative analysis of untargeted metabolomics in accordance with some embodiments. PIUMet algorithm 800 embraces the ambiguous identity of disease features. In FIG. 8, PIUMet algorithm 800 first identifies putative metabolites $M_1$, $M_2$, $M_3$, $M_4$, and $M_5$ by matching a feature m/z based on mass:

$$Mass_{M_1} \approx Mass_{M_2} \approx Mass_{M_3} \approx Mass_{M_4} \approx Mass_{M_5} \approx \frac{m}{z} \pm \text{ion mass} \quad (6)$$

The ambiguous identity of each metabolite peak or feature may be represented as a node m/z, which is connected to the matched metabolites ($M_1$, $M_2$, $M_3$, $M_4$, and $M_5$) with edges, as in graph 802. PIUMet algorithm 800 then reduces the ambiguity in the assignment and scores each of these metabolites and edges. For example, graph 804 shows node m/z connected to metabolites $M_1$ and $M_3$, with a higher score to metabolite $M_1$ and corresponding edge $R_1$.

In an optimum PPMI subnetwork 806 that links disease features, metabolite peaks 806a connected to hidden metabolites 806b represent the disease features corresponding to the inferred metabolites in accordance with some embodiments. These hidden metabolites 806b and also hidden proteins 806c are connected by high-confidence protein-protein and protein-metabolites interactions.

Elimination of Bias Toward Highly Connected Nodes

A PIUMet algorithm may include one of several features to improve its accuracy. In some embodiments, the algorithm may eliminate bias toward highly connected nodes in the PPMI interactome such as ATP or ubiquitin. As these high-degree nodes can connect almost any nodes in the PPMI interactome, they provide little insight into altered pathways. In FIG. 8, subnetwork 808 is an example of an undesirable result that is biased toward highly connected nodes.

The PIUMet algorithm may penalize the inclusion of high-degree nodes by assigning a penalty correlated with the node's degree. In some embodiments, a PIUMet algorithm infers resulting networks that are unbiased toward highly connected nodes. The presence of several nodes in the PPMI interactome with a high degree of connectivity leads to a network in which terminal nodes are always linked via a high degree node. To obtain results that are not biased toward highly connected nodes, PIUMet may penalize the results that have a high-degree node by introducing a negative prize to nonterminal nodes, which is a multiple of their degree. Since nodes' degree distribution differ significantly between the metabolite and protein sets (t-test P=$8.16 \times 10^{-124}$), with an average of 35.18 in the metabolite set compared to 21.08 in the protein set, the negative prizes for protein and metabolite sets are defined as:

$$p(n) = \begin{cases} -\mu \times \text{degree}(n) & \text{if } n \in PPMI(P) \\ -\mu \times \text{degree}(n)^2 & \text{if } n \in PPMI(M) \end{cases} \quad (7)$$

where p(n) represents a prize for a Steiner node n, P represents a set of protein nodes in the PPMI interactome, M represents a set of metabolite nodes in the PPMI interactome, and $\mu$ represents the parameter that controls the effect of negative prizes. In some embodiments, this parameter is set equal to 0.015.

Generation of a Family of Resultant Networks

A PIUMet algorithm may further improve its accuracy, according to some embodiments, by generating a family of networks to infer the complex interconnections between substrates, enzymes, and products that cannot be represented in tree structures. In FIG. 8, subnetwork 810 is an example of a tree structure, whereas subnetwork 812 captures the complex topology of metabolic reactions with edge scores 812a and node scores 812b in accordance with some embodiments.

The algorithm may merge solutions from many runs that differ by quantities of random noise that are added to the PPMI edge weights to find multiple, high-probability interactions that connect disease features. The PIUMet algorithm then may calculate a robustness score R for resulting nodes and edges to account for uncertainty in molecular interactions.

In some embodiments, robust, disease-associated pathways that capture the complexity of metabolic networks are inferred. Since the solution to equation (5) is a tree, it cannot capture the complex topology of metabolic reactions including interconnection of substrates, enzymes, and products. In addition, there may be no confidence score associated with several protein-metabolite interactions, for which an arbitrary value of median confidence score of PPI was substituted. To address these issues, R resultant networks may be generated by adding small random noises to the PPMI edge weights. For this purpose, a small random value in the range of [0 $\varepsilon$] is added to the edge weights for R times. In some embodiments, c may be considered equal to one half of the standard deviation of the PPMI edge weight distribution (e.g., 0.046). The c value may be the same for any other disease as long as the underlying interactome is unchanged. According to some embodiments, this process leads to a family of inferred networks including multiple possible paths that link terminal nodes. The union of these networks may demonstrate the complex interconnection of metabolic pathways. In some embodiments, generating networks by adding random noise to the PPMI edge weights allows for the distinction of results that are robust in spite of the uncertainty in the interactome edge weights. According to some embodiments, a robustness score (alternatively a "recurrence score") for each node in the family of networks indicates a normalized frequency at which a node is present in the family of solutions. The robustness score is calculated as below:

$$R_{n_i} = \frac{\sum_{j=1}^{R} f_{n_i,j}}{\sum_{i=1}^{N} \sum_{j=1}^{R} f_{n_i,j}} \quad (8)$$

$$f_{n_i,j} = \begin{cases} 1 & \text{if } n_i \in F_j(n) \\ 0 & \text{otherwise} \end{cases} \quad (9)$$

where for a family of R resultant networks with N nodes, $R_{n_i}$ shows the robustness score of node $n_i \in N$, and $F_j(n)$ shows nodes in network j.

Node Specificity and Disease Specific Scores

A PIUMet algorithm may further improve its accuracy, according to some embodiments, by calculating a disease-specific score for each resulting node and a score for each network. These scores may be determined by generating a family of networks from randomly selected disease features that mimic the experimental data. A disease-specific score for each node is calculated by the frequency of the node in these "mock" networks. It has been observed that only a minority of the mock features were connected, and the connections were typically long paths. Thus, in contrast with real data, metabolites corresponding to randomly selected disease features were distributed apparently at random in the PPMI network. Based on this observation, a disease-specific score was defined for each network.

To measure the specificity of the PIUMet results to the disease of interest, networks may be generated by randomly selecting metabolite features with the same characteristics as disease features. In some embodiments, a detectable metabolite feature (DMF) set is defined as a set of metabolite features mimicking the experimental data. First, the DMF set includes mass-to-charge ratio m/z values that are detectable with the mass spectrometer used in the experiments. Second, the DMF metabolite features are matched to metabolites that belong to a superclass of metabolites that can be separated via the liquid chromatography step. To distinguish these metabolites, chemical taxonomy information, including superclass, may be obtained from a database, such as the HDMD database. Finally, these matched metabolites belong to the PPMI network. The definition of the DMF set is:

$$DMF = \left\{ dmf \,\middle|\, \exists\, M_{dmf} : PPMI(M) \wedge \frac{m}{z_{min}} \leq \right.$$
$$\left. \frac{m}{z_{dmf}} \leq \frac{m}{z_{max}} \wedge \exists\, Md_{mf} : \text{Detectable Superclass} \right\} \quad (10)$$

Figure 9:
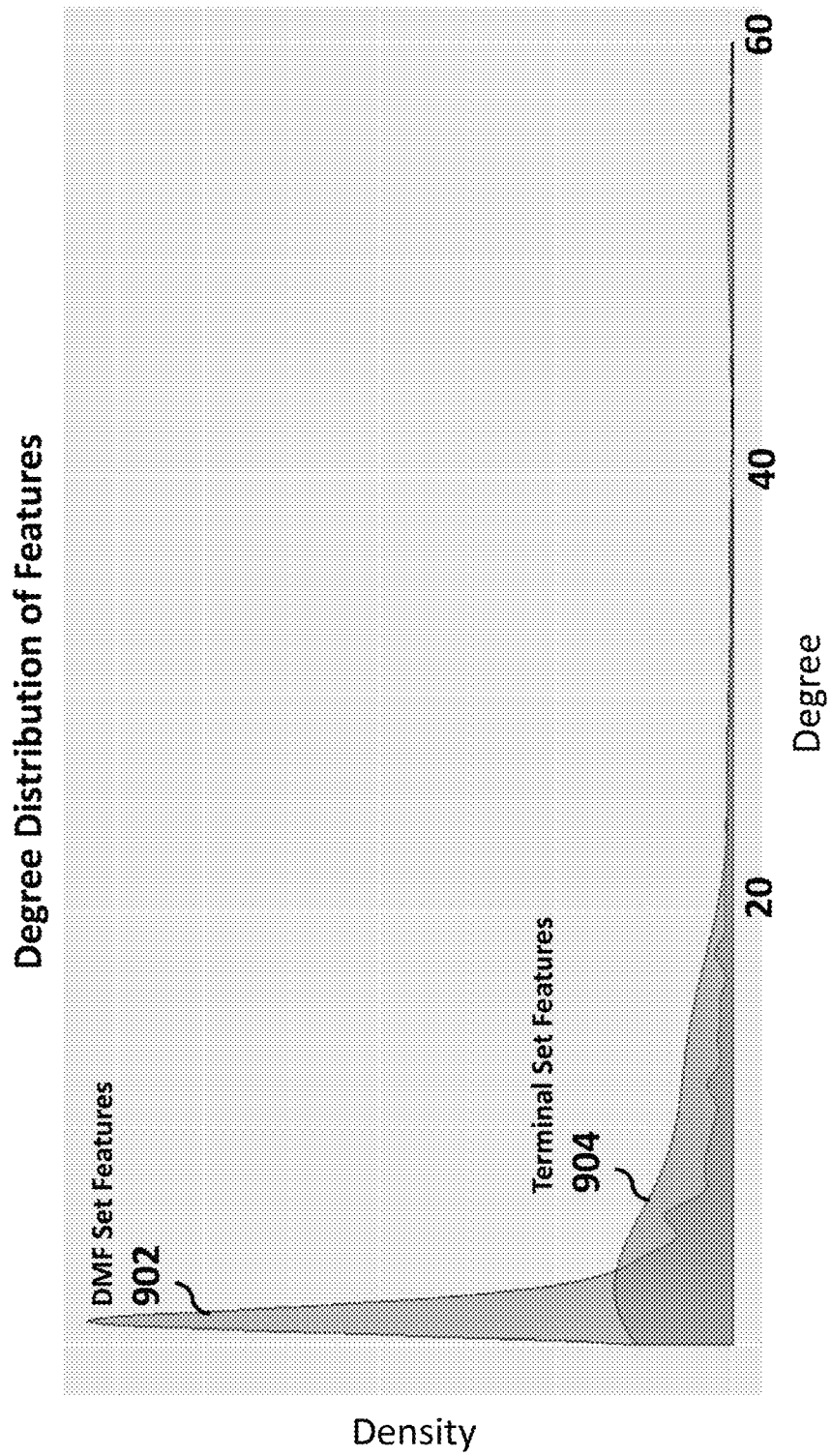
FIG. 9 is a plot comparing the degree distribution of features (i.e., the distribution of a number of metabolites corresponding to a feature) from a terminal set and a detectable metabolite feature (DMF) set in accordance with some embodiments.

The degree of each feature in the DMF set indicates the number of potential matched metabolites. FIG. 9 is a plot comparing the degree distribution of features from a DMF set 902 and a terminal set 904 in accordance with some embodiments. Here, the degree of a feature is the number of metabolites corresponding to the feature (e.g., matched peaks m/z from metabolomic experimental data) or corresponding to the chemical formula nodes in accordance with some embodiments.

Figure 10:
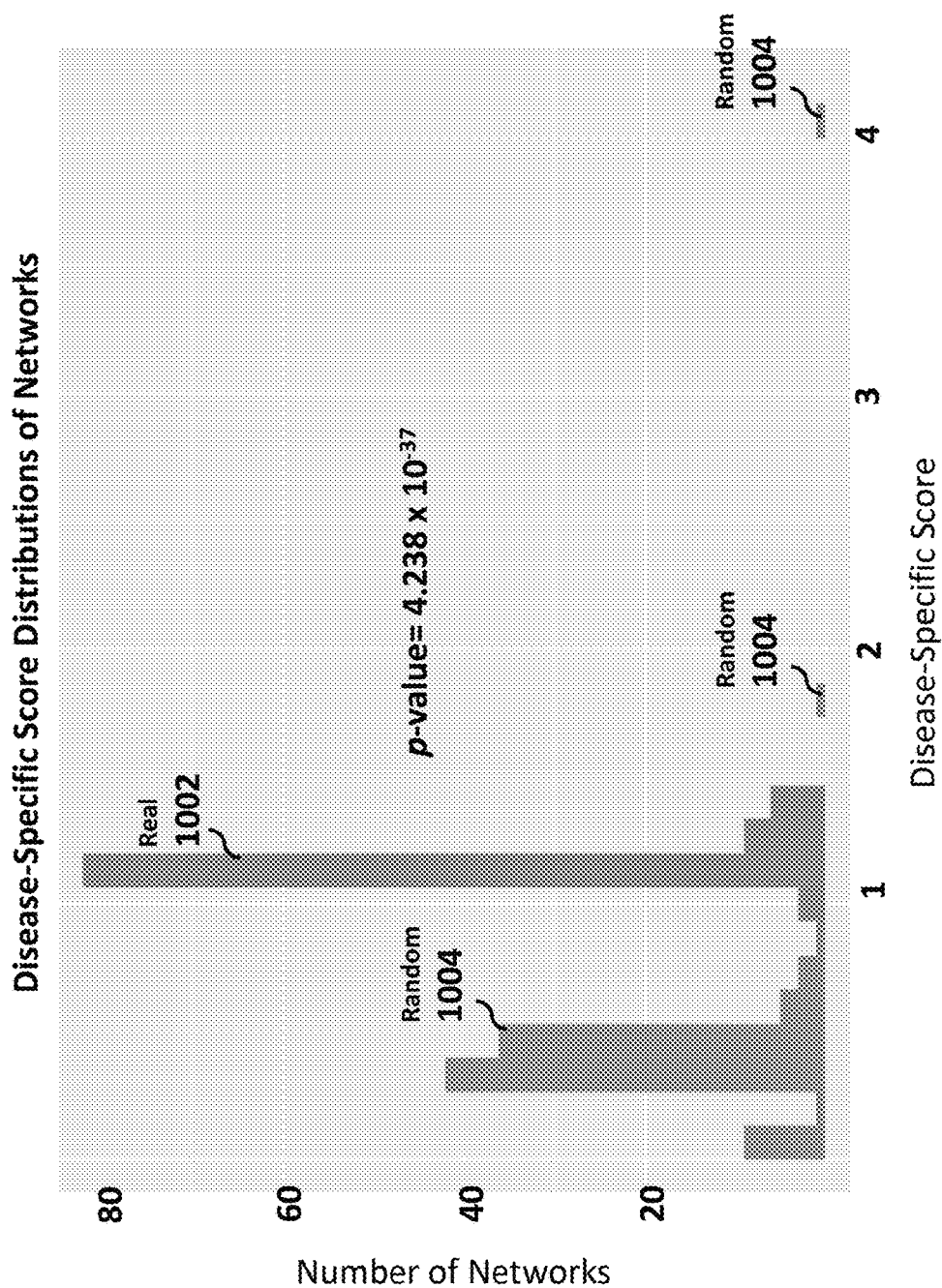
FIG. 10 is a plot comparing disease-specific score distributions of networks inferred from real and randomly selected metabolite features in accordance with some embodiments.

FIG. 10 is a plot comparing disease-specific score distributions of networks inferred from real metabolite features 1002 and randomly selected metabolite features 1004 in accordance with some embodiments. The plot shows that the scores for the real results 1002 are significantly higher than random results 1004 (P-value=$4.238 \times 10^{-37}$).

For a terminal set with size T, in some embodiments, T features are randomly selected from the DMF set, in which the degree distribution of the selected features is similar to the terminal set. This process may be repeated R times. Each of these R randomly chosen features is provided as input to a PIUMet algorithm, resulting in R networks. These networks may be compared to the networks obtained from the experimental data to calculate disease-specific scores, which indicate the frequency of a node in the networks obtained from randomly selected disease features and is defined as:

$$\text{Node Specificity}(n_i) = \frac{\sum_{i=1}^{R} f_i}{R} \quad (11)$$

$$f_{n_i,j} = \begin{cases} 1 & \text{if } n \in RF_j(n) \\ 0 & \text{otherwise} \end{cases} \quad (12)$$

where $n_i$ is a node in the family of the networks obtained from disease features. For R random feature sets, $RF_j(n)$ is a network with n nodes that connects random features.

In the resulting networks from randomly selected disease features, a majority of the features may remain unconnected (singletons), and some may be linked via a long path of protein-protein and protein-metabolite interactions. These properties may be quantified by calculating the disease-specific score for each resulting network as the number of the connected metabolite features divided by the number of Steiner nodes. The disease-specific score then may be calculated as:

$$\text{Disease Specific Score} = \frac{\text{\# of terminals} - \text{\# of Singletons}}{\text{\# of Steiner nodes}} \quad (13)$$

According to some embodiments, the disease-specific scores of resulting networks from disease features may be compared to those obtained from randomly selected features using the student t-test. In FIG. 8, subnetwork 814 is an example of a network generated from randomly chosen mock data sets, in which the majority of input nodes remain separated, and a few are connected via a long path of protein-protein and protein-metabolite interactions, for a low disease-specific score in accordance with some embodiments.

Figure 11:
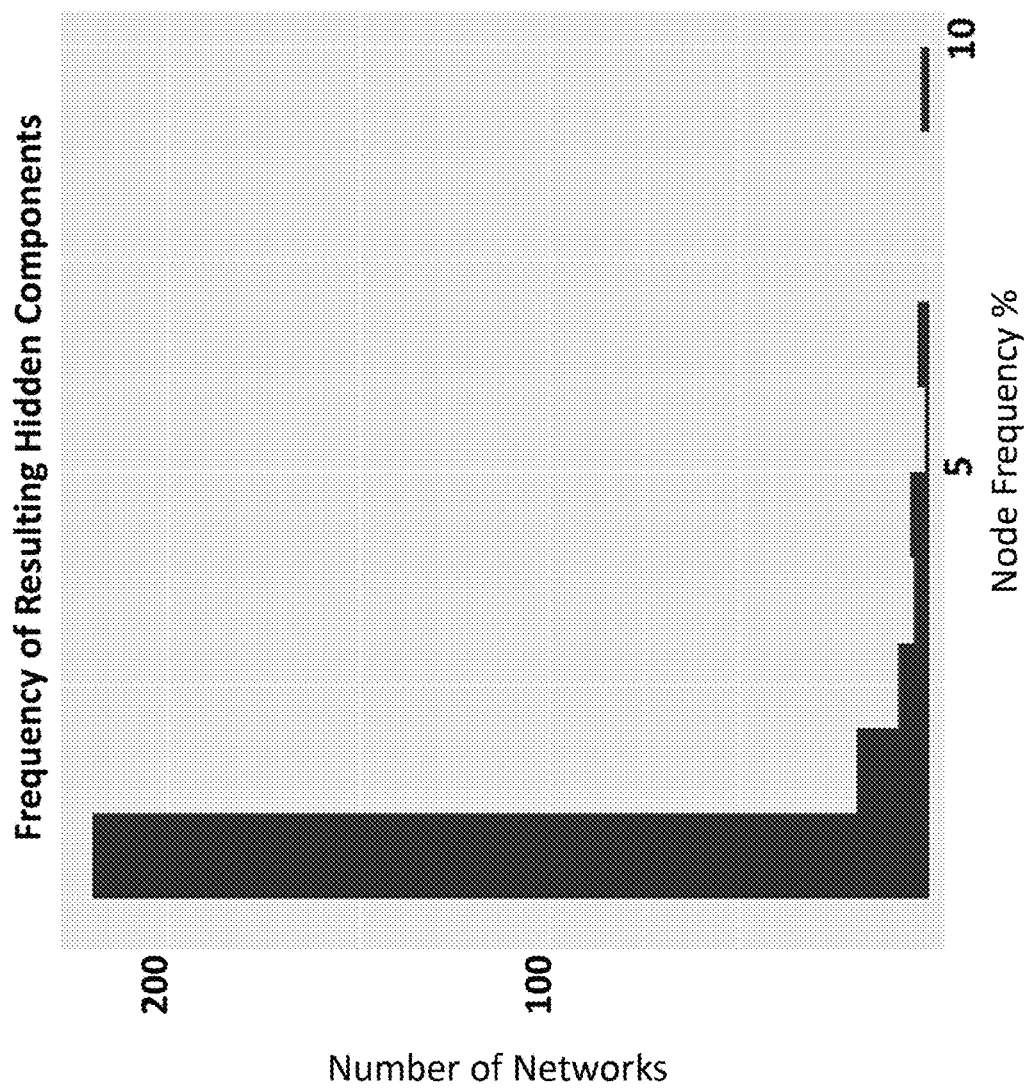
FIG. 11 is a plot illustrating the frequency of resulting hidden components from real data in networks inferred from randomly selected metabolite features in accordance with some embodiments.

FIG. 11 is a plot illustrating the frequency of resulting hidden components from real data in networks inferred from randomly selected metabolite features in accordance with some embodiments.

Identification of Background Nodes

According to some embodiments, a PIUMet algorithm distinguishes a relevant set of background nodes essential for downstream significance analysis of resulting networks, such as gene ontology enrichment. The background nodes are a subset of the PPMI nodes that can connect metabolite features mimicking the experimental data (the DMF set features). To identify background nodes, the weighted shortest path length between the PPMI nodes and metabolites corresponding to DMF set features may be calculated. A background set may be defined as:

$$B = \{b \mid b \in PPMI(N) \wedge \text{weighted shortest path length}(b, DMF(M)) \leq \varepsilon\} \quad (14)$$

where B shows background nodes DMF(M) is a set of metabolites corresponding to the DMF set features, and PPMI(N) is the set of the PPMI nodes. In some embodiments, c may be considered equal to 0.4; sensitivity analysis on the value of c resulted in similar outcomes (results on file with Applicant).

Figure 12:
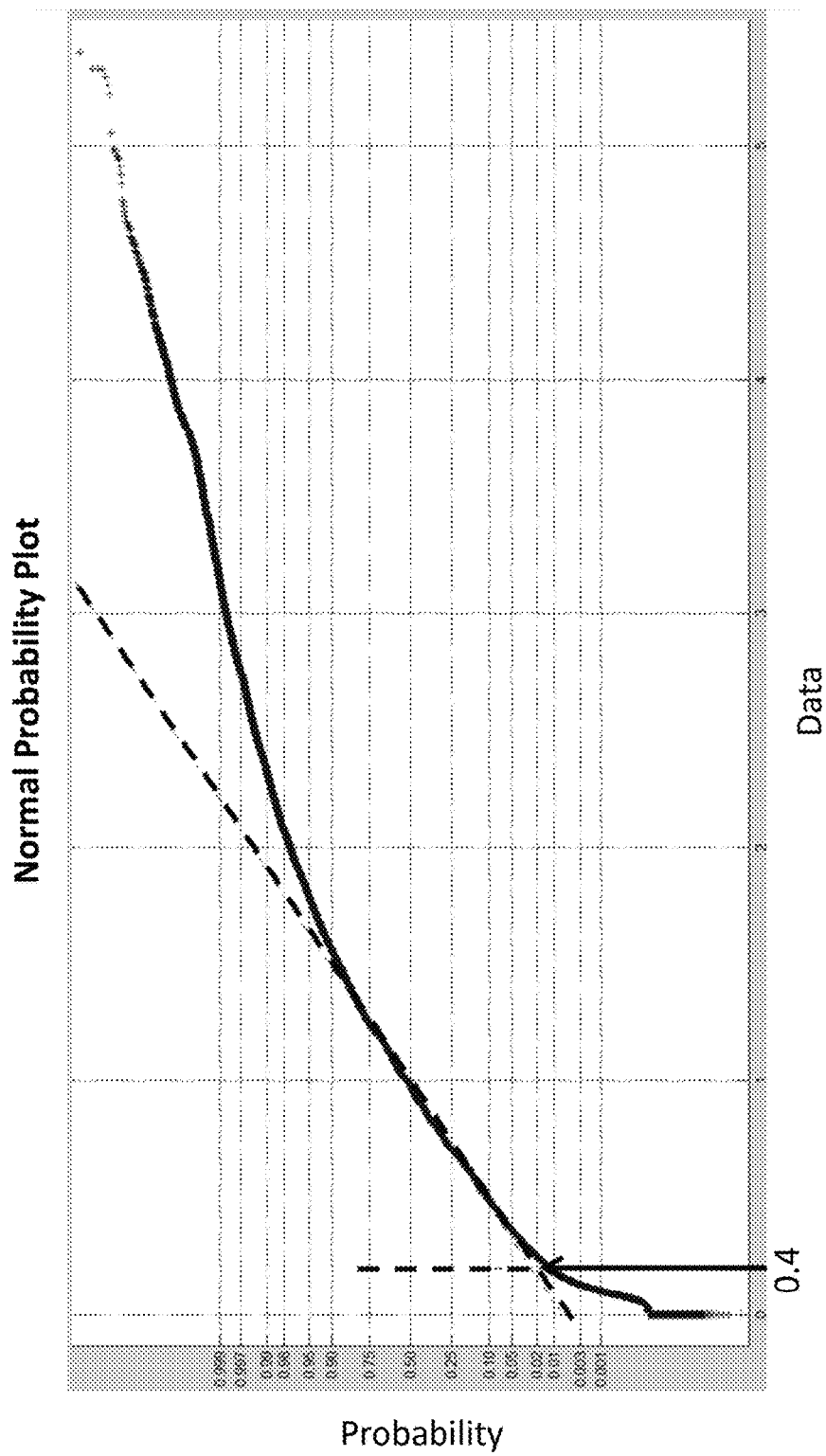
FIG. 12 is a plot illustrating normal probability of the weighted shortest path length of all the proteins in a network to lipid-associated proteins (LPs) in accordance with some embodiments.

FIG. 12 is a plot illustrating normal probability of the weighted shortest path length of all the proteins in a network to lipid-associated proteins (LPs) in accordance with some embodiments.

Experimental Data Collection Using STHdh Cell Line Model of Huntington's Disease According to some embodiments, various omic data of STHdh cell line model of Huntington's Disease (HD) were collected. HD is a genetic, neurodegenerative disorder caused by a CAG repeat expansion in the gene encoding huntingtin protein. Conditionally immortalized homozygote striatal neuronal progenitor cell lines (STHdh) derived from knock-in mice embryos expressing either wildtype Huntington with seven CAG repeats (STHdh Q7, available as CH00097 from Coriell Institute for Medical Research, Camden, N.J.) or mutant poly-glutamine expanded huntingtin with 111 CAG repeats (STHdh Q111, available as CH00095 from Coriell Institute for Medical Research, Camden, N.J.) were used.

According to some embodiments, the cells were maintained in a humid incubator at 33° C. and 5% $CO_2$. Culture medium was changed every 2 days, and cells were subcultured when they reached 85% confluence. The passage number was kept below 14. To exclude *mycoplasma* contamination, cells were routinely tested with the PCR *Mycoplasma* Detection Kit (available from Applied Biological Materials Inc., Richmond, BC, Canada). The cell lines were genotyped by PCR. Before each experiment, the temperature was raised at 39° C. for 48 hours to halt proliferation and reduce cell-cycle differences between the two lines. Cells were subsequently washed twice with ice-cold phosphate-buffered saline, scraped on ice and pelleted by centrifugation at 450 g for 5 minutes at 4° C. Cell pellets were flash-frozen with liquid nitrogen and stored at −80° C. until use.

Global Lipid Profiling of STHdh Cell Line Model of HD

According to some embodiments, lipids were extracted from STHdh cells. The cells were scraped from a 10-cm plate in 1 mL of cold PBS and transferred to a glass vial which was vortexed with a cold mixture of 1 mL MeOH and 2 mL chloroform. The resulting mixture was centrifuged and the organic phase containing lipids was dried under a stream of $N_2$ and stored at −80° C. before injection for LC-MS analysis.

Global lipidomics were performed with an 1200 Series High-Performance Liquid Chromatography (HPLC) online with a 6220 ElectroSpray Ionization Time-of-Flight (ESI-TOF) LC-MS device (both available from Agilent Technologies, Santa Clara, Calif.). Data were acquired in positive and negative ionization modes. For the negative mode, a Gemini® C18 HPLC column (available from Phenomenex, Torrance, Calif.) or Inspire™ C18 HPLC column (available from Dikma Technologies Inc., Lake Forest, Calif.) (5 μm, 4.6 mm×50 mm) was used with a guard column (C18, 2 μm frit, 2 mm×20 mm). Solvent A was 95:5 water:methanol with 0.1% ammonium hydroxide, and solvent B was 60:35:5 isopropanol:methanol:water with 0.1% ammonium hydroxide. For the positive mode, a Luna® C5 column (available from Phenomenex, Torrance, Calif.) or Bio-Bond™ C4 column (available from Dikma Technologies Inc., Lake Forest, Calif.) (5 μm, 4.6 mm×50 mm) was used with a guard column (C4, 2 μm frit, 2 mm×20 mm). Solvent A was 95:5 water:methanol with 0.1% formic acid and 5 mM ammonium formate, and solvent B was 60:35:5 isopropanol:methanol:water with 0.1% formic acid and 5 mM ammonium formate. The identical gradient was used for both modes. The gradient was held at 0% B between zero and five minutes, changed to 20% B at 5.1 min, increased linearly from 20% B to 100% B between 5.1 and 45 minutes, held at 100% B between 45.1 and 53 minutes, and returned to 0% B at 53.1 minutes and held at 0% B between 53.1 and 60 minutes to allow column re-equilibration. The flow rate was maintained at 0.1 mL/min between zero and five minutes to counter the increase in pressure due to chloroform injection. The flow rate was 0.4 mL/min between 5.1 and 45 minutes, and 0.5 mL/min between 45.1 and 60 minutes. Injection volume was 10-30 μL. The capillary, fragmentor, and skimmer voltages were 3.5 kV, 100 V and 60 V, respectively. The drying gas temperature was 350° C., drying gas flow rate was 10 l min$^{-1}$ and nebulizer pressure was 45 p.s.i. Data were collected in both profile and centroid modes using a mass range of 100-1500 Da. For untargeted analysis, raw data were converted to .mzXML format and analyzed by XCMS, which considers nonlinear alignments of features from different samples. XCMS output files were filtered by statistical significance (P≤0.05), fold change (≥3) and reproducibility across four independent data sets, and the remaining ions further verified by manual integration in Qualitative Analysis software (available from Agilent Technologies, Santa Clara, Calif.).

Measuring global levels of lipids using LC-MS, 115 metabolite features were found that differed significantly between the lines (P-value≤0.01, two-tailed student's t-test). Of these, 37 features had masses that matched to 296 potential metabolites in a PPMI network (see TABLE 3 below). A PIUMet algorithm identified the network connecting more than 51% of these features via hidden metabolites and proteins. The resulting networks had significantly higher disease-specific scores than control networks (P-value=$4.238 \times 10^{-37}$) as shown in FIG. 10, and the nodes were specific to disease (disease-specific score ≥90%) as shown in FIG. 11.

TABLE 3

| Feature (mode_m/z_RT) | Formula | Q7/Q111 | pval | Recon_ID | HMDB_ID | Name_Formula |
|---|---|---|---|---|---|---|
| Pos_383_33 | C27H42O | 0.103195004 | 0.0016 | M_zym_int2_r | — | zymosterol intermediate 2_C27H42O |
| Neg_301_29 | C20H30O2 | 2.729397607 | 6.87E−05 | M_tmndnc_e | HMDB 01999 | timnodonic acid C20:5, n-3_C20H29O2 |
| Neg_301_29 | C20H30O2 | 2.729397607 | 6.87E−05 | M_tmndnc_c | HMDB 01999 | timnodonic acid C20:5, n-3_C20H29O2 |
| Neg_365_38 | C24H46O2 | 4.414397246 | 0.00064736 | M_nrvnc_e | HMDB 02368 | nervonate_C24H45O2 |
| Neg_365_38 | C24H46O2 | 4.414397246 | 0.00064736 | M_nrvnc_c | HMDB 02368 | nervonate_C24H45O2 |
| Neg_367_40 | C24H48O2 | 3.401668246 | 0.000704799 | M_lgnc_x | HMDB 02003 | lignocerate_C24H47O2 |
| Neg_367_40 | C24H48O2 | 3.401668246 | 7.05E−04 | M_lgnc_m | HMDB 02003 | lignocerate_C24H47O2 |
| Neg_367_40 | C24H48O2 | 3.401668246 | 7.05E−04 | M_lgnc_e | HMDB 02003 | lignocerate_C24H47O2 |
| Neg_367_40 | C24H48O2 | 3.401668246 | 7.05E−04 | M_lgnc_c | HMDB 02003 | lignocerate_C24H47O2 |
| Neg_305_30 | C20H34O2 | 0.338689921 | 1.07E−06 | M_HC02100_r | — | Dihomo-gamma-linolenate_C20H33O2 |
| Neg_305_30 | C20H34O2 | 0.338689921 | 1.07E−06 | M_HC02100_l | — | Dihomo-gamma-linolenate_C20H33O2 |
| Neg_305_30 | C20H34O2 | 0.338689921 | 1.07E−06 | M_dlnlcg_e | HMDB 02925 | dihomo-gamma-linolenic acid (n-6)_C20H33O2 |

TABLE 3-continued

| Feature (mode__m/z__RT) | Formula | Q7/Q111 | pval | Recon_ID | HMDB_ID | Name_Formula |
|---|---|---|---|---|---|---|
| Neg_305_30 | C20H34O2 | 0.338689921 | 1.07E−06 | M_dlnlcg_c | HMDB 02925 | dihomo-gamma-linolenic acid (n-6)__C20H33O2 |
| Pos_383_33 | C27H42O | 0.103195004 | 0.0016 | M_ddsmsterol_r | HMDB 03896 | 7-dehydrodesmosterol__C27H42O |
| Neg_301_29 | C20H30O2 | 2.729397607 | 6.87E−05 | M_CE5932_c | — | 13,14-epoxy-retinol__C20H30O2 |
| Neg_301_29 | C20H30O2 | 2.729397607 | 6.87E−05 | M_CE5013_c | — | 14-hydroxy-4,14-retro-retinol__C20H30O2 |
| Neg_301_29 | C20H30O2 | 2.729397607 | 6.87E−05 | M_CE2540_x | — | timnodonate__C20H29O2 |
| Neg_301_29 | C20H30O2 | 2.729397607 | 6.87E−05 | M_CE2540_r | — | timnodonate__C20H29O2 |
| Neg_301_29 | C20H30O2 | 2.729397607 | 6.87E−05 | M_CE2540_n | — | timnodonate__C20H29O2 |
| Neg_301_29 | C20H30O2 | 2.729397607 | 6.87E−05 | M_CE2540_c | — | timnodonate__C20H29O2 |
| Neg_305_30 | C20H34O2 | 0.338689921 | 1.07E−06 | M_CE2516_r | — | (8Z,11Z,14Z)-eicosatrienoic acid__C20H33O2 |
| Neg_305_30 | C20H34O2 | 0.338689921 | 1.07E−06 | M_CE2516_c | — | (8Z,11Z,14Z)-eicosatrienoic acid__C20H33O2 |
| Neg_365_38 | C24H46O2 | 4.414397246 | 0.00064736 | M_CE2513_c | — | 15-tetracosenoate__C24H45O2 |
| Neg_309_34 | C20H38O2 | 2.548189915 | 0.000453648 | M_CE2510_c | — | 11-cis-eicosenoate__C20H37O2 |
| Pos_383_33 | C27H42O | 0.103195004 | 0.0016 | M_CE2321_n | HMDB 03896 | cholesta-5,7,24-trien-3beta-ol__C27H42O |
| Pos_383_33 | C27H42O | 0.103195004 | 0.0016 | M_CE2321_c | HMDB 03896 | cholesta-5,7,24-trien-3beta-ol__C27H42O |
| Neg_291_29 | C19H32O2 | 8.117675378 | 1.82E−05 | M_CE2209_c | HMDB 00554 | 5alpha-androstane-3alpha,17beta-diol__C19H32O2 |
| Neg_301_29 | C20H30O2 | 2.729397607 | 6.87E−05 | M_CE1761_r | — | 4-hydroxyvitamin A1__C20H30O2 |
| Neg_301_29 | C20H30O2 | 2.729397607 | 6.87E−05 | M_CE1761_c | — | 4-hydroxyvitamin A1__C20H30O2 |
| Neg_159_10 | C8H16O3 | 0.203262745 | 4.21E−05 | — | HMDB 01954 | 3-Hydroxyoctanoic acid__C8H16O3 |
| Neg_159_10 | C8H16O3 | 0.203262745 | 4.21E−05 | — | HMDB 59867 | Ethyl 2-hydroxy-4-methylpentanoate__C8H16O3 |
| Neg_159_10 | C8H16O3 | 0.203262745 | 4.21E−05 | — | HMDB 02264 | (R)-2-Hydroxycaprylic acid__C8H16O3 |
| Neg_159_10 | C8H16O3 | 0.203262745 | 4.21E−05 | — | HMDB 10722 | (R)-3-Hydroxyoctanoic acid__C8H16O3 |
| Neg_159_10 | C8H16O3 | 0.203262745 | 4.21E−05 | — | HMDB 32827 | Peroxyoctanoic acid__C8H16O3 |
| Neg_159_10 | C8H16O3 | 0.203262745 | 4.21E−05 | — | HMDB 00486 | 7-Hydroxyoctanoic acid__C8H16O3 |
| Neg_159_10 | C8H16O3 | 0.203262745 | 4.21E−05 | — | HMDB 31509 | Ethyl (±)-3-hydroxyhexanoate__C8H16O3 |
| Neg_159_10 | C8H16O3 | 0.203262745 | 4.21E−05 | — | HMDB 59825 | Isoamyl lactate__C8H16O3 |
| Neg_159_10 | C8H16O3 | 0.203262745 | 4.21E−05 | — | HMDB 32270 | (+/−)-Ethyl 2-hydroxy-3-methylvalerate__C8H16O3 |
| Neg_159_10 | C8H16O3 | 0.203262745 | 4.21E−05 | — | HMDB 13899 | 3-Hydroxyvalproic acid__C8H16O3 |
| Neg_159_10 | C8H16O3 | 0.203262745 | 4.21E−05 | — | HMDB 13898 | 5-Hydroxyvalproic acid__C8H16O3 |
| Neg_159_10 | C8H16O3 | 0.203262745 | 4.21E−05 | — | HMDB 00711 | Hydroxyoctanoic acid__C8H16O3 |
| Neg_159_10 | C8H16O3 | 0.203262745 | 4.21E−05 | — | HMDB 13900 | 4-Hydroxyvalproic acid__C8H16O3 |
| Neg_197_23 | C12H22O2 | 0.270690124 | 6.74E−07 | — | HMDB 38924 | 2-Hexenyl hexanoate__C12H22O2 |
| Neg_197_23 | C12H22O2 | 0.270690124 | 6.74E−07 | — | HMDB 32214 | cis-4-Decenyl acetate__C12H22O2 |
| Neg_197_23 | C12H22O2 | 0.270690124 | 6.74E−07 | — | HMDB 37742 | xi-5-Dodecanolide__C12H22O2 |
| Neg_197_23 | C12H22O2 | 0.270690124 | 6.74E−07 | — | HMDB 40158 | Hexyl 2-methyl-3-pentenoate__C12H22O2 |
| Neg_197_23 | C12H22O2 | 0.270690124 | 6.74E−07 | — | HMDB 34160 | (±)-Citronellyl acetate__C12H22O2 |
| Neg_197_23 | C12H22O2 | 0.270690124 | 6.74E−07 | — | HMDB 39220 | Ethyl 4-decenoate__C12H22O2 |
| Neg_197_23 | C12H22O2 | 0.270690124 | 6.74E−07 | — | HMDB 29585 | Methyl 10-undecenoate__C12H22O2 |
| Neg_197_23 | C12H22O2 | 0.270690124 | 6.74E−07 | — | HMDB 10729 | trans-Dodec-2-enoic acid__C12H22O2 |

TABLE 3-continued

| Feature (mode_m/z_RT) | Formula | Q7/Q111 | pval | Recon_ID | HMDB_ID | Name_Formula |
|---|---|---|---|---|---|---|
| Neg_197_23 | C12H22O2 | 0.270690124 | 6.74E−07 | — | HMDB 40361 | 1,1-Dimethoxy-3,7-dimethyl-2,6-octadiene_C12H22O2 |
| Neg_197_23 | C12H22O2 | 0.270690124 | 6.74E−07 | — | HMDB 36182 | 5,5-Dibutyl-4,5-dihydro-2(3H)furanone_C12H22O2 |
| Neg_197_23 | C12H22O2 | 0.270690124 | 6.74E−07 | — | HMDB 31683 | xi-Dihydro-5-octyl-2(3H)-furanone_C12H22O2 |
| Neg_197_23 | C12H22O2 | 0.270690124 | 6.74E−07 | — | HMDB 00529 | 5-Dodecenoic acid_C12H22O2 |
| Neg_197_23 | C12H22O2 | 0.270690124 | 6.74E−07 | — | HMDB 33378 | cis-3-Hexenyl hexanoate_C12H22O2 |
| Neg_197_23 | C12H22O2 | 0.270690124 | 6.74E−07 | — | HMDB 37329 | Ethyl 2-decenoate_C12H22O2 |
| Neg_197_23 | C12H22O2 | 0.270690124 | 6.74E−07 | — | HMDB 37186 | Rhodinyl acetate_C12H22O2 |
| Neg_197_23 | C12H22O2 | 0.270690124 | 6.74E−07 | — | HMDB 29763 | Allyl nonanoate_C12H22O2 |
| Neg_197_23 | C12H22O2 | 0.270690124 | 6.74E−07 | — | HMDB 38895 | 7-Hexyl-2-oxepanone_C12H22O2 |
| Neg_197_23 | C12H22O2 | 0.270690124 | 6.74E−07 | — | HMDB 41264 | (±)-Menthyl acetate_C12H22O2 |
| Neg_197_23 | C12H22O2 | 0.270690124 | 6.74E−07 | — | HMDB 41449 | [(3,7-Dimethyl-6-octenyl)oxy]acet-aldehyde_C12H22O2 |
| Neg_197_23 | C12H22O2 | 0.270690124 | 6.74E−07 | — | HMDB 34844 | Citronellyl acetate_C12H22O2 |
| Neg_197_23 | C12H22O2 | 0.270690124 | 6.74E−07 | — | HMDB 38081 | 2-Octenyl butyrate_C12H22O2 |
| Neg_197_23 | C12H22O2 | 0.270690124 | 6.74E−07 | — | HMDB 40163 | Hexyl 2-methyl-4-pentenoate_C12H22O2 |
| Neg_197_23 | C12H22O2 | 0.270690124 | 6.74E−07 | — | HMDB 32235 | 2,6-Dimethyl-5-heptenal propyleneglycol acetal_C12H22O2 |
| Neg_197_23 | C12H22O2 | 0.270690124 | 6.74E−07 | — | HMDB 38269 | Hexyl 2E-hexenoate_C12H22O2 |
| Neg_197_23 | C12H22O2 | 0.270690124 | 6.74E−07 | — | HMDB 37498 | 1-Ethenylhexyl butanoate_C12H22O2 |
| Neg_197_23 | C12H22O2 | 0.270690124 | 6.74E−07 | — | HMDB 32248 | 11-Dodecenoic acid_C12H22O2 |
| Neg_197_23 | C12H22O2 | 0.270690124 | 6.74E−07 | — | HMDB 37813 | 3-Heptyldihydro-5-methyl-2(3H)-furanone_C12H22O2 |
| Neg_197_23 | C12H22O2 | 0.270690124 | 6.74E−07 | — | HMDB 37305 | Methyl 9-undecenoate_C12H22O2 |
| Neg_223_25 | C14H24O2 | 0.181423204 | 7.36E−06 | — | HMDB 36424 | Allyl undecylenate_C14H24O2 |
| Neg_223_25 | C14H24O2 | 0.181423204 | 7.36E−06 | — | HMDB 31015 | Ethyl (2E,6Z)-dodecadienoate_C14H24O2 |
| Neg_223_25 | C14H24O2 | 0.181423204 | 7.36E−06 | — | HMDB 32524 | Terpinyl isobutyrate_C14H24O2 |
| Neg_223_25 | C14H24O2 | 0.181423204 | 7.36E−06 | — | HMDB 32342 | Isobornyl isobutyrate_C14H24O2 |
| Neg_223_25 | C14H24O2 | 0.181423204 | 7.36E−06 | — | HMDB 38259 | Neryl butyrate_C14H24O2 |
| Neg_223_25 | C14H24O2 | 0.181423204 | 7.36E−06 | — | HMDB 32053 | alpha-Terpineol butanoate_C14H24O2 |
| Neg_223_25 | C14H24O2 | 0.181423204 | 7.36E−06 | — | HMDB 38246 | Bornyl butyrate_C14H24O2 |
| Neg_223_25 | C14H24O2 | 0.181423204 | 7.36E−06 | — | HMDB 39129 | Goshuyic acid_C14H24O2 |
| Neg_223_25 | C14H24O2 | 0.181423204 | 7.36E−06 | — | HMDB 38260 | Geranyl 2-methylpropanoate_C14H24O2 |
| Neg_223_25 | C14H24O2 | 0.181423204 | 7.36E−06 | — | HMDB 00560 | 5,8-Tetradecadienoic acid_C14H24O2 |
| Neg_223_25 | C14H24O2 | 0.181423204 | 7.36E−06 | — | HMDB 37814 | 2-Propenyl cyclohexane-pentanoate_C14H24O2 |
| Neg_223_25 | C14H24O2 | 0.181423204 | 7.36E−06 | — | HMDB 30427 | Linalyl butyrate_C14H24O2 |
| Neg_223_25 | C14H24O2 | 0.181423204 | 7.36E−06 | — | HMDB 30426 | Linalyl isobutyrate_C14H24O2 |
| Neg_249_27 | C16H26O2 | 0.262919919 | 1.74E−05 | — | HMDB 37631 | 3-Methyl-alpha-ionyl acetate_C16H26O2 |
| Neg_249_27 | C16H26O2 | 0.262919919 | 1.74E−05 | — | HMDB 37712 | [2,2-bis(2-methylpropoxy) ethyl]benzene_C16H26O2 |
| Neg_249_27 | C16H26O2 | 0.262919919 | 1.74E−05 | — | HMDB 35293 | Norambreinolide_C16H26O2 |

TABLE 3-continued

| Feature (mode__m/z__RT) | Formula | Q7/Q111 | pval | Recon__ID | HMDB__ID | Name__Formula |
|---|---|---|---|---|---|---|
| Neg__251__29 | C16H28O2 | 0.313820123 | 4.97E−06 | — | HMDB 31086 | (Z)-7-Hexadecen-1,16-olide__C16H28O2 |
| Neg__251__29 | C16H28O2 | 0.313820123 | 4.97E−06 | — | HMDB 29351 | Geranyl hexanoate__C16H28O2 |
| Neg__251__29 | C16H28O2 | 0.313820123 | 4.97E−06 | — | HMDB 00477 | 7Z,10Z-Hexadecadienoic acid__C16H28O2 |
| Neg__251__29 | C16H28O2 | 0.313820123 | 4.97E−06 | — | HMDB 30429 | Linalyl hexanoate__C16H28O2 |
| Neg__251__29 | C16H28O2 | 0.313820123 | 4.97E−06 | — | HMDB 32340 | Isoambrettolide__C16H28O2 |
| Neg__251__29 | C16H28O2 | 0.313820123 | 4.97E−06 | — | HMDB 38255 | Geranyl 2-ethylbutyrate__C16H28O2 |
| Neg__251__29 | C16H28O2 | 0.313820123 | 4.97E−06 | — | HMDB 39131 | Ethyl (Z,Z)-5,8-tetradecadienoate__C16H28O2 |
| Neg__251__29 | C16H28O2 | 0.313820123 | 4.97E−06 | — | HMDB 37805 | D6-Ambrettolide__C16H28O2 |
| Neg__293__28 | C18H30O3 | 0.146766538 | 1.34E−05 | — | HMDB 31088 | 12,13-Epoxy-9,15-octadecadienoic acid__C18H30O3 |
| Neg__293__28 | C18H30O3 | 0.146766538 | 1.34E−05 | — | HMDB 10203 | 13-HOTE__C18H30O3 |
| Neg__293__28 | C18H30O3 | 0.146766538 | 1.34E−05 | — | HMDB 10200 | A-12(13)-EpODE__C18H30O3 |
| Neg__293__28 | C18H30O3 | 0.146766538 | 1.34E−05 | — | HMDB 10206 | 15(16)-EpODE__C18H30O3 |
| Neg__293__28 | C18H30O3 | 0.146766538 | 1.34E−05 | — | HMDB 30995 | (2'E,4'Z,8E)-Colneleic acid__C18H30O3 |
| Neg__293__28 | C18H30O3 | 0.146766538 | 1.34E−05 | — | HMDB 34586 | (9Z,12Z,14E)-16-Hydroxy-9,12,14-octadecatrienoic acid__C18H30O3 |
| Neg__293__28 | C18H30O3 | 0.146766538 | 1.34E−05 | — | HMDB 10224 | 9-HOTE__C18H30O3 |
| Neg__293__28 | C18H30O3 | 0.146766538 | 1.34E−05 | — | HMDB 29969 | Squamostanal A__C18H30O3 |
| Neg__293__28 | C18H30O3 | 0.146766538 | 1.34E−05 | — | HMDB 30950 | 15,16-Epoxy-9,12-octadecadienoic acid__C18H30O3 |
| Neg__293__28 | C18H30O3 | 0.146766538 | 1.34E−05 | — | HMDB 31103 | 2-Hydroxylinolenic acid__C18H30O3 |
| Neg__293__28 | C18H30O3 | 0.146766538 | 1.34E−05 | — | HMDB 36832 | Sterebin D__C18H30O3 |
| Neg__293__28 | C18H30O3 | 0.146766538 | 1.34E−05 | — | HMDB 10220 | 9(10)-EpODE__C18H30O3 |
| Neg__293__28 | C18H30O3 | 0.146766538 | 1.34E−05 | — | HMDB 04668 | 13-OxoODE__C18H30O3 |
| Neg__293__28 | C18H30O3 | 0.146766538 | 1.34E−05 | — | HMDB 04669 | 9-OxoODE__C18H30O3 |
| Neg__293__28 | C18H30O3 | 0.146766538 | 1.34E−05 | — | HMDB 31934 | (9S,10E,12Z,15Z)-9-Hydroxy-10,12,15-octadecatrienoic acid__C18H30O3 |
| Neg__293__28 | C18H30O3 | 0.146766538 | 1.34E−05 | — | HMDB 29786 | 10-Oxo-11-octadecen-13-olide__C18H30O3 |
| Neg__293__28 | C18H30O3 | 0.146766538 | 1.34E−05 | — | HMDB 39603 | 3,4-Dimethyl-5-pentyl-2-furanheptanoic acid__C18H30O3 |
| Neg__293__28 | C18H30O3 | 0.146766538 | 1.34E−05 | — | HMDB 11108 | 17-Hydroxylinolenic acid__C18H30O3 |
| Neg__299__10 | C16H12O6 | 6.631095704 | 1.02E−05 | — | HMDB 37441 | Kaempferide__C16H12O6 |
| Neg__299__10 | C16H12O6 | 6.631095704 | 1.02E−05 | — | HMDB 33720 | 6alpha-Hydroxymaackiain__C16H12O6 |
| Neg__299__10 | C16H12O6 | 6.631095704 | 1.02E−05 | — | HMDB 32695 | Barpisoflavone A__C16H12O6 |
| Neg__299__10 | C16H12O6 | 6.631095704 | 1.02E−05 | — | HMDB 32696 | Cajanin__C16H12O6 |
| Neg__299__10 | C16H12O6 | 6.631095704 | 1.02E−05 | — | HMDB 29676 | Diosmetin__C16H12O6 |
| Neg__299__10 | C16H12O6 | 6.631095704 | 1.02E−05 | — | HMDB 30617 | Pratensein__C16H12O6 |
| Neg__299__10 | C16H12O6 | 6.631095704 | 1.02E−05 | — | HMDB 34443 | Questinol__C16H12O6 |
| Neg__299__10 | C16H12O6 | 6.631095704 | 1.02E−05 | — | HMDB 33321 | 3,5-Dihydroxy-6,7-methylenedioxy-flavanone__C16H12O6 |
| Neg__299__10 | C16H12O6 | 6.631095704 | 1.02E−05 | — | HMDB 30667 | Chrysoeriol__C16H12O6 |
| Neg__299__10 | C16H12O6 | 6.631095704 | 1.02E−05 | — | HMDB 37339 | Luteolin 7-methyl ether__C16H12O6 |

TABLE 3-continued

| Feature (mode_m/z_RT) | Formula | Q7/Q111 | pval | Recon_ID | HMDB_ID | Name_Formula |
|---|---|---|---|---|---|---|
| Neg_299_10 | C16H12O6 | 6.631095704 | 1.02E−05 | — | HMDB 29492 | 3,3',7-Trihydroxy-4'-methoxyflavone_C16H12O6 |
| Neg_299_10 | C16H12O6 | 6.631095704 | 1.02E−05 | — | HMDB 30659 | Takakin_C16H12O6 |
| Neg_299_10 | C16H12O6 | 6.631095704 | 1.02E−05 | — | HMDB 42024 | tectorigenin_C16H12O6 |
| Neg_299_10 | C16H12O6 | 6.631095704 | 1.02E−05 | — | HMDB 33760 | Santal_C16H12O6 |
| Neg_315_46 | C19H40O3 | 0.264819743 | 8.25E−05 | — | HMDB 32112 | 1,2,4-Nonadecanetriol_C19H40O3 |
| Neg_436_36 | C21H44NO6P | 3.258424486 | 0.000576921 | — | HMDB 11152 | PE(P-16:0e/0:0)_C21H44NO6P |
| Neg_537_51 | C34H67NO3 | 9.456312887 | 0.00449825 | — | HMDB 04949 | Ceramide (d18:1/16:0)_C34H67NO3 |
| Neg_537_51 | C34H67NO3 | 9.456312887 | 0.00449825 | — | HMDB 00790 | N-Palmitoylsphingosine_C34H67NO3 |
| Neg_315_45 | C19H40O3 | 0.218072147 | 0.0001 | — | HMDB 32112 | 1,2,4-Nonadecanetriol_C19H40O3 |
| Neg_699_49 | C40H77NO8 | 0.385532809 | 0.00E+00 | — | HMDB 10708 | Galactosylceramide (d18:1/16:0)_C40H77NO8 |
| Neg_699_49 | C40H77NO8 | 0.385532809 | 0.00E+00 | — | HMDB 04971 | Glucosylceramide (d18:1/16:0)_C40H77NO8 |
| Neg_746_40 | C40H75O10P | 3.938084903 | 2.00E−04 | — | HMDB 10631 | PG(18:1(9Z)/16:1(9Z))_C40H75O10P |
| Neg_746_40 | C40H75O10P | 3.938084903 | 2.00E−04 | — | HMDB 10645 | PG(18:2(9Z,12Z)/16:0)_C40H75O10P |
| Neg_746_40 | C40H75O10P | 3.938084903 | 2.00E−04 | — | HMDB 10616 | PG(18:1(11Z)/16:1(9Z))_C40H75O10P |
| Neg_746_40 | C40H75O10P | 3.938084903 | 0.0002 | — | HMDB 10588 | PG(16:1(9Z)/18:1(11Z))_C40H75O10P |
| Neg_746_40 | C40H75O10P | 3.938084903 | 0.0002 | — | HMDB 10589 | PG(16:1(9Z)/18:1(9Z))_C40H75O10P |
| Neg_746_40 | C40H75O10P | 3.938084903 | 0.0002 | — | HMDB 10575 | PG(16:0/18:2(9Z,12Z))_C40H75O10P |
| Neg_772_41 | C42H77O10P | 2.803914055 | 1.10E−03 | — | HMDB 10649 | PG(18:2(9Z,12Z)/18:1(9Z))_C42H77O10P |
| Neg_772_41 | C42H77O10P | 2.803914055 | 1.10E−03 | — | HMDB 10648 | PG(18:2(9Z,12Z)/18:1(11Z))_C42H77O10P |
| Neg_772_41 | C42H77O10P | 2.803914055 | 1.10E−03 | — | HMDB 10635 | PG(18:1(9Z)/18:2(9Z,12Z))_C42H77O10P |
| Neg_772_41 | C42H77O10P | 2.803914055 | 1.10E−03 | — | HMDB 10620 | PG(18:1(11Z)/18:2(9Z,12Z))_C42H77O10P |
| Neg_772_41 | C42H77O10P | 2.803914055 | 1.10E−03 | — | HMDB 10677 | PG(18:3(9Z,12Z,15Z)/18:0)_C42H77O10P |
| Neg_772_41 | C42H77O10P | 2.803914055 | 1.10E−03 | — | HMDB 10607 | PG(18:0/18:3(9Z,12Z,15Z))_C42H77O10P |
| Neg_772_41 | C42H77O10P | 2.803914055 | 1.10E−03 | — | HMDB 10606 | PG(18:0/18:3(6Z,9Z,12Z))_C42H77O10P |
| Neg_772_41 | C42H77O10P | 2.803914055 | 1.10E−03 | — | HMDB 10662 | PG(18:3(6Z,9Z,12Z)/18:0)_C42H77O10P |
| Neg_772_41 | C42H77O10P | 2.803914055 | 1.10E−03 | — | HMDB 10579 | PG(16:0/20:3(8Z,11Z,14Z))_C42H77O10P |
| Neg_772_41 | C42H77O10P | 2.803914055 | 1.10E−03 | — | HMDB 10578 | PG(16:0/20:3(5Z,8Z,11Z))_C42H77O10P |
| Neg_774_42 | C42H79O10P | 6.207754878 | 0.0007 | — | HMDB 10633 | PG(18:1(9Z)/18:1(11Z))_C42H79O10P |
| Neg_774_42 | C42H79O10P | 6.207754878 | 0.0007 | — | HMDB 10647 | PG(18:2(9Z,12Z)/18:0)_C42H79O10P |
| Neg_774_42 | C42H79O10P | 6.207754878 | 0.0007 | — | HMDB 10618 | PG(18:1(11Z)/18:1(11Z))_C42H79O10P |
| Neg_774_42 | C42H79O10P | 6.207754878 | 0.0007 | — | HMDB 10619 | PG(18:1(11Z)/18:1(9Z))_C42H79O10P |
| Neg_774_42 | C42H79O10P | 6.207754878 | 0.0007 | — | HMDB 10634 | PG(18:1(9Z)/18:1(9Z))_C42H79O10P |
| Neg_774_42 | C42H79O10P | 6.207754878 | 0.0007 | — | HMDB 10605 | PG(18:0/18:2(9Z,12Z))_C42H79O10P |
| Neg_791_40 | C44H73O10P | 3.498249062 | 0.00E+00 | — | HMDB 10670 | PG(18:3(6Z,9Z,12Z)/20:4(5Z,8Z,11Z,14Z))_C44H73O10P |
| Neg_791_40 | C44H73O10P | 3.498249062 | 0.00E+00 | — | HMDB 10685 | PG(18:3(9Z,12Z,15Z)/20:4(5Z,8Z,11Z,14Z))_C44H73O10P |
| Neg_791_40 | C44H73O10P | 3.498249062 | 0.00E+00 | — | HMDB 10599 | PG(16:1(9Z)/22:6(4Z,7Z,10Z,13Z,16Z,19Z))_C44H73O10P |

TABLE 3-continued

| Feature (mode_m/z_RT) | Formula | Q7/Q111 | pval | Recon_ID | HMDB_ID | Name_Formula |
|---|---|---|---|---|---|---|
| Neg_820_41 | C46H77O10P | 6.268595777 | 0.001 | — | HMDB 10644 | PG(18:1(9Z)/22:6(4Z,7Z,10Z,13Z,16Z,19Z))_C46H77O10P |
| Neg_820_41 | C46H77O10P | 6.268595777 | 0.001 | — | HMDB 10629 | PG(18:1(11Z)/22:6(4Z,7Z,10Z,13Z,16Z,19Z))_C46H77O10P |
| Neg_820_41 | C46H77O10P | 6.268595777 | 0.001 | — | HMDB 10671 | PG(18:3(6Z,9Z,12Z)/22:4(7Z,10Z,13Z,16Z))_C46H77O10P |
| Neg_820_41 | C46H77O10P | 6.268595777 | 0.001 | — | HMDB 10686 | PG(18:3(9Z,12Z,15Z)/22:4(7Z,10Z,13Z,16Z))_C46H77O10P |
| Neg_820_41 | C46H77O10P | 6.268595777 | 0.001 | — | HMDB 10657 | PG(18:2(9Z,12Z)/22:5(4Z,7Z,10Z,13Z,16Z))_C46H77O10P |
| Neg_820_41 | C46H77O10P | 6.268595777 | 0.001 | — | HMDB 10658 | PG(18:2(9Z,12Z)/22:5(7Z,10Z,13Z,16Z,19Z))_C46H77O10P |
| Pos_626_34 | C36H48O8 | 6.894259789 | 0.008338023 | — | HMDB 41368 | 24-Acetyl-25-cinnamoylvulgaroside_C36H48O8 |
| Pos_649_44 | C42H81NO3 | 7.952443501 | 0.000187956 | — | HMDB 04953 | Cer(d18:1/24:1(15Z))_C42H81NO3 |
| Pos_651_45 | C42H83NO3 | 9.407155158 | 5.56E−05 | — | HMDB 00831 | N-Lignoceroylsphingosine_C42H83NO3 |
| Pos_651_45 | C42H83NO3 | 9.407155158 | 5.56E−05 | — | HMDB 11769 | Cer(d18:0/24:1(15Z))_C42H83NO3 |
| Pos_651_45 | C42H83NO3 | 9.407155158 | 5.56E−05 | — | HMDB 04956 | Ceramide (d18:1/24:0)_C42H83NO3 |
| Pos_671_44 | C44H76O3 | 5.920113197 | 4.59E−07 | — | HMDB 34841 | Faradiol myristate_C44H76O3 |
| Pos_773_43 | C44H86NO7P | 5.379732942 | 1.21E−06 | — | HMDB 11242 | PC(P-18:0/18:1(11Z))_C44H86NO7P |
| Pos_773_43 | C44H86NO7P | 5.379732942 | 1.21E−06 | — | HMDB 11243 | PC(P-18:0/18:1(9Z))_C44H86NO7P |
| Pos_773_43 | C44H86NO7P | 5.379732942 | 1.21E−06 | — | HMDB 08062 | PC(18:0/P-18:1(11Z))_C44H86NO7P |
| Pos_773_43 | C44H86NO7P | 5.379732942 | 1.21E−06 | — | HMDB 08063 | PC(18:0/P-18:1(9Z))_C44H86NO7P |
| Pos_773_43 | C44H86NO7P | 5.379732942 | 1.21E−06 | — | HMDB 08094 | PC(18:1(11Z)/P-18:0)_C44H86NO7P |
| Pos_773_43 | C44H86NO7P | 5.379732942 | 1.21E−06 | — | HMDB 11274 | PC(P-18:1(11Z)/18:0)_C44H86NO7P |
| Pos_773_43 | C44H86NO7P | 5.379732942 | 1.21E−06 | — | HMDB 11307 | PC(P-18:1(9Z)/18:0)_C44H86NO7P |
| Pos_773_43 | C44H86NO7P | 5.379732942 | 1.21E−06 | — | HMDB 13428 | PC(o-18:1(9Z)/18:1(11Z))_C44H86NO7P |
| Pos_773_43 | C44H86NO7P | 5.379732942 | 1.21E−06 | — | HMDB 08324 | PC(20:1(11Z)/P-16:0)_C44H86NO7P |
| Pos_773_43 | C44H86NO7P | 5.379732942 | 1.21E−06 | — | HMDB 13418 | PC(o-18:0/18:2(9Z,12Z))_C44H86NO7P |
| Pos_773_43 | C44H86NO7P | 5.379732942 | 1.21E−06 | — | HMDB 11216 | PC(P-16:0/20:1(11Z))_C44H86NO7P |
| Pos_773_43 | C44H86NO7P | 5.379732942 | 1.21E−06 | — | HMDB 08127 | PC(18:1(9Z)/P-18:0)_C44H86NO7P |
| Pos_200_28 | C12H22O | 7.423652727 | 0 | — | HMDB 32279 | 2-Ethyl-1,3,3-trimethyl-2-norbornanol_C12H22O |
| Pos_200_28 | C12H22O | 7.423652727 | 0 | — | HMDB 31341 | Cyclododecanone_C12H22O |
| Pos_200_28 | C12H22O | 7.423652727 | 0 | — | HMDB 36461 | Geosmin_C12H22O |
| Pos_200_28 | C12H22O | 7.423652727 | 0 | — | HMDB 31102 | (Z,Z)-3,6-Dodecadien-1-ol_C12H22O |
| Pos_200_28 | C12H22O | 7.423652727 | 0 | — | HMDB 31020 | 2-Dodecenal_C12H22O |
| Pos_200_28 | C12H22O | 7.423652727 | 0 | — | HMDB 38972 | (E)-2-Butyl-2-octenal_C12H22O |
| Pos_200_28 | C12H22O | 7.423652727 | 0 | — | HMDB 32542 | trans- and cis-2,4,8-Trimethyl-3,7-nona-dien-2-ol_C12H22O |
| Pos_415_35 | C47H93N2O7P | 0 | 0 | — | HMDB 13469 | SM(d18:0/24:1(15Z)(OH))_C47H93N2O7P |
| Pos_679_40 | C36H72NO8P | 0.194226062 | 1.20E−03 | — | HMDB 07866 | PC(14:0/14:0)_C36H72NO8P |
| Pos_679_40 | C36H72NO8P | 0.194226062 | 1.20E−03 | — | HMDB 08922 | PE(16:0/15:0)_C36H72NO8P |

TABLE 3-continued

| Feature (mode__m/z__RT) | Formula | Q7/Q111 | pval | Recon_ID | HMDB_ID | Name__Formula |
|---|---|---|---|---|---|---|
| Pos__679__40 | C36H72NO8P | 0.194226062 | 1.20E−03 | — | HMDB 08890 | PE(15:0/16:0)__C36H72NO8P |
| Pos__679__40 | C43H64O5 | 0.194226062 | 1.20E−03 | — | HMDB 07353 | DG(18:4(6Z,9Z,12Z,15Z)/22:6(4Z,7Z,10Z,13Z,16Z,19Z)/0:0)__C43H64O5 |
| Pos__679__40 | C43H64O5 | 0.194226062 | 1.20E−03 | — | HMDB 56376 | DG(18:4n3/0:0/22:6n3)__C43H64O5 |
| Pos__679__40 | C43H64O5 | 0.194226062 | 1.20E−03 | — | HMDB 07578 | DG(20:5(5Z,8Z,11Z,14Z,17Z)/20:5(5Z,8Z,11Z,14Z,17Z)/0:0)__C43H64O5 |
| Pos__679__40 | C43H64O5 | 0.194226062 | 1.20E−03 | — | HMDB 56381 | DG(20:5n3/0:0/20:5n3)__C43H64O5 |
| Pos__679__40 | C43H64O5 | 0.194226062 | 1.20E−03 | — | HMDB 07773 | DG(22:6(4Z,7Z,10Z,13Z,16Z,19Z)/18:4(6Z,9Z,12Z,15Z)/0:0)__C43H64O5 |
| Pos__837__48 | C53H102O5 | 5.301022129 | 0 | — | HMDB 44080 | TG(16:0/16:1(9Z)/o-18:0)__C53H102O5 |
| Pos__837__48 | C53H102O5 | 5.301022129 | 0 | — | HMDB 45455 | TG(18:0/o-18:0/14:1(9Z))__C53H102O5 |
| Pos__837__48 | C53H102O5 | 5.301022129 | 0 | — | HMDB 48478 | TG(16:1(9Z)/16:0/o-18:0)__C53H102O5 |
| Pos__837__48 | C53H102O5 | 5.301022129 | 0 | — | HMDB 42941 | TG(14:0/o-18:0/18:1(9Z))__C53H102O5 |
| Pos__837__48 | C53H102O5 | 5.301022129 | 0 | — | HMDB 42940 | TG(14:0/o-18:0/18:1(11Z))__C53H102O5 |
| Pos__837__48 | C53H102O5 | 5.301022129 | 0 | — | HMDB 49720 | TG(18:1(9Z)/14:0/o-18:0)__C53H102O5 |
| Pos__837__48 | C53H102O5 | 5.301022129 | 0 | — | HMDB 49092 | TG(18:1(11Z)/14:0/o-18:0)__C53H102O5 |
| Pos__837__48 | C53H102O5 | 5.301022129 | 0 | — | HMDB 44883 | TG(18:0/14:1(9Z)/o-18:0)__C53H102O5 |
| Pos__837__48 | C53H102O5 | 5.301022129 | 0 | — | HMDB 42390 | TG(14:0/18:1(9Z)/o-18:0)__C53H102O5 |
| Pos__837__48 | C53H102O5 | 5.301022129 | 0 | — | HMDB 47815 | TG(14:1(9Z)/18:0/o-18:0)__C53H102O5 |
| Pos__837__48 | C53H102O5 | 5.301022129 | 0 | — | HMDB 44647 | TG(16:0/o-18:0/16:1(9Z))__C53H102O5 |
| Pos__837__48 | C53H102O5 | 5.301022129 | 0 | — | HMDB 42360 | TG(14:0/18:1(11Z)/o-18:0)__C53H102O5 |
| Pos__863__48 | C55H104O5 | 7.055438647 | 0 | — | HMDB 53289 | TG(20:2n6/15:0/o-18:0)__C55H104O5 |
| Pos__863__48 | C55H104O5 | 7.055438647 | 0 | — | HMDB 43817 | TG(15:0/o-18:0/20:2n6)__C55H104O5 |
| Pos__863__48 | C55H104O5 | 7.055438647 | 0 | — | HMDB 49052 | TG(16:1(9Z)/o-18:0/18:1(11Z))__C55H104O5 |
| Pos__863__48 | C55H104O5 | 7.055438647 | 0 | — | HMDB 49053 | TG(16:1(9Z)/o-18:0/18:1(9Z))__C55H104O5 |
| Pos__863__48 | C55H104O5 | 7.055438647 | 0 | — | HMDB 49260 | TG(18:1(11Z)/16:1(9Z)/o-18:0)__C55H104O5 |
| Pos__863__48 | C55H104O5 | 7.055438647 | 0 | — | HMDB 50451 | TG(20:1(11Z)/14:1(9Z)/o-18:0)__C55H104O5 |
| Pos__863__48 | C55H104O5 | 7.055438647 | 0 | — | HMDB 43481 | TG(15:0/20:2n6/o-18:0)__C55H104O5 |
| Pos__863__48 | C55H104O5 | 7.055438647 | 0.00E+00 | — | HMDB 52425 | TG(18:2(9Z,12Z)/15:0/o-18:0)__C55H104O5 |
| Pos__863__48 | C55H104O5 | 7.055438647 | 0 | — | HMDB 48395 | TG(14:1(9Z)/o-18:0/20:1(11Z))__C55H104O5 |
| Pos__863__48 | C55H104O5 | 7.055438647 | 0 | — | HMDB 43815 | TG(15:0/o-18:0/18:2(9Z,12Z))__C55H104O5 |
| Pos__863__48 | C55H104O5 | 7.055438647 | 0 | — | HMDB 47999 | TG(14:1(9Z)/20:1(11Z)/o-18:0)__C55H104O5 |
| Pos__863__48 | C55H104O5 | 7.055438647 | 0 | — | HMDB 43423 | TG(15:0/18:2(9Z,12Z)/o-18:0)__C55H104O5 |
| Pos__863__48 | C55H104O5 | 7.055438647 | 0 | — | HMDB 49880 | TG(18:1(9Z)/16:1(9Z)/o-18:0)__C55H104O5 |
| Pos__863__48 | C55H104O5 | 7.055438647 | 0 | — | HMDB 48632 | TG(16:1(9Z)/18:1(11Z)/o-18:0)__C55H104O5 |
| Pos__863__48 | C55H104O5 | 7.055438647 | 0 | — | HMDB 48654 | TG(16:1(9Z)/18:1(9Z)/o-18:0)__C55H104O5 |
| Pos__889__48 | C57H106O5 | 5.645901483 | 0 | — | HMDB 54420 | TG(22:2(13Z,16Z)/14:1(9Z)/o-18:0)__C57H106O5 |
| Pos__889__48 | C57H106O5 | 5.645901483 | 0 | — | HMDB 45471 | TG(18:0/o-18:0/18:3(9Z,12Z,15Z))__C57H106O5 |
| Pos__889__48 | C57H106O5 | 5.645901483 | 0 | — | HMDB 44651 | TG(16:0/o-18:0/20:3(5Z,8Z,11Z))__C57H106O5 |

TABLE 3-continued

| Feature (mode_m/z_RT) | Formula | Q7/Q111 | pval | Recon_ID | HMDB_ID | Name_Formula |
|---|---|---|---|---|---|---|
| Pos_889_48 | C57H106O5 | 5.645901483 | 0 | — | HMDB 44657 | TG(16:0/o-18:0/20:3n6)_C57H106O5 |
| Pos_889_48 | C57H106O5 | 5.645901483 | 0 | — | HMDB 50922 | TG(20:3(5Z,8Z,11Z)/16:0/o-18:0)_C57H106O5 |
| Pos_889_48 | C57H106O5 | 5.645901483 | 0 | — | HMDB 52900 | TG(18:3(6Z,9Z,12Z)/18:0/o-18:0)_C57H106O5 |
| Pos_889_48 | C57H106O5 | 5.645901483 | 0 | — | HMDB 53688 | TG(20:3n6/16:0/o-18:0)_C57H106O5 |
| Pos_889_48 | C57H106O5 | 5.645901483 | 0 | — | HMDB 44192 | TG(16:0/20:3(5Z,8Z,11Z)/o-18:0)_C57H106O5 |
| Pos_889_48 | C57H106O5 | 5.645901483 | 0 | — | HMDB 45464 | TG(18:0/o-18:0/18:3(6Z,9Z,12Z))_C57H106O5 |
| Pos_889_48 | C57H106O5 | 5.645901483 | 0 | — | HMDB 48206 | TG(14:1(9Z)/22:2(13Z,16Z)/o-18:0)_C57H106O5 |
| Pos_889_48 | C57H106O5 | 5.645901483 | 0 | — | HMDB 44360 | TG(16:0/20:3n6/o-18:0)_C57H106O5 |
| Pos_889_48 | C57H106O5 | 5.645901483 | 0 | — | HMDB 48404 | TG(14:1(9Z)/o-18:0/22:2(13Z,16Z))_C57H106O5 |
| Pos_889_48 | C57H106O5 | 5.645901483 | 0 | — | HMDB 45315 | TG(18:0/18:3(9Z,12Z,15Z)/o-18:0)_C57H106O5 |
| Pos_889_48 | C57H106O5 | 5.645901483 | 0 | — | HMDB 45126 | TG(18:0/18:3(6Z,9Z,12Z)/o-18:0)_C57H106O5 |
| Pos_889_48 | C57H106O5 | 5.645901483 | 0 | — | HMDB 55175 | TG(18:3(9Z,12Z,15Z)/18:0/o-18:0)_C57H106O5 |
| Pos_893_48 | C57H110O5 | 10.05427004 | 0 | — | HMDB 46235 | TG(20:0/o-18:0/16:1(9Z))_C57H110O5 |
| Pos_893_48 | C57H110O5 | 10.05427004 | 0 | — | HMDB 44650 | TG(16:0/o-18:0/20:1(11Z))_C57H110O5 |
| Pos_893_48 | C57H110O5 | 10.05427004 | 0 | — | HMDB 44964 | TG(18:0/18:1(9Z)/o-18:0)_C57H110O5 |
| Pos_893_48 | C57H110O5 | 10.05427004 | 0 | — | HMDB 49155 | TG(18:1(11Z)/18:0/o-18:0)_C57H110O5 |
| Pos_893_48 | C57H110O5 | 10.05427004 | 0 | — | HMDB 45710 | TG(20:0/16:1(9Z)/o-18:0)_C57H110O5 |
| Pos_893_48 | C57H110O5 | 10.05427004 | 0.00E+00 | — | HMDB 45457 | TG(18:0/o-18:0/18:1(11Z))_C57H110O5 |
| Pos_893_48 | C57H110O5 | 10.05427004 | 0.00E+00 | — | HMDB 45458 | TG(18:0/o-18:0/18:1(9Z))_C57H110O5 |
| Pos_893_48 | C57H110O5 | 10.05427004 | 0.00E+00 | — | HMDB 44937 | TG(18:0/18:1(11Z)/o-18:0)_C57H110O5 |
| Pos_893_48 | C57H110O5 | 10.05427004 | 0.00E+00 | — | HMDB 42944 | TG(14:0/o-18:0/22:1(13Z))_C57H110O5 |
| Pos_893_48 | C57H110O5 | 10.05427004 | 0 | — | HMDB 44164 | TG(16:0/20:1(11Z)/o-18:0)_C57H110O5 |
| Pos_893_48 | C57H110O5 | 10.05427004 | 0 | — | HMDB 46455 | TG(22:0/14:1(9Z)/o-18:0)_C57H110O5 |
| Pos_893_48 | C57H110O5 | 10.05427004 | 0 | — | HMDB 46983 | TG(22:0/o-18:0/14:1(9Z))_C57H110O5 |
| Pos_893_48 | C57H110O5 | 10.05427004 | 0.00E+00 | — | HMDB 48522 | TG(16:1(9Z)/20:0/o-18:0)_C57H110O5 |
| Pos_893_48 | C57H110O5 | 10.05427004 | 0.00E+00 | — | HMDB 50356 | TG(20:1(11Z)/16:0/o-18:0)_C57H110O5 |
| Pos_893_48 | C57H110O5 | 10.05427004 | 0.00E+00 | — | HMDB 51424 | TG(22:1(13Z)/14:0/o-18:0)_C57H110O5 |
| Pos_893_48 | C57H110O5 | 10.05427004 | 0.00E+00 | — | HMDB 42480 | TG(14:0/22:1(13Z)/o-18:0)_C57H110O5 |
| Pos_893_48 | C57H110O5 | 10.05427004 | 0.00E+00 | — | HMDB 47861 | TG(14:1(9Z)/22:0/o-18:0)_C57H110O5 |
| Pos_893_48 | C57H110O5 | 10.05427004 | 0.00E+00 | — | HMDB 49780 | TG(18:1(9Z)/18:0/o-18:0)_C57H110O5 |
| Pos_907_48 | C57H108O6 | 6.573506156 | 0 | — | HMDB 47054 | TG(24:0/16:0/14:1(9Z))_C57H108O6 |
| Pos_907_48 | C57H108O6 | 6.573506156 | 0 | — | HMDB 44083 | TG(16:0/18:1(11Z)/20:0)_C57H108O6 |
| Pos_907_48 | C57H108O6 | 6.573506156 | 0 | — | HMDB 05395 | TG(18:0/18:0/18:1(9Z))[iso3]_C57H108O6 |
| Pos_907_48 | C57H108O6 | 6.573506156 | 0 | — | HMDB 44911 | TG(18:0/18:1(11Z)/18:0)_C57H108O6 |
| Pos_907_48 | C57H108O6 | 6.573506156 | 0 | — | HMDB 42220 | TG(14:0/22:0/18:1(11Z))_C57H108O6 |
| Pos_907_48 | C57H108O6 | 6.573506156 | 0 | — | HMDB 45484 | TG(20:0/14:0/20:1(11Z))_C57H108O6 |
| Pos_907_48 | C57H108O6 | 6.573506156 | 0 | — | HMDB 43002 | TG(15:0/15:0/24:1(15Z))_C57H108O6 |
| Pos_907_48 | C57H108O6 | 6.573506156 | 0 | — | HMDB 46260 | TG(22:0/14:0/18:1(11Z))_C57H108O6 |

TABLE 3-continued

| Feature (mode_m/z_RT) | Formula | Q7/Q111 | pval | Recon_ID | HMDB_ID | Name_Formula |
|---|---|---|---|---|---|---|
| Pos_907_48 | C57H108O6 | 6.573506156 | 0 | — | HMDB 46261 | TG(22:0/14:0/18:1(9Z))_C57H108O6 |
| Pos_907_48 | C57H108O6 | 6.573506156 | 0 | — | HMDB 44938 | TG(18:0/18:1(9Z)/18:0)_C57H108O6 |
| Pos_907_48 | C57H108O6 | 6.573506156 | 0 | — | HMDB 42192 | TG(14:0/20:0/20:1(11Z))_C57H108O6 |
| Pos_907_48 | C57H108O6 | 6.573506156 | 0 | — | HMDB 44002 | TG(16:0/24:0/14:1(9Z))_C57H108O6 |
| Pos_907_48 | C57H108O6 | 6.573506156 | 0 | — | HMDB 44193 | TG(16:0/22:1(13Z)/16:0)_C57H108O6 |
| Pos_907_48 | C57H108O6 | 6.573506156 | 0 | — | HMDB 45559 | TG(20:0/18:0/16:1(9Z))_C57H108O6 |
| Pos_907_48 | C57H108O6 | 6.573506156 | 0 | — | HMDB 44730 | TG(18:0/16:0/20:1(11Z))_C57H108O6 |
| Pos_907_48 | C57H108O6 | 6.573506156 | 0 | — | HMDB 43975 | TG(16:0/22:0/16:1(9Z))_C57H108O6 |
| Pos_907_48 | C57H108O6 | 6.573506156 | 0 | — | HMDB 30970 | Glycerol 1,3-dioctadecanoate 2-(9Z-octadecenoate)_C57H108O6 |
| Pos_907_48 | C57H108O6 | 6.573506156 | 0 | — | HMDB 44678 | TG(18:0/14:0/22:1(13Z))_C57H108O6 |
| Pos_907_48 | C57H108O6 | 6.573506156 | 0 | — | HMDB 45584 | TG(20:0/20:0/14:1(9Z))_C57H108O6 |
| Pos_907_48 | C57H108O6 | 6.573506156 | 0 | — | HMDB 42164 | TG(14:0/18:0/22:1(13Z))_C57H108O6 |
| Pos_907_48 | C57H108O6 | 6.573506156 | 0 | — | HMDB 43896 | TG(16:0/16:0/22:1(13Z))_C57H108O6 |
| Pos_907_48 | C57H108O6 | 6.573506156 | 0 | — | HMDB 42135 | TG(14:0/16:0/24:1(15Z))_C57H108O6 |
| Pos_907_48 | C57H108O6 | 6.573506156 | 0 | — | HMDB 46333 | TG(22:0/18:0/14:1(9Z))_C57H108O6 |
| Pos_907_48 | C57H108O6 | 6.573506156 | 0 | — | HMDB 44138 | TG(16:0/20:1(11Z)/18:0)_C57H108O6 |
| Pos_907_48 | C57H108O6 | 6.573506156 | 0 | — | HMDB 05381 | TG(16:0/18:1(9Z)/20:0)[iso6]_C57H108O6 |
| Pos_907_48 | C57H108O6 | 6.573506156 | 0 | — | HMDB 05368 | TG(16:0/18:0/20:1(11Z))[iso6]_C57H108O6 |
| Pos_907_48 | C57H108O6 | 6.573506156 | 0 | — | HMDB 42454 | TG(14:0/22:1(13Z)/18:0)_C57H108O6 |
| Pos_907_48 | C57H108O6 | 6.573506156 | 0 | — | HMDB 45659 | TG(20:0/14:1(9Z)/20:0)_C57H108O6 |
| Pos_907_48 | C57H108O6 | 6.573506156 | 0 | — | HMDB 46309 | TG(22:0/16:0/16:1(9Z))_C57H108O6 |
| Pos_907_48 | C57H108O6 | 6.573506156 | 0 | — | HMDB 44807 | TG(18:0/22:0/14:1(9Z))_C57H108O6 |
| Pos_907_48 | C57H108O6 | 6.573506156 | 0 | — | HMDB 44859 | TG(18:0/14:1(9Z)/22:0)_C57H108O6 |
| Pos_907_48 | C57H108O6 | 6.573506156 | 0 | — | HMDB 45535 | TG(20:0/16:0/18:1(9Z))_C57H108O6 |
| Pos_907_48 | C57H108O6 | 6.573506156 | 0 | — | HMDB 45534 | TG(20:0/16:0/18:1(11Z))_C57H108O6 |
| Pos_907_48 | C57H108O6 | 6.573506156 | 0 | — | HMDB 44885 | TG(18:0/16:1(9Z)/20:0)_C57H108O6 |
| Pos_907_48 | C57H108O6 | 6.573506156 | 0 | — | HMDB 42395 | TG(14:0/20:1(11Z)/20:0)_C57H108O6 |
| Pos_907_48 | C57H108O6 | 6.573506156 | 0 | — | HMDB 42307 | TG(14:0/16:1(9Z)/24:0)_C57H108O6 |
| Pos_907_48 | C57H108O6 | 6.573506156 | 0 | — | HMDB 43948 | TG(16:0/20:0/18:1(11Z))_C57H108O6 |
| Pos_907_48 | C57H108O6 | 6.573506156 | 0 | — | HMDB 43949 | TG(16:0/20:0/18:1(9Z))_C57H108O6 |
| Pos_907_48 | C57H108O6 | 6.573506156 | 0 | — | HMDB 44029 | TG(16:0/14:1(9Z)/24:0)_C57H108O6 |
| Pos_907_48 | C57H108O6 | 6.573506156 | 0 | — | HMDB 34386 | Glycerol 1,2-dioctadecanoate 3-(9Z-octadecenoate)_C57H108O6 |
| Pos_907_48 | C57H108O6 | 6.573506156 | 0 | — | HMDB 42483 | TG(14:0/24:1(15Z)/16:0)_C57H108O6 |
| Pos_907_48 | C57H108O6 | 6.573506156 | 0.00E+00 | — | HMDB 42366 | TG(14:0/18:1(9Z)/22:0)_C57H108O6 |
| Pos_907_48 | C57H108O6 | 6.573506156 | 0.00E+00 | — | HMDB 10433 | TG(18:0/18:0/18:1(11Z))[iso3]_C57H108O6 |
| Pos_907_48 | C57H108O6 | 6.573506156 | 0.00E+00 | — | HMDB 47007 | TG(24:0/14:0/16:1(9Z))_C57H108O6 |
| Pos_907_48 | C57H108O6 | 6.573506156 | 0.00E+00 | — | HMDB 42249 | TG(14:0/24:0/16:1(9Z))_C57H108O6 |

TABLE 3-continued

| Feature (mode_m/z_RT) | Formula | Q7/Q111 | pval | Recon_ID | HMDB_ID | Name_Formula |
|---|---|---|---|---|---|---|
| Pos_907_48 | C57H108O6 | 6.573506156 | 0.00E+00 | — | HMDB 43366 | TG(15:0/24:1(15Z)/15:0)_C57H108O6 |
| Pos_907_48 | C57H108O6 | 6.573506156 | 0.00E+00 | — | HMDB 42221 | TG(14:0/22:0/18:1(9Z))_C57H108O6 |
| Pos_907_48 | C57H108O6 | 6.573506156 | 0.00E+00 | — | HMDB 44056 | TG(16:0/16:1(9Z)/22:0)_C57H108O6 |
| Pos_907_48 | C57H108O6 | 6.573506156 | 0.00E+00 | — | HMDB 05422 | TG(16:1(9Z)/18:0/20:0)[iso6]_C57H108O6 |
| Pos_907_48 | C57H108O6 | 6.573506156 | 0.00E+00 | — | HMDB 44781 | TG(18:0/20:0/16:1(9Z))_C57H108O6 |
| Pos_907_48 | C57H108O6 | 6.573506156 | 0.00E+00 | — | HMDB 43841 | TG(16:0/14:0/24:1(15Z))_C57H108O6 |
| Pos_907_48 | C57H108O6 | 6.573506156 | 0.00E+00 | — | HMDB 42336 | TG(14:0/18:1(11Z)/22:0)_C57H108O6 |

Verification of Altered Metabolites Using STHdh Cell Line Model of HD

Altered metabolites inferred by a PIUMet algorithm were confirmed using two reverse-phase LC methods and MS data acquired in positive and negative ionization modes using two LCMS systems including a Nexera X2 U-HPLC system (available from Shimadzu Scientific Instruments, Columbia, Md.) and either a Q Exactive™ Hybrid Quadrupole-Orbitrap Mass Spectrometer or an Exactive™ Plus Orbitrap Mass Spectrometer (both available from Thermo Fisher Scientific, Waltham, Mass.) according to some embodiments.

For the measurement of lipids, LC-MS samples were extracted from cell pellets (3×107 cells) in isopropanol containing 1-dodecanoyl-2-tridecanoyl-sn-glycerol-3-phosphocholine as an internal standard (available from Avanti Polar Lipids, Alabaster, Ala.). Extracted metabolites were injected into an ACQUITY UPLC BEH C8 column (available from Waters Corp., Milford, Mass.) (1.7 μm), eluted isocratically for 1 minute at 80% mobile phase A (95:5:0.1 vol/vol/vol 10 mM ammonium acetate/methanol/acetic acid), followed by a 2-minute linear gradient to 80% mobile phase B (99.9:0.1 vol/vol methanol/acetic acid) and a linear gradient to 100% mobile phase B over 7 min. MS analyses were carried out using electrospray ionization in the positive ion mode using full scan analysis with an ion spray voltage of 3.0 kV, capillary and probe heater temperature of 300° C.

For the measurement of sphingosine-1-phosphate, metabolites were extracted from cell pellets (3×107 cells) in 80% methanol containing Prostaglandin E2-d4 (PGE2-d4) as an internal standard (available from Cayman Chemical Co., Ann Arbor, Mich.). Extracts were injected onto a 150×2 mm ACQUITY T3 column (available from Waters Corp., Milford, Mass.). The column was eluted isocratically at a flow rate of 450 μL/min with 25% mobile phase A (0.1% formic acid in water) for 1 minute followed by a linear gradient to 100% mobile phase B (acetonitrile with 0.1% formic acid) over 11 minutes. MS analyses were carried out using electrospray ionization in the negative ion mode using full scan analysis is with an ion spray voltage of −3.5 kV, capillary temperature of 320° C. and probe heater temperature of 300° C.

Raw data for both methods were processed using Progenesis® CoMet and QI software (available from NonLinear Dynamics, Durham, N.C.) for feature alignment, nontargeted signal detection, and signal integration. Targeted processing and manual inspection of features was conducted using TraceFinder™ software (available from Thermo Fisher Scientific, Waltham, Mass.).

Figure 13:
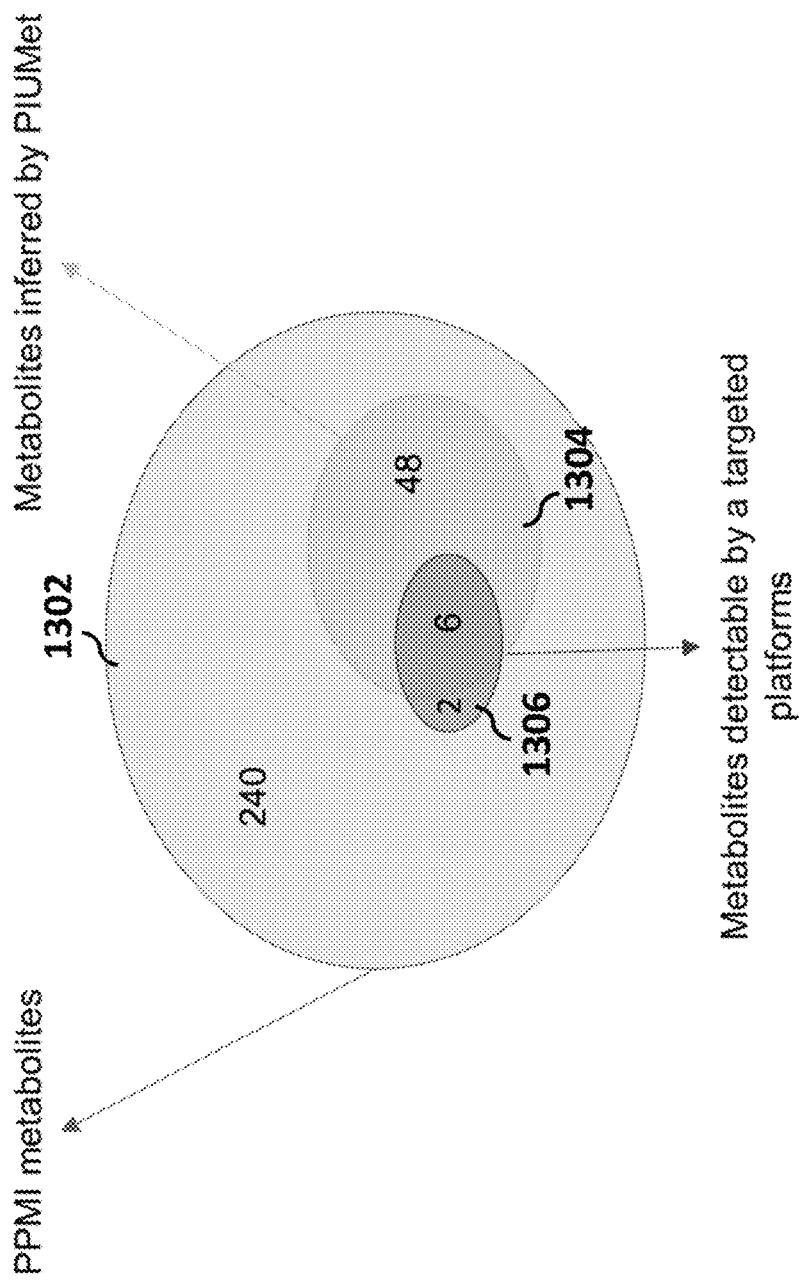
FIG. 13 is a Venn diagram comparing metabolites matching disease features based on mass to metabolites inferred by a network-based approach in accordance with some embodiments.

FIG. 13 is a Venn diagram comparing potential metabolites matching disease features based on mass to putative metabolites inferred by a network-based approach in accordance with some embodiments. Of the 240 metabolites in PPMI network 1302, 54 metabolites were inferred by a PIUMet algorithm 1304. The metabolites inferred by the PIUMet algorithm 1304 are significantly enriched for the metabolites detected by a targeted metabolomic platform 1306 (hypergeometric test P-value=6.00×10-4). All of the metabolites identified by the targeted metabolomic platform 1306 were dysregulated in diseased cells.

According to some embodiments, untargeted lipid profiling data from a cell line model of HD was analyzed. The results showed a highly probable network indicating the mechanisms causing changes in the global level of lipids in the mutated cells. Untargeted lipid data was integrated with global phospho-proteomic data in the Huntington's disease cell lines according to some embodiments. As a result, three networks were generated. While network one and two linked the changes in either lipid or phospho-proteomic data, network three linked the changes in both of these data. A score was assigned to each of the nodes in the resultant networks based on their robustness to the noise in databases. The nodes with the highest score were identified as potential components of signaling pathways altering lipid and phospho-protein metabolisms in Huntington's disease. The changes in the protein levels of the nodes with the highest scores were experimentally validated. Thus, a highly probable network containing potential regulatory mechanisms altering the level of metabolites and phospho-proteins in Huntington's disease was identified.

Figure 14:
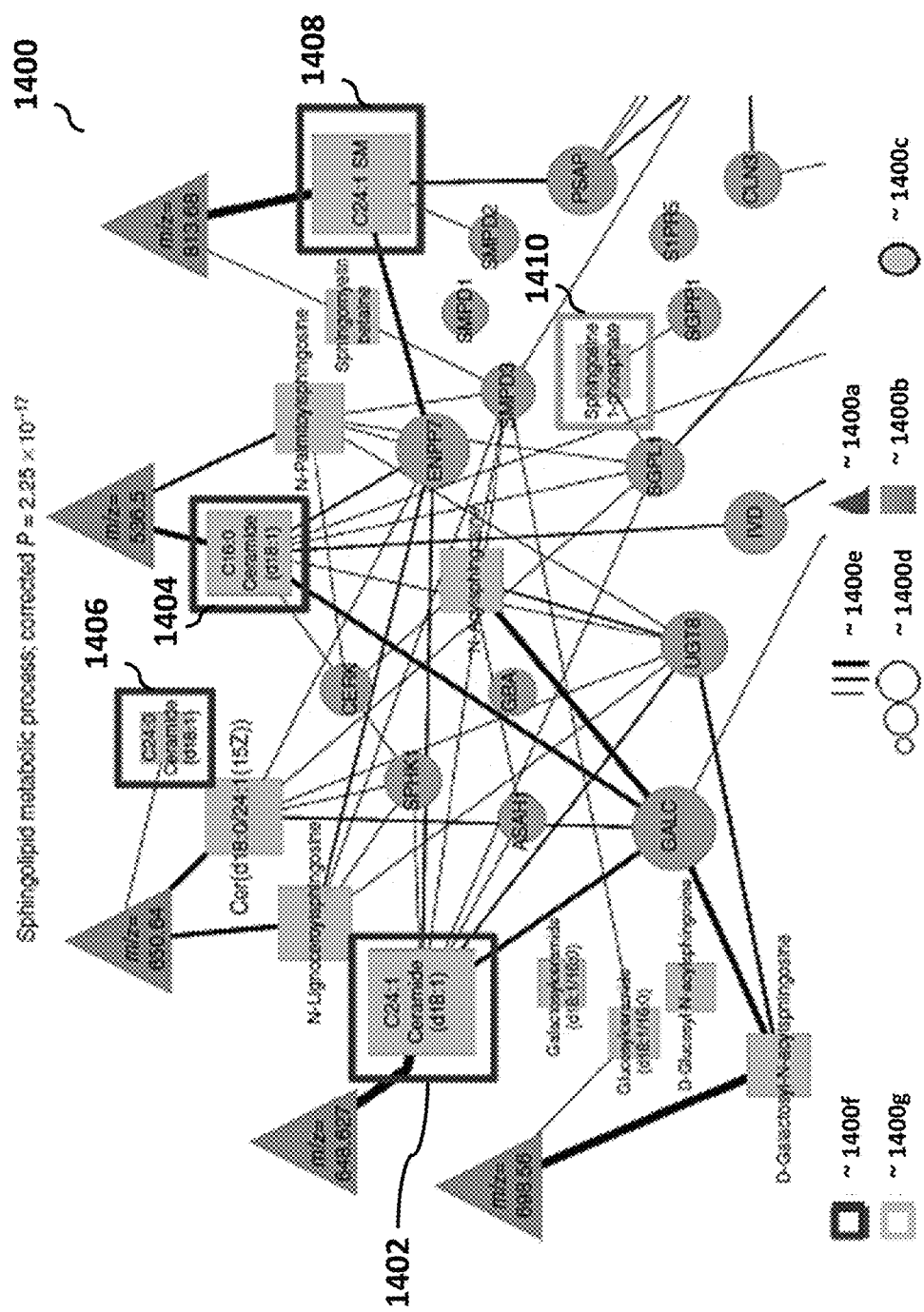
FIG. 14 is a network diagram illustrating significantly dysregulated metabolic pathways in a STHdh cell line model of Huntington's disease (HD) inferred via a network-based approach in accordance with some embodiments.

The dysregulation of sphingolipids (upregulated and downregulated) was experimentally verified using a targeted metabolomic platform. FIG. 14 is a network diagram illustrating significantly dysregulated metabolic pathways in the STHdh cell line model of HD inferred via a network-based approach in accordance with some embodiments. In particular, FIG. 14 includes subnetwork 1400, which shows an altered sphingolipid metabolic process in the STHdh cell line model of HD (corrected P-value=$2.25 \times 10^{-17}$). A PIUMet algorithm connects disease features 1400a via high-probability protein-protein and protein-metabolite interactions. Metabolites 1400b connected to disease features represent their putative identities. Also shown are hidden proteins 1400c that play a role in dysregulation of sphingolipids in diseased cells. These nodes and their connecting edges are ranked based on their disease specific scores, which are represented via different sizes (node scores 1400d) and different weights (edge scores 1400e).

In subnetwork 1400, altered sphingolipids C24:0 Ceramide (d18:1) 1402, C16:0 Ceramide (d18:1) 1404, C24:1 Ceramide (d18:1) 1406, and C24:1 SM 1408 are significantly upregulated in diseased cells 1400f, whereas altered sphingolipid Sphingosine-1-phosphate is significantly downregulated in diseased cells 1400g.

FIGS. 15A-15D are bar plots comparing altered sphingolipids in STHdh Q111 cells to STHdh Q7 cells in accordance with some embodiments. Sphingolipids C24:0 Ceramide (d18:1), C16:0 Ceramide (d18:1), C24:1 Ceramide (d18:1), and C24:1 SM, respectively, were measured in nine biological replicates and subjected to two-sided student t-test analysis. FIG. 15A shows that C24:0 Ceramide (d18:1) was significantly upregulated (P-value=$1.2 \times 10^{-11}$, two-sided student t-test) in STHdh Q111 cells compared to STHdh Q7 cells. FIG. 15B shows that C16:1 Ceramide (d18:1) was significantly upregulated (P-value=$7.74 \times 10^{-5}$, two-sided student t-test) in STHdh Q111 cells compared to STHdh Q7 cells. FIG. 15C shows that C24:1 Ceramide (d18:1) was significantly upregulated (P-value=0.02, two-sided student t-test) in STHdh Q111 cells compared to STHdh Q7 cells. FIG. 15D shows that C24:1 sphingomyelin (SM) was significantly upregulated (P-value=$2.07 \times 10^{-8}$, two-sided student t-test) in STHdh Q111 cells compared to STHdh Q7 cells. The height of each bar plot shows the average of each sphingolipid level, while each error bar shows the standard deviation of each sphingolipid level.

Figures 16A, 16B:
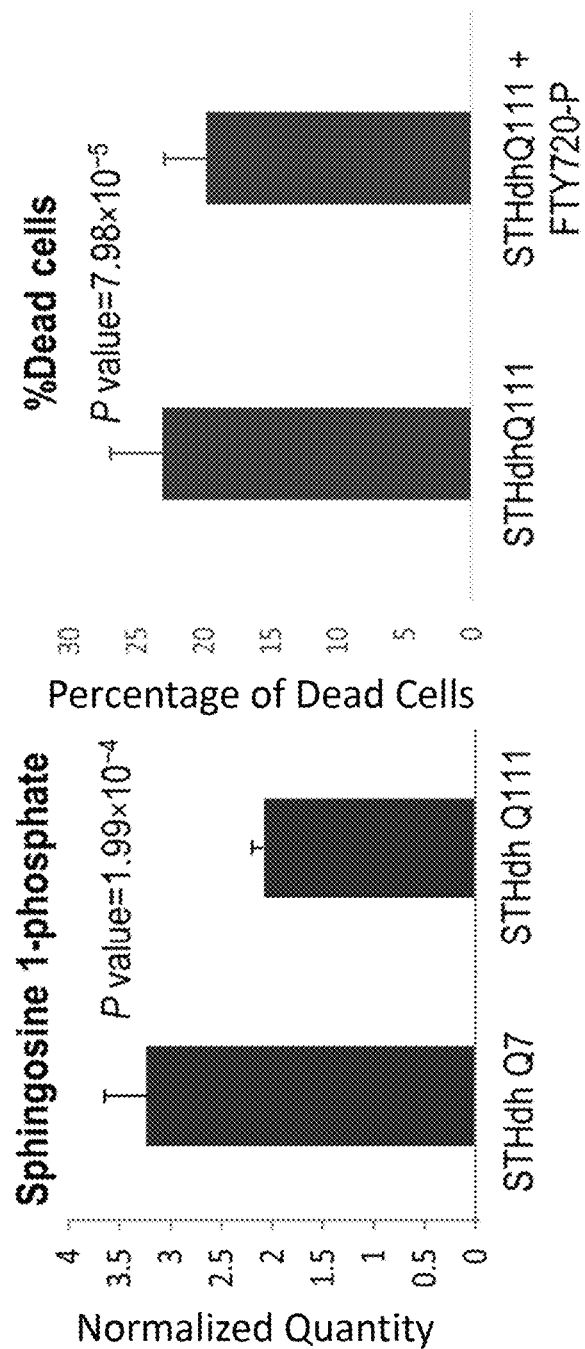
FIG. 16A is a bar plot comparing altered Sphingosine-1-phosphate (S1P) in STHdh Q111 cells to STHdh Q7 cells in accordance with some embodiments.
FIG. 16B is a bar plot comparing percentages of dead cells in untreated and treated STHdh Q111 cells in accordance with some embodiments.

Additionally, PIUMet identified sphingosine 1-phosphate (S1P) as a hidden metabolite in this pathway, to which there was no corresponding metabolite peak from LC-MS experiments. S1P is a key signaling molecule that activates anti-apoptotic pathways by binding to cell-surface receptors. FIG. 16A is a bar plot comparing altered Sphingosine-1-phosphate (S1P) in STHdh Q111 cells to STHdh Q7 cells in accordance with some embodiments. FIG. 16A shows that, as a disease-modifying hidden component of dysregulated sphingolipid pathway, S1P was significantly downregulated (P-value=$1.99 \times 10^{-4}$, two-sided student t-test) in STHdh Q111 cells compared to STHdh Q7 cells. The bar plot shows the average levels of S1P that were measured in nine biological replicates. The error bars show the standard deviation of S1P levels.

FIG. 16B is a bar plot comparing percentages of dead cells in STHdh Q111 cells not treated with an analogue of S1P (FTY720-P) to STHdh Q111 cells treated with FTY720-P in accordance with some embodiments. Treatment of diseased cells with a S1P analog (FTY720-P) had protective effects, significantly decreasing apoptosis (P-value=$7.98 \times 10^{-5}$, two-sided student t-test) in STHdh Q111 cells. The bar plot shows the average percentage of cell death, and the error bars show the standard deviation from two independent experiments with twenty replicates each. Although S1P has been previously examined in the context of HD, those investigations had been motivated by the effect of S1P in other neurodegenerative diseases, and did not identify the molecular mechanisms. In contrast, this approach inferred the underlying network of sphingolipid dysregulation and the role of S1P in diseased cells without any prior assumptions.

Figure 17:
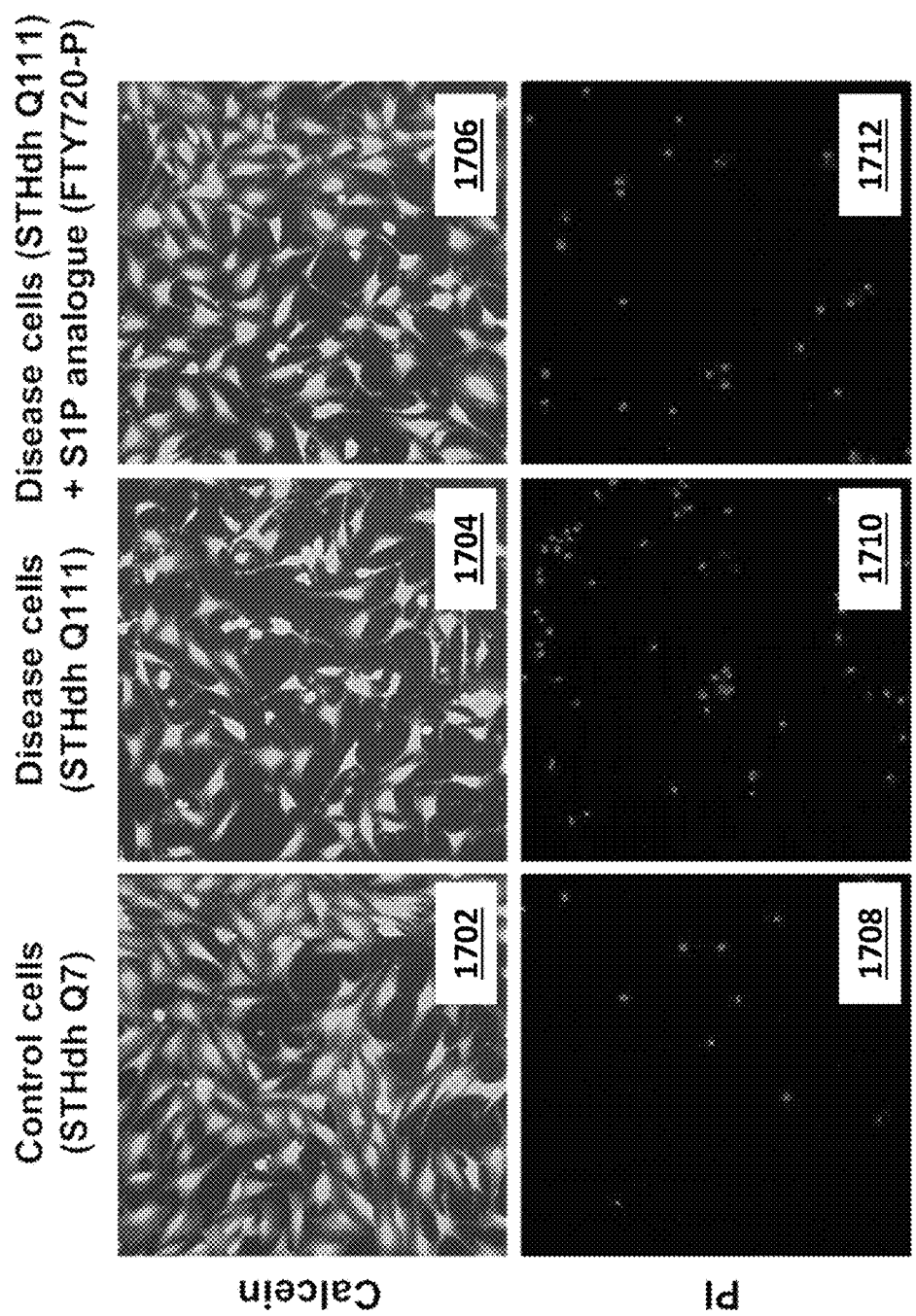
FIG. 17 is a series of images comparing cell viability, morphology, and shape in accordance with some embodiments.

FIG. 17 is a series of images illustrating cell viability, morphology, and shape in accordance with some embodiments. Images 1702, 1704, and 1706 show STHdh Q7 cells, STHdh Q111 cells, and STHdh Q111 cells treated with FTY720-P, respectively, following treatment with calcein to detect viable cells and monitor changes in cell shape and morphology. Images 1708, 1710, and 1712 show STHdh Q7 cells, STHdh Q111 cells, and STHdh Q111 cells treated with FTY720-P, respectively, following treatment with propidium iodide, which stains late apoptotic cells with damaged membranes. As shown, hidden components inferred by using the described approach rescue diseased cells. Phosphorylated FTY720 significantly decrease apoptosis in the STHdh Q111 cells.

PIUMet also discovered an altered steroid metabolism network in the HD model, consistent with previous reports. Specifically, progressive alterations have been shown in sterol precursors of cholesterol in the R6/1 mouse model of HD21. However, the molecular mechanisms underlying these changes are unknown.

Figure 18:
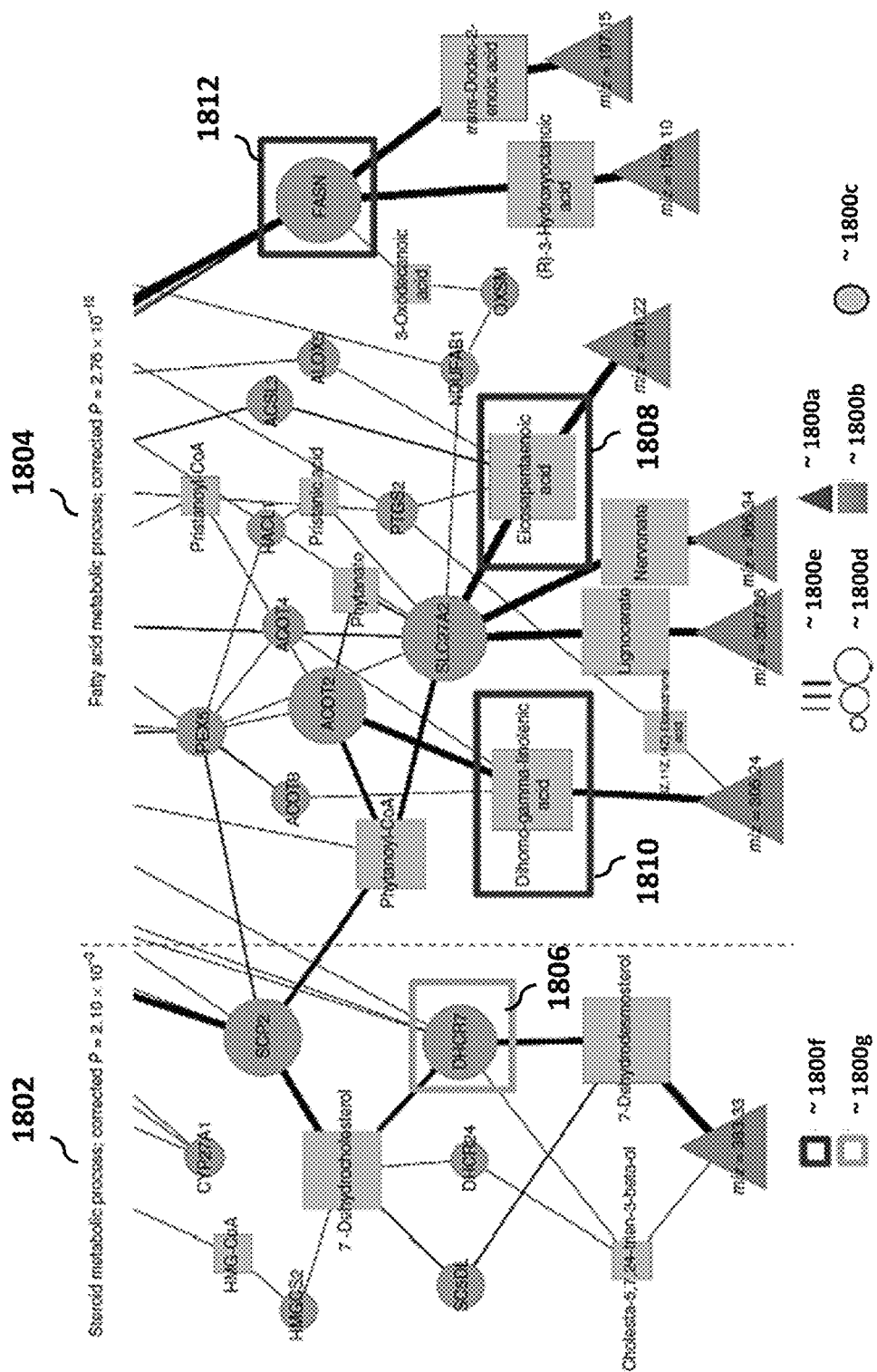
FIG. 18 is a network diagram illustrating altered fatty acid and steroid metabolic processes inferred via a network-based approach in accordance with some embodiments.

FIG. 18 is a network diagram illustrating altered fatty acid and steroid metabolic processes inferred via a network-based approach in accordance with some embodiments. In particular, FIG. 18 includes a subnetwork showing an altered steroid metabolic process 1802 (corrected P-value=$2.10 \times 10^{-3}$). A PIUMet algorithm connects disease features 1800a via high-probability protein-protein and protein-metabolite interactions. Metabolites 1800b connected to disease features represent their putative identities. Also shown are hidden proteins 1800c that play a role in dysregulation of sphingolipids in diseased cells. These nodes and their connecting edges are ranked based on their disease specific scores, which are represented via different sizes (node scores 1800d) and different weights (edge scores 1800e).

Alteration in diseased cells was experimentally verified for nodes that are significantly upregulated in diseased cells 1800f and significantly downregulated in diseased cells 1800g. In process 1802, altered DHCR7-encoded protein 1806 is significantly downregulated in diseased cells 1800g. In process 1804, altered metabolites eicosapentaenoic acid 1808 and dihomo-gamma-linolenic acid 1810 are significantly upregulated in diseased cells 1800f. Altered FASN-encoded protein 1810 is also significantly upregulated in diseased cells 1800f.

For total protein extraction, cells were lysed in RIPA buffer (50 mM Tris-HCl pH 7.4, 150 mM NaCl, 1% NP-40, 0.1% SDS, 12 mM sodium deoxycholate) supplemented with protease and phosphatase inhibitor cocktail (available from, e.g., Thermo Scientific). Nuclear extracts were prepared. Total and nuclear protein extracts were quantified with the Bradford assay using bovine serum albumin as standard. Western Blot experiments were carried out using the Odyssey infrared imaging system (available from Li-Cor Biosciences). The following primary antibodies were used: anti-CSB (sc-25370—dilution 1:200, available from Santa Cruz Biotechnology), anti-DHCR7 (ab103296—dilution 1:500, available from Abcam), anti-RASA1 (ab40807—dilution 1:1000, available from Abcam). An antibody against Actin protein (MAB1501—dilution 1:10000, available from Millipore) was used for normalization.

Figures 19A, 19B:
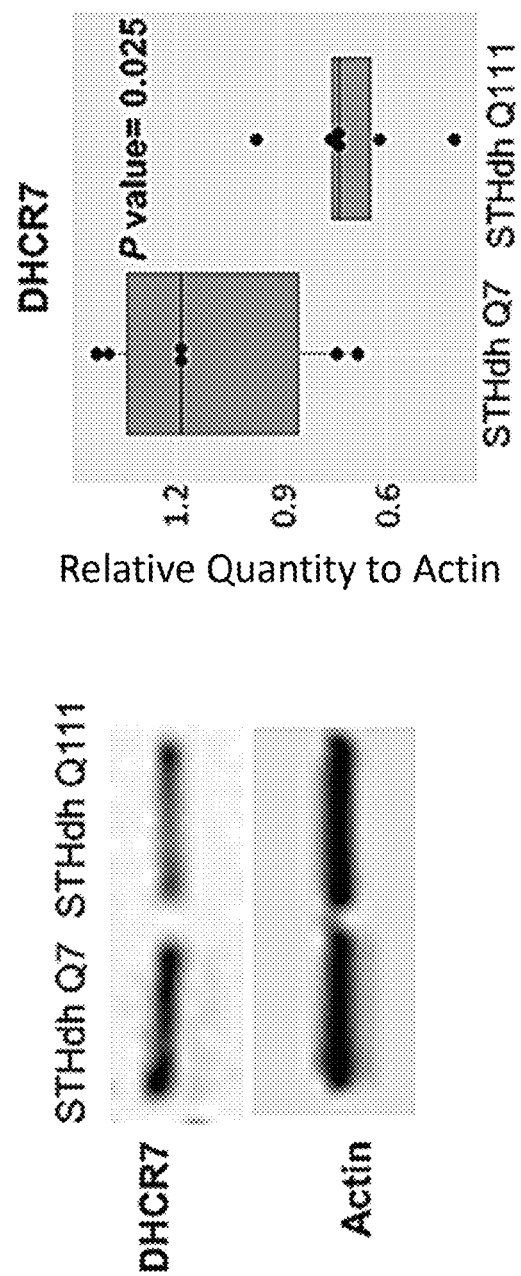
FIG. 19A is a series of images comparing altered Western blot results in STHdh Q111 cells to STHdh Q7 cells in accordance with some embodiments.
FIG. 19B is a bar plot comparing protein levels in STHdh Q111 cells to STHdh Q7 cells in accordance with some embodiments.

One of the high-scoring nodes in the model was DHCR7 (z-score R=2.22), a terminal enzyme in cholesterol biosynthesis. FIG. 19A is a series of images comparing altered Western blot results in STHdh Q111 cells to STHdh Q7 cells in accordance with some embodiments. Western blot results showed that the DHCR7-encoded protein (compared to actin) was significantly downregulated (P-value=0.025, two-sided student t-test) in the STHdh Q111 cells compared to STHdh Q7 cells. FIG. 19B is a bar plot comparing measured levels of DHCR7-encoded protein (normalized relative to actin) in six biological replicates (black dots) each of STHdh Q111 cells and STHdh Q7 cells in accordance with some embodiments. Thus, PIUMet identified DHCR7 as one of the key regulatory molecules in this pathway, which can be further investigated for therapeutic purposes.

Figure 20B:
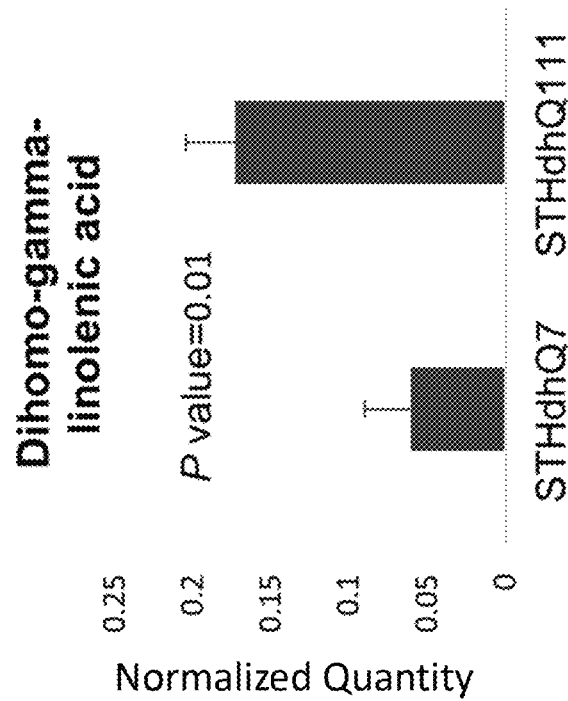
FIGS. 20A and 20B are bar plots comparing altered fatty acids in STHdh Q111 cells to STHdh Q7 cells in accordance with some embodiments.
Figure 20A:
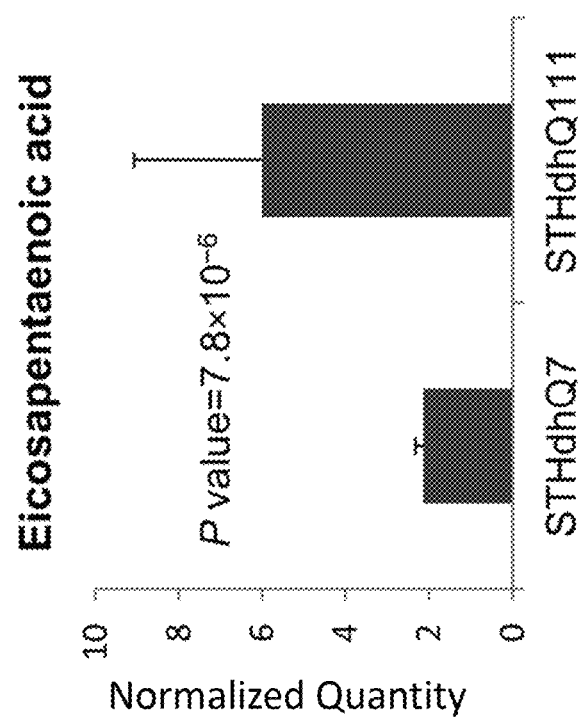

In the subnetwork associated with fatty acid metabolism of FIG. 18, fatty acids are major components of neuronal membranes and the myelin sheath, and their balanced levels are essential in the brain. Fatty acid dysregulation has been associated with HD. FIGS. 20A and 20B are bar plots comparing altered fatty acids in STHdh Q111 cells to STHdh Q7 cells in accordance with some embodiments. These fatty acids were measured in nine biological replicates.

FIG. 20A shows that eicosapentaenoic acid (EPA) was significantly upregulated (P-value=$7.8 \times 10^{-6}$, two-sided student t-test) in STHdh Q111 cells compared to STHdh Q7 cells. FIG. 20B shows that dihomo-gamma-linolenic acid (DHGLA) was significantly upregulated (P-value=0.01, two-sided student t-test) in STHdh Q111 cells compared to STHdh Q7 cells. The height of each bar shows the average of each fatty acid level, while each error bar shows the standard deviation. Both EPA and DHGLA are essential fatty acids, and no prior reports have been identified about their levels in HD neuronal tissues. Notably, because EPA has been reported to have neuroprotective effects in many systems, it has been tested as a therapeutic for HD despite the absence of any previous molecular data about its levels in disease cells. This unbiased analysis of untargeted metabolomic data suggested a molecular mechanism behind EPA's therapeutic effects, and revealed an unknown aspect of altered fatty acid metabolism in HD associated with DHGLA.

Figures 21A, 21B:
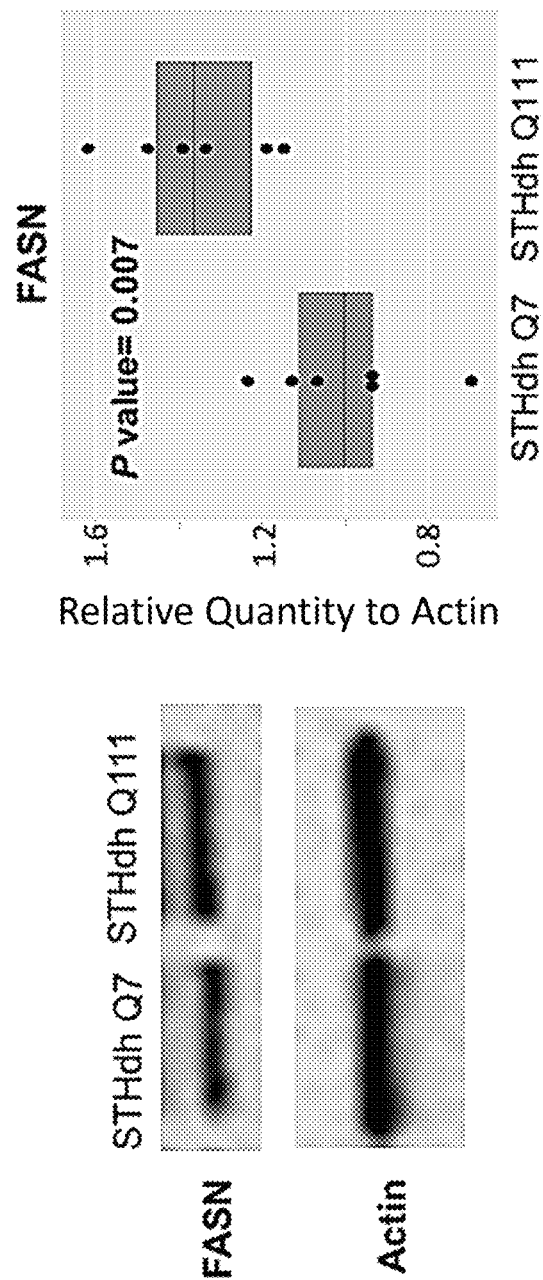
FIG. 21A is a series of images comparing altered Western blot results in STHdh Q111 cells to STHdh Q7 cells in accordance with some embodiments.
FIG. 21B is a bar plot comparing protein levels in STHdh Q111 cells to STHdh Q7 cells in accordance with some embodiments.

The capability of the network approach to correctly infer connections between metabolites and proteins was tested according to some embodiments. One of the highest scoring proteins in the network was FASN (z-score R=3.08), which is involved in de novo fatty acid biosynthesis. In the resulting network, FASN was connected to intermediate metabolites in fatty acid synthesis pathways. FIG. 21A is a series of images comparing altered Western blot results in STHdh Q111 cells to STHdh Q7 cells in accordance with some embodiments. Western blot results showed that the fatty acid synthase enzyme, encoded by the FASN gene (compared to actin) was significantly downregulated (P-value=0.025, two-sided student t-test) in the STHdh Q111 cells compared to STHdh Q7 cells. FIG. 21B is a bar plot comparing measured levels of FASN-encoded protein (normalized relative to actin) in six biological replicates (black dots) each of STHdh Q111 cells and STHdh Q7 cells in accordance with some embodiments. Collectively, these results provided insights about dysregulation of fatty acid metabolism in HD.

According to some embodiments, application of a PIUMet algorithm inferred specific and robust dysregulated pathways in the STHdh cell lines, altering the level of differential lipid features. Changes in global levels of lipids between STHdhQ7 and STHdhQ111 cells were measured by purification of the lipids using liquid chromatography followed by mass spectrometry, resulting in 115 differential lipid peaks (P-value≤0.01) between disease and control systems were detected, in which 38 of differential lipid features were matched to the 302 potential known metabolites in the Recon and HMDB databases.

The PIUMet algorithm then inferred a network of protein-protein and protein-metabolite interactions among them that has the highest probability controlling the dysregulated lipids matching to the differential features. The nodes in the network are ranked based on their robustness score, indicating how robust they are via noises in the databases. In addition, the node specificity and network disease specific scores are calculated. The results showed that the inferred network is significantly relevant to the disease (P-value=1.2E-37), while the inferred nodes were specific to the disease (P-value≤0.1).

Figure 22:
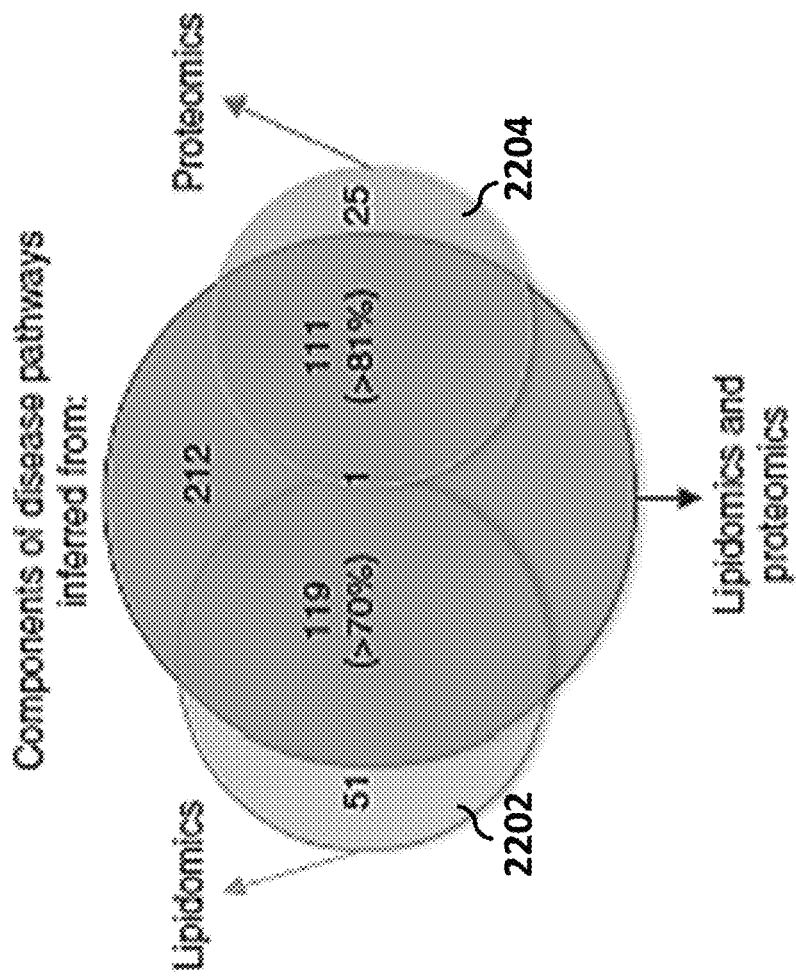
FIG. 22 is a Venn diagram comparing disease-associated components identified in separate analyses of lipidomics and phosphoproteomics, and in an integrative analysis of those data in accordance with some embodiments.

FIG. 22 is a Venn diagram comparing disease-associated components identified in separate analyses of lipidomics and phosphoproteomics, and in an integrative analysis of those data in accordance with some embodiments. For example, integrative analysis of lipidomic 2202 and phosphoproteomic data 2204 in STHdh cell lines reveal novel dysregulated proteins in HD that link changes in the level of lipids to phospho-proteins. If the nodes are clustered based on their scores, a cluster of nodes with higher probability of regulatory roles may be identified in a systematic way thereby connecting changes in proteomics to lipidomics and vice versa.

Figure 23:
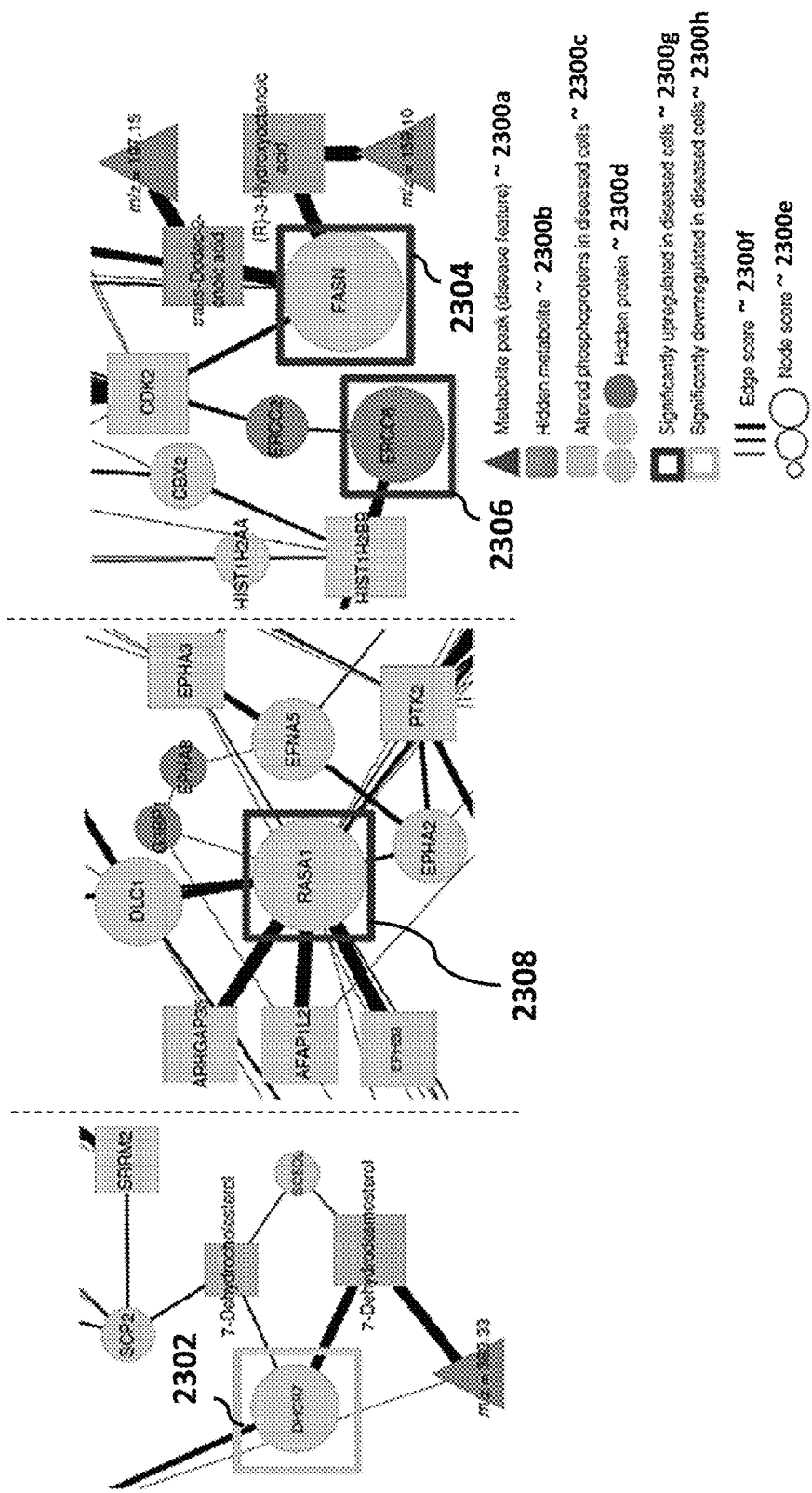
FIG. 23 is a series of network diagrams illustrating dysregulation of high-scoring, hidden components inferred via a network-based approach in accordance with some embodiments.

FIG. 23 is a series of network diagrams illustrating dysregulation of high-scoring, hidden components inferred via a network-based approach in accordance with some embodiments. In particular, FIG. 23 shows regions of a resulting network obtained from integrative analysis of lipidomics and phosphoproteomics. A PIUMet algorithm connects disease features 2300a via high-probability protein-protein and protein-metabolite interactions. Metabolites 2300b connected to disease features represent their putative identities. Also shown are altered phosphoproteins in 2300c and hidden proteins 2300d that play a role in dysregulation of sphingolipids in diseased cells. These nodes and their connecting edges are ranked based on their disease specific scores, which are represented via different sizes (node scores 2300e) and different weights (edge scores 2300f). Alteration in diseased cells was experimentally verified for nodes that are significantly upregulated in diseased cells 2300g and significantly downregulated in diseased cells 2300h.

In FIG. 23, high-scoring proteins belong to three subsets of nodes. The first subset contains nodes that increase in robustness when lipidomics and phosphoproteomics are considered together compared to lipidomics alone. DHCR-encoded protein 2302 (z-score R=3.96) and FASN-encoded protein 2304 (z-score R=4.7) are high-scoring members of this subset, which are described above, were verified experimentally, and were significantly altered in diseased cells (two-tailed student's t-test). The second subset includes nodes that increase in robustness when lipidomics and phosphoproteomics are considered together compared to phosphoproteomics alone. RASA1-encoded protein (Ras-Gap) 2308 had the highest robustness score among the proteins that were originally found with only phosphoproteomic data, and the score of which increased with joint analysis with lipidomics (z-score of R=4.70). A significant increase in the level of RasGap 2308—which interacts with the mutated huntingtin protein27, but has an unknown role in HD progression—was experimentally determined (P-value=0.008). Finally, the third subset contains proteins that are only identified by multi-omic analysis of lipidomics and phosphoproteomics. RCC6-encoded protein 2306, a high-scoring node in this subset, was confirmed to be significantly upregulated in diseased cells.

Of the proteins that only appeared in the integrative analysis, ERCC6-encoded protein CSB 2310 (z-score of R=2.74) had a significant increase in its levels (P-value<0.05). CSB 2310 is a DNA-excision repair protein involved in neurogenesis and neuronal development, which may have a role in HD because defects in DNA-repair mechanisms has been associated with the disease.

FIG. 24A is a series of images comparing altered Western blot results in STHdh Q111 cells to STHdh Q7 cells in accordance with some embodiments. Western blot results showed a significant increase in RASA1 protein levels (compared to actin) (P-value=0.008, two-sided student t-test) in the STHdh Q111 cells compared to STHdh Q7 cells. FIG. 24B is a bar plot comparing measured levels of RASA1 protein (normalized relative to actin) in three biological replicates (black dots) each of STHdh Q111 cells and STHdh Q7 cells in accordance with some embodiments.

FIG. 24C is a series of images comparing altered Western blot results in STHdh Q111 cells to STHdh Q7 cells in accordance with some embodiments. Western blot results showed a significant increase in ERCC6 protein levels (compared to actin) (P-value=0.028, two-sided student t-test) in the STHdh Q111 cells compared to STHdh Q7 cells. FIG. 24D is a bar plot comparing measured levels of ERCC6-encoded protein (normalized relative to actin) in six biological replicates (black dots) each of STHdh Q111 cells and STHdh Q7 cells in accordance with some embodiments.

Examples of top gene ontology enrichment of the resultant network linking changes in the levels of lipids and phospho-proteins respectively between wild-type and mutated STHdh cell lines are shown in TABLES 4 and 5, respectively.

TABLE 4

| Description | P-value | FDR q-value |
|---|---|---|
| Sphingolipid metabolic process | 4.01E−20 | 1.44E−16 |
| Membrane lipid metabolic process | 2.94E−18 | 7.94E−15 |
| Glycosphingolipid metabolic process | 2.26E−17 | 4.87E−14 |
| Glycolipid metabolic process | 7.88E−15 | 1.06E−11 |
| Liposaccharide metabolic process | 2.56E−14 | 3.07E−11 |
| Ceramide metabolic process | 4.37E−13 | 4.72E−10 |
| Monocarboxylic acid metabolic process | 6.54E−13 | 6.41E−10 |
| Fatty acid metabolic process | 9.83E−12 | 7.07E−09 |

TABLE 5

| Description | P-value | FDR q-value |
|---|---|---|
| Ephrin receptor signaling pathway | 3.83E−11 | 4.27E−07 |
| Transmembrane receptor protein tyrosine kinase signaling pathway | 3.80E−08 | 2.12E−04 |
| Enzyme linked receptor protein signaling pathway | 1.86E−06 | 6.92E−03 |
| Cell-substrate junction assembly | 5.81E−06 | 1.62E−02 |
| Cell adhesion | 7.11E−06 | 1.58E−02 |
| Regulation of cell-matrix adhesion | 4.72E−05 | 7.51E−02 |

There are 7,994 proteins that are connected to phosphoproteins with the weighted shortest path length less than 0.4:

$$B_{pp} = PP \cup \{p | p \in P \wedge \text{weighted shortest path length}(p, PP) \leq \varepsilon\} \quad (15)$$

Examples of top gene ontology enrichment of the resultant network linking changes in the level of phosphoproteins to lipids between wild-type and mutated STHdh cell lines are shown in TABLE 6, correspondingly.

TABLE 6

| Description | P-value | FDR q-value |
|---|---|---|
| Sphingolipid metabolic process | 5.87E−13 | 6.68E−09 |
| Membrane lipid metabolic process | 3.20E−11 | 1.82E−07 |
| Monocarboxylic acid metabolic process | 2.10E−07 | 3.42E−04 |
| Fatty acid metabolic process | 1.32E−06 | 1.25E−03 |
| Small molecule biosynthetic process | 1.32E−06 | 1.15E−03 |
| Peptidyl-tyrosine phosphorylation | 5.28E−06 | 2.86E−03 |
| Peptidyl-tyrosine modification | 5.28E−06 | 2.73E−03 |
| Ephrin receptor signaling pathway | 3.58E−05 | 1.57E−02 |

TABLE 6-continued

| Description | P-value | FDR q-value |
|---|---|---|
| Cell migration | 3.90E−05 | 1.64E−02 |
| Transmembrane receptor protein tyrosine kinase signaling pathway | 4.28E−05 | 1.74E−02 |

$$B = B_L \cup B_{PP} \quad (16)$$

Global Phospho-Protein Profiling of STHdh Cell Line Model of HD

According to some embodiments, samples were prepared for mass spectrometry. Samples were lysed with 8 M urea+1 mM sodium orthovanadate (phosphatase inhibitor) and protein yield was quantified by BCA assay (Pierce). Samples were reduced with 10 µl of 10 mM DTT in 100 mM ammonium acetate pH 8.9 (1 h at 56° C.). Samples were alkylated with 75 µl of 55 mM iodoacetamide in 100 mM ammonium acetate pH 8.9 (1 h at room temperature). One mL of 100 mM ammonium acetate and 10 µg of sequencing grade trypsin (Promega PN:V5111) and digestion proceeded for 16 h at room temperature. Samples were acidified with 125 µl of trifluoroacetic acid (TFA) and desalted with C18 spin columns (ProteaBio, SP-150). Samples were lyophilized and subsequently labeled with iTRAQ 8plex (AbSciex) per manufacturer's directions.

According to some embodiments, immunoprecipitation was performed. Seventy-µl protein-G agarose beads (calbiochem IP08) were rinsed in 400 µl IP buffer (100 mM Tris, 0.3% NP-40, pH 7.4) and charged for 8 h with three phosphotyrosine-specific antibodies (12 µg 4G10 (Millipore), 12 µg PT66 (Sigma), and 12 µg PY100 (CST)) in 200 µl IP buffer. Beads were rinsed with 400 µl of IP buffer. Labeled samples were resuspended in 150 µl iTRAQ IP buffer (100 mM Tris, 1% NP-40, pH 7.4)+300 µl milliQ water and pH was adjusted to 7.4 (with 0.5M Tris HCl pH 8.5). Sample was added to charged beads for overnight incubation. Supernatant was removed and beads were rinsed three times with 400 µl rinse buffer (100 mM Tris HCl, pH 7.4). Peptides were eluted in 70 µl of elution buffer (100 mM glycine, pH 2) for 30 min at room temperature. TABLE 7 shows the iTRAQ labeling scheme. Four biological replicates of each sample were analyzed.

TABLE 7

| iTRAQ Channel | Sample |
|---|---|
| 113 | Q7 BioRep 1 |
| 114 | Q7 BioRep 2 |
| 115 | Q7 BioRep 3 |
| 116 | Q7 BioRep 4 |
| 117 | Q111 BioRep 1 |
| 118 | Q111 BioRep 2 |
| 119 | Q111 BioRep 3 |
| 121 | Q111 BioRep 4 |

According to some embodiments, immobilized metal affinity chromatography (IMAC) purification was performed. A fused silica capillary (FSC) column (200 m inner diameter×10 cm length) was packed with POROS 20MC beads (Applied Biosystems 1-5429-06). IMAC column was prepared by rinsing with solutions in the following order: 100 mM EDTA pH 8.9 (10 min), (10 min), 100 mM FeCl3 (20 min), 0.1% acetic acid (10 min). IP elution was loaded for 30 min at a flow rate of 2 µl/min. The column was rinsed with 25% MeCN, 1% HOAc, and 100 mM NaCl (10 min) and 0.1% acetic acid (10 min). Peptides were eluted with 50 µl 250 mM NaH2PO4 at 2 µl/min and collected on a 10 cm hand-made precolumn (fused silica: Polymicro Technologies cat. no. TSP100375, beads: YMC gel, ODS-A, 12 nm, S-10 m, AA12S11). Precolumn was rinsed with 0.1% acetic acid before analysis.

According to some embodiments, liquid chromatography mass spectrometry was performed. Peptides were analyzed on a 240-min gradient (Agilent 1100 HPLC) from 100% A (0.1% formic acid) to 100% B (0.1% formic acid, 80% acetonitrile) spraying through a hand-made 10 cm analytical column (fused silica: Polymicro Technologies cat. no. TSP050375, beads: YMC gel, ODS-AQ, 12 nm, S-5 m, AQ12S05, bead plug: YMC gel, ODS-A, 12 nm, S-10 µm, AA12S11) with integrated electrospray ionization tip, connected in line with the precolumn.

According to some embodiments, data analysis was performed. Thermo .RAW files were searched with MASCOT v2.4 using Proteome Discoverer (v1.2). Peptides that appeared in all replicates were included if their MASCOT scores exceeded 15 and they were designated as medium or high confidence by Proteome Discoverer. The P-value obtained using a two-tailed t-test is reported between STHdh Q7 and STHdh Q111 biological replicates. Thirty-five peptides were identified that were matched to 31 corresponding phosphoproteins using BLAST program blastp. If multiple peptides matched to one protein, the assigned P value to the protein was considered as the minimum P value of the corresponding peptides. Additionally, as the PPMI network was constructed from human data, the human homologs of these phosphoproteins were identified using NCBI Homolo-Gene database.

Inferring a Network Underlying Changes in Phosphoproteins

When proteomic data were used, according to some embodiments, the input to PIUMet consisted of phosphoproteins with significantly different levels of phosphorylation between STHdh Q7 and STHdh Q111 cells ($P \leq 0.01$; see TABLE 8 below).

TABLE 8

| Phosphorylation Type | Protein | Sequence | Accession GI | Gene Symbol (Mouse) | p-value | Human Homolog |
| --- | --- | --- | --- | --- | --- | --- |
| pY | cyclin-dependent kinase 2 isoform 2 [Mus musculus] | IGEGTyGVVYK | 7949020 | Cdk2 | 9.22E-06 | CDK2 |
| pY | armadillo repeat gene deleted in velo-cardio-facial syndrome [Mus musculus] | DVIPMDTLGPD GyATVDRR | 40254129 | Arvcf | 0.000101022 | ARVCF |
| pY | solute carrier family 12, member 4 [Mus musculus] | RGDyDNLEGLS WVDYGER | 6677993 | Slc12a4 | 0.000120165 | SLC12A4 |
| pY | LIM domain containing preferred translocation partner in lipoma [Mus musculus] | SEGDTAyGQQV QPNTWKR | 31982290 | Lpp | 0.000151808 | LPP |
| pY | X kin or IRRE like 1 [Mus musculus] | AVLyADYR | 70608146 | Kirrel | 0.000188077 | KIRREL |
| pY | glucocorticoid receptor DNA binding factor 1 [Mus musculus] | NEEENIySVPH DSTQGK | 75677442 | Grlf1 | 0.000248962 | ARHGAP35 |
| pST | thymopoietin isoform alpha [Mus musculus] | SsTPLPTVSSS AENTR | 121949760 | Tmpo | 0.000278793 | TMPO |
| pY | partitioning-defective protein 3 homolog isoform 3 [Mus musculus] | ERDyAEIQDFH R | 15809050 | Pard3 | 0.000292998 | PARD3 |
| pY | PREDICTED: src homology 2 domain-containing transforming protein B [Mus musculus] | VTIADDySDPF DAK | 149252377 | Shb | 0.000318506 | SHB |
| pST | H326 [Mus musculus] | GHGHsDEEDEE QPR | 23956326 | Dcaf8 | 0.00082591 | DCAF8 |

TABLE 8-continued

| Phosphory-lation Type | Protein | Sequence | Accession GI | Gene Symbol (Mouse) | p-value | Human Homolog |
|---|---|---|---|---|---|---|
| pY | Tnf receptor associated factor 4 [Mus musculus] | EFVyDTIQSHQYQcPR | 31543889 | Traf4 | 0.001164384 | TRAF4 |
| pY | Eph receptor A3 [Mus musculus] | VLEDDPEAAyTTR | 31982448 | Epha3 | 0.001493525 | EPHA3 |
| pST | minichromosome maintenance deficient 2 mitotin [Mus musculus] | GLLYDssEEDEERPAR | 6678826 | Mcm2 | 0.002127173 | MCM2 |
| pST | heterogeneous nuclear ribonucleoprotein K [Mus musculus] | DYDDMsPR | 13384620 | Hnrnpk | 0.002479144 | HNRNPK |
| pY | proteasome (prosome, macropain) subunit, alpha type 2 [Mus musculus] | SILyDER | 134031994 | Psma2 | 0.002540826 | PSMA2 |
| pY | erythrocyte protein band 4.1-like 2 [Mus musculus] | VDGDNIyVR | 29789052 | Epb4.1l2 | 0.002549899 | EPB41L2 |
| pY | C1 domain-containing phosphatase and tensin-like protein [Mus musculus] | LALPTAALyGLRLER | 119372288 | Tenc1 | 0.002609376 | TENC1 |
| pST | histone 3, H2ba [Mus musculus] | AMGIMNSFVNDIDER | 13386452 | Hist3h2ba | 0.002922793 | HIST1H2BB |
| pY | Rho GTPase activating protein 12 isoform 2 [Mus musculus] | ATTPPNQGRPDsPVyANLQELK | 89242139 | Arhgap12 | 0.002964933 | ARHGAP12 |
| pST | small acidic protein [Mus musculus] | SAsPDDDLGSSNWEAADLGNEER | 9790217 | 1110004F10Rik | 0.003603337 | C11orf58 |
| pST | tight junction protein 1 [Mus musculus] | SREDLsAQPVQTK | 6678355 | Tjp1 | 0.003697822 | TJP1 |
| pY | Eph receptor B3 [Mus musculus] | FLEDDPSDPTyTSSLGGKIPIR | 33859548 | Ephb3 | 0.003947519 | EPHB3 |
| pST | solute carrier family 9 (sodium/hydrogen exchanger), isoform 3 regulator 1 [Mus musculus] | SAsSDTSEELNSQDSPK | 6755566 | Slc9a3r1 | 0.004047664 | SLC9A3R1 |
| pY | actin filament associated protein 1-like 2 [Mus musculus] | VAQQPLSLVGcDVLPDPSPDHLySFR | 22122607 | Afap1l2 | 0.004176885 | AFAP1L2 |
| pY | PTK2 protein tyrosine kinase 2 [Mus musculus] | YMEDSTyYK | 6679741 | Ptk2 | 0.004667398 | PTK2 |
| pST | serine/arginine repetitive matrix 2 [Mus musculus] | SAVRPsPsPER | 126157504 | Srrm2 | 0.004763591 | SRRM2 |

TABLE 8-continued

| Phosphory-lation Type | Protein | Sequence | Accession GI | Gene Symbol (Mouse) | p-value | Human Homolog |
|---|---|---|---|---|---|---|
| pY | catenin, delta 1 isoform 1 [Mus musculus] | HYEDGYPGGSDNyGSLSR | 83745122 | Ctnnd1 | 0.004776682 | CTNND1 |
| pST | eukaryotic translation elongation factor 1 delta isoform b [Mus musculus] | ATAPQTQHVsPMR | 54287684 | Eef1d | 0.006539886 | EEF1D |
| pY | Rho GTPase-activating protein [Mus musculus] | QSSMTVVSQyDNLEDYHSLPQHQR | 28893539 | Arhgap2 | 0.006690421 | ARHGAP32 |
| pY | vinculin [Mus musculus] | SFLDSGyRILGAVAK | 31543942 | Vcl | 0.007618028 | VCL |
| pST | high mobility group AT-hook 2 [Mus musculus] | KPAQETEETsSQESAEED | 6754210 | Hmga2 | 0.008359682 | HMGA2 |

PIUMet identified a subnetwork of the PPMI that connects these phosphoproteins, while calculating a robustness score for each resulting nodes. A family of random networks was generated by randomly selecting phosphoproteins that mimic experimental data. For this purpose, a list of phosphoproteins from the Phosida database was identified. Of these phosphoproteins, 3,858 (>82%) were present in the PPMI network. Then, for an input size T, T of these phosphoproteins were randomly selected, in which the degree distribution of the selected phosphoproteins was similar to the real data. This process was repeated one hundred times to obtain resulting networks. Disease-specific scores were calculated for the resulting nodes and networks. These scores showed that the resulting nodes from real data were specific to the disease (disease-specific score ≥93%), and the resulting networks from real data had significantly higher disease-specific scores compared to those from randomly selected disease features ($P=1.58 \times 10^{-78}$).

Figure 25:
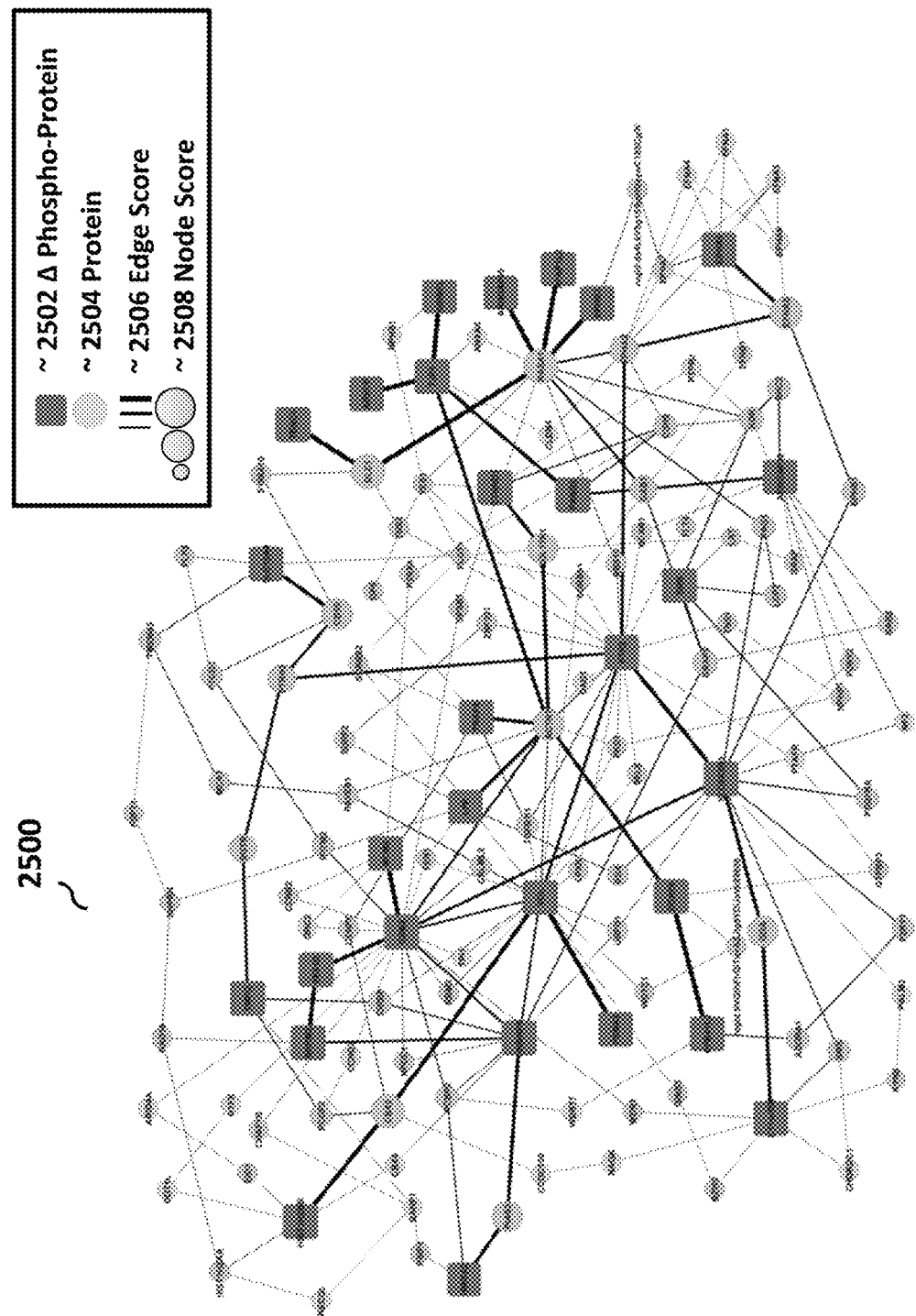
FIG. 25 is a network diagram illustrating signaling pathways causing changes in protein phosphorylation inferred via a network-based approach in accordance with some embodiments.

FIG. 25 is a network diagram illustrating signaling pathways causing changes in protein phosphorylation inferred via a network-based approach in accordance with some embodiments.

Figure 26A:
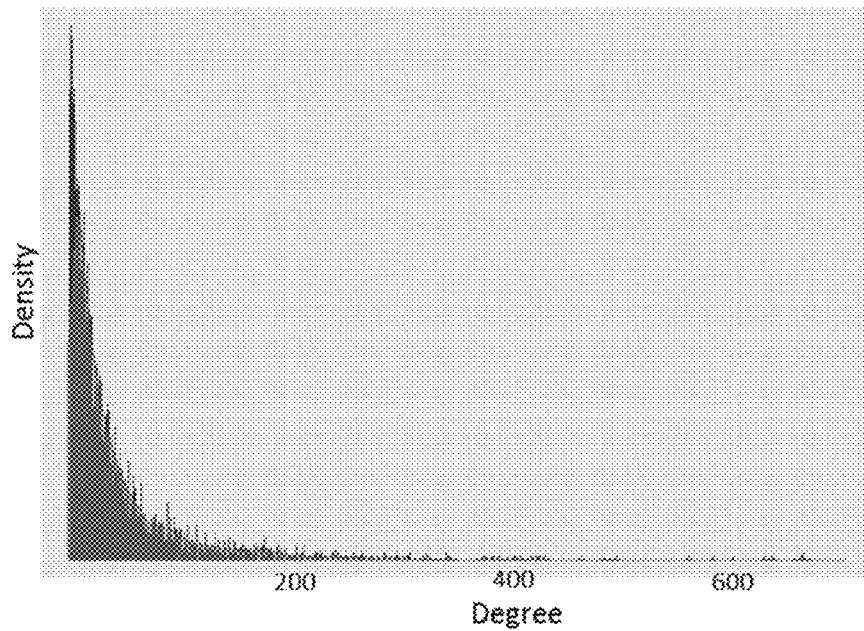
FIGS. 26A and 26B are graphs plotting phospho-protein degree distribution in accordance with some embodiments.
Figure 26B:
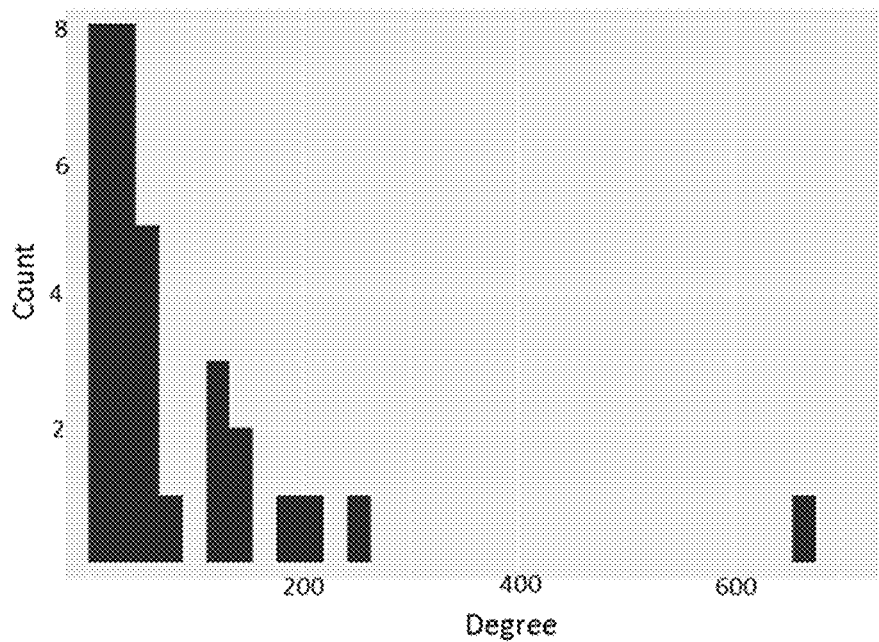

FIGS. 26A and 26B are graphs plotting phospho-protein degree distribution in accordance with some embodiments. FIG. 26A plots degree distribution of all phospho-proteins in a PPMI network, and FIG. 26B plots degree distribution of differential phospho-proteins between wild-type and mutated STHdh cell lines.

Figure 27:
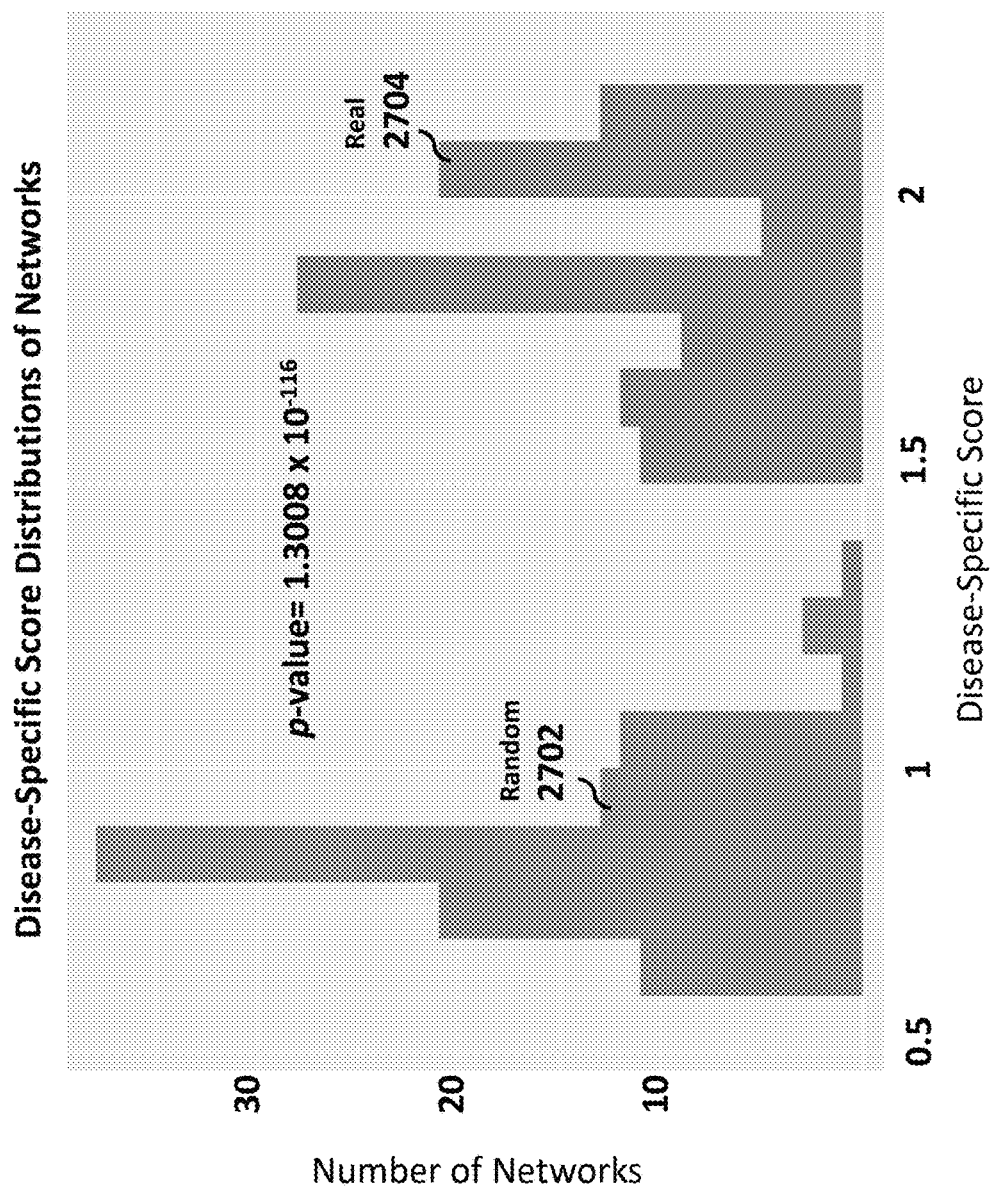
FIG. 27 is a plot comparing disease specific score distributions of a network formed from randomly-selected phospho-proteins to disease specific scores of a network formed from exponential data in accordance with some embodiments.

FIG. 27 is a plot comparing disease specific score distributions of a network formed from randomly-selected phospho-proteins to disease specific scores of a network formed from exponential data in accordance with some embodiments.

Figure 28:
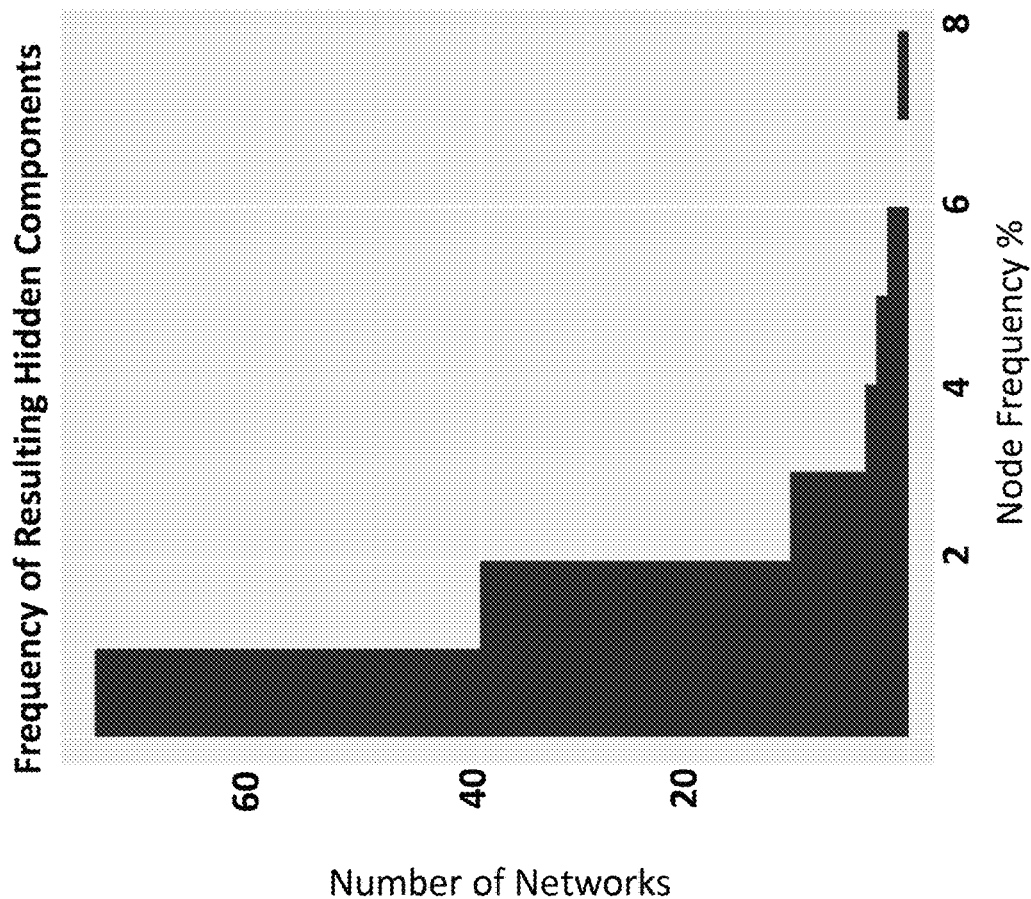
FIG. 28 is a plot illustrating the frequency of Steiner and terminal nodes of a network obtained from phospho-protein data in the randomly resulting networks in accordance with some embodiments.

FIG. 28 is a plot illustrating the frequency of Steiner and terminal nodes of a network obtained from phospho-protein data in the randomly resulting networks in accordance with some embodiments.

Inferring a Network Connecting Untargeted Lipidomic Data to Phosphoproteomic Data According to some embodiments, a PIUMet algorithm was run with both metabolomics disease features and significantly altered phosphoproteins (identified using a two-tailed student's t-test) as inputs. The algorithm identified a subnetwork of the PPMI linking changes in the global level of lipids to changes in phosphoproteins, and calculated robustness scores for the results. In addition, disease-specific scores were calculated for resulting nodes and networks, and found that the nodes were specific to the disease (disease-specific score ≥82%), and networks had significantly higher disease-specific scores compared to those obtained from randomly selected disease features and phosphoproteins (P-value=$1.30 \times 10^{-116}$).

Figure 29:
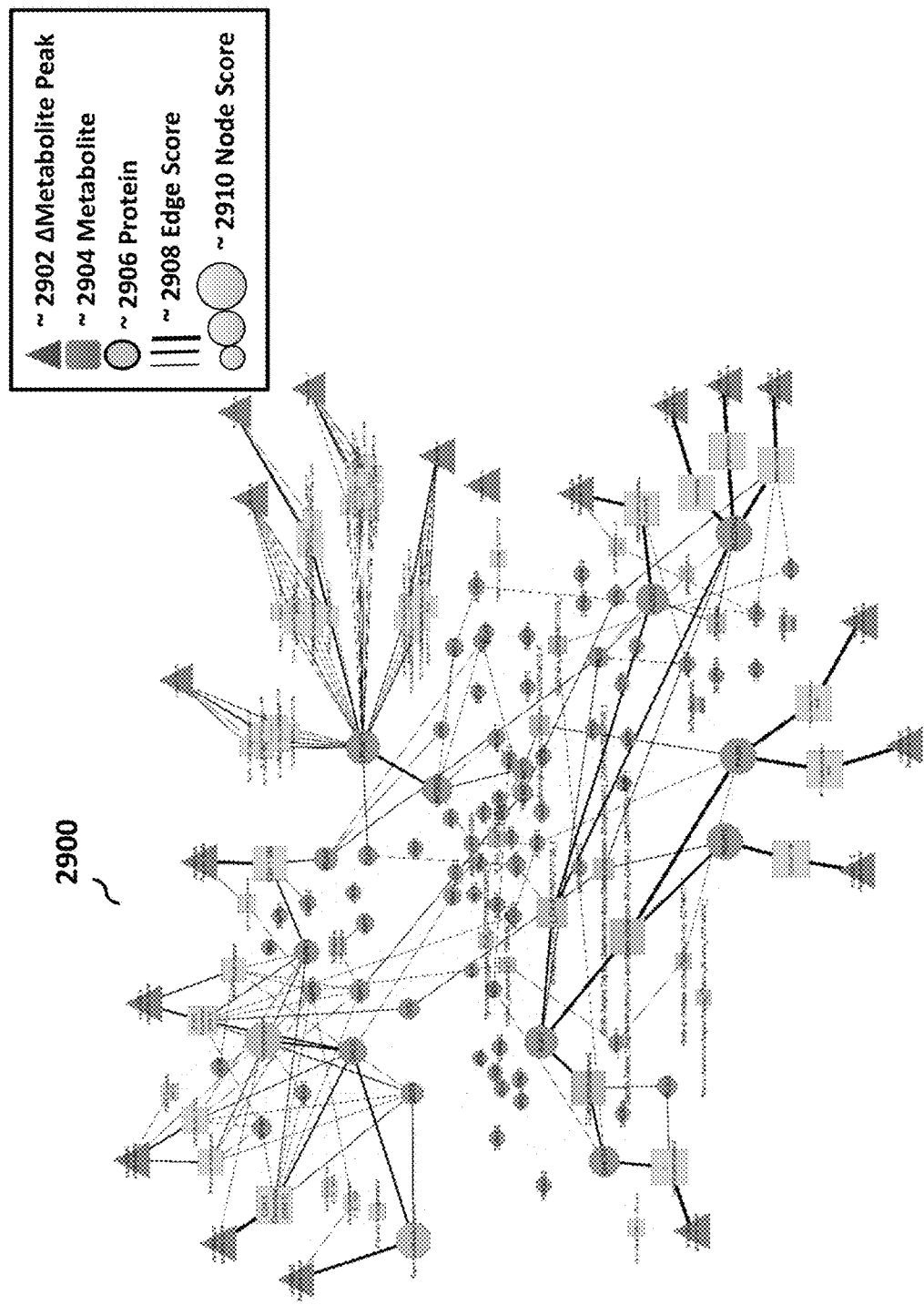
FIG. 29 is a network diagram illustrating deregulated pathways altering a level of lipids in mutated STHdh cell lines compared to the wild type STHdh cell lines in accordance with some embodiments.

FIG. 29 is a network diagram illustrating deregulated pathways altering a level of lipids in mutated STHdh cell lines compared to the wild type STHdh cell lines in accordance with some embodiments.

Figure 30:
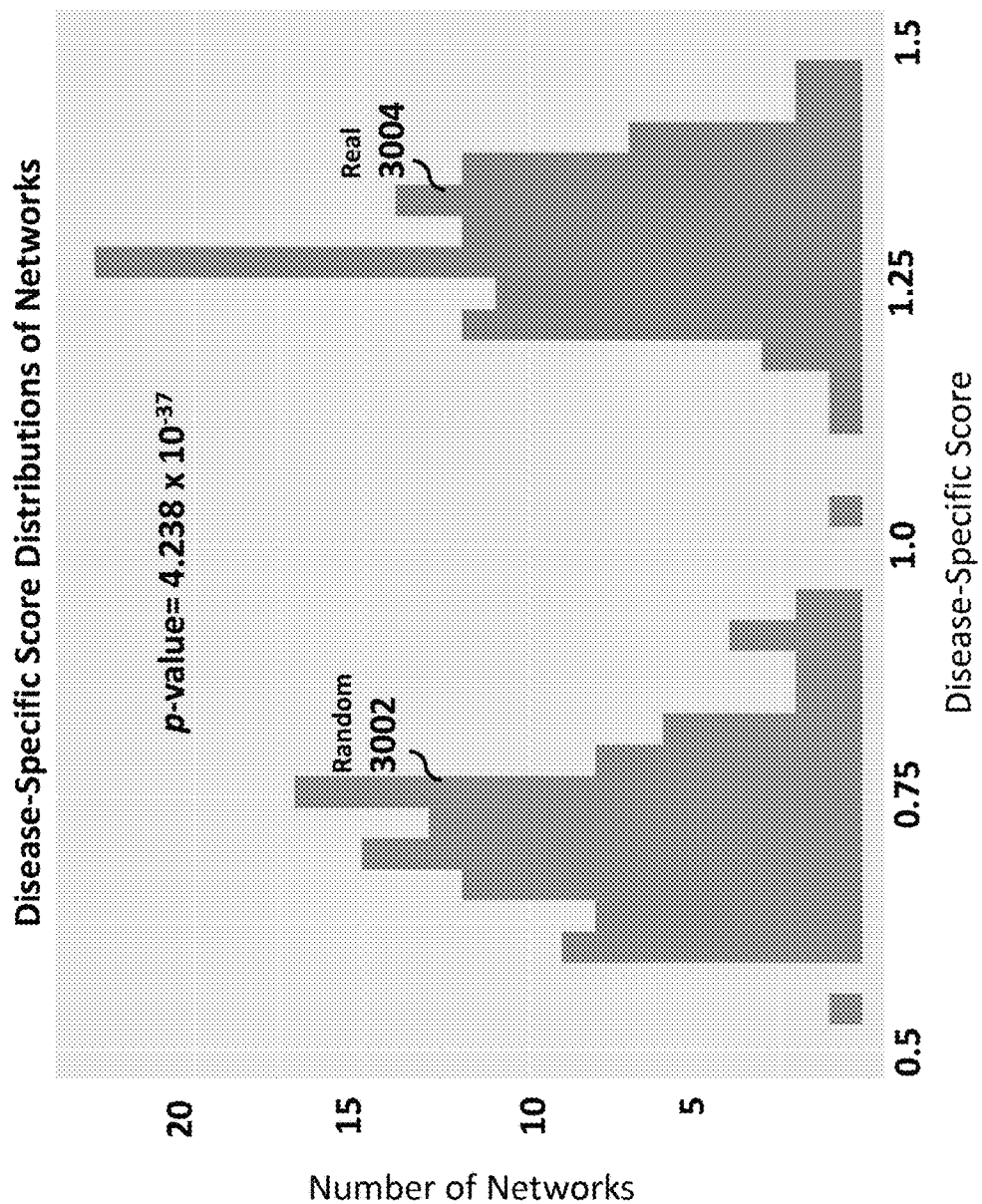
FIG. 30 is a plot comparing disease specific score distributions of a network formed from randomly-selected lipids and phospho-proteins to disease specific scores of a network formed from exponential data in accordance with some embodiments.

FIG. 30 is a plot comparing disease specific score distributions of a network formed from randomly-selected lipids and phospho-proteins to disease specific scores of a network formed from exponential data in accordance with some embodiments.

Figure 31:
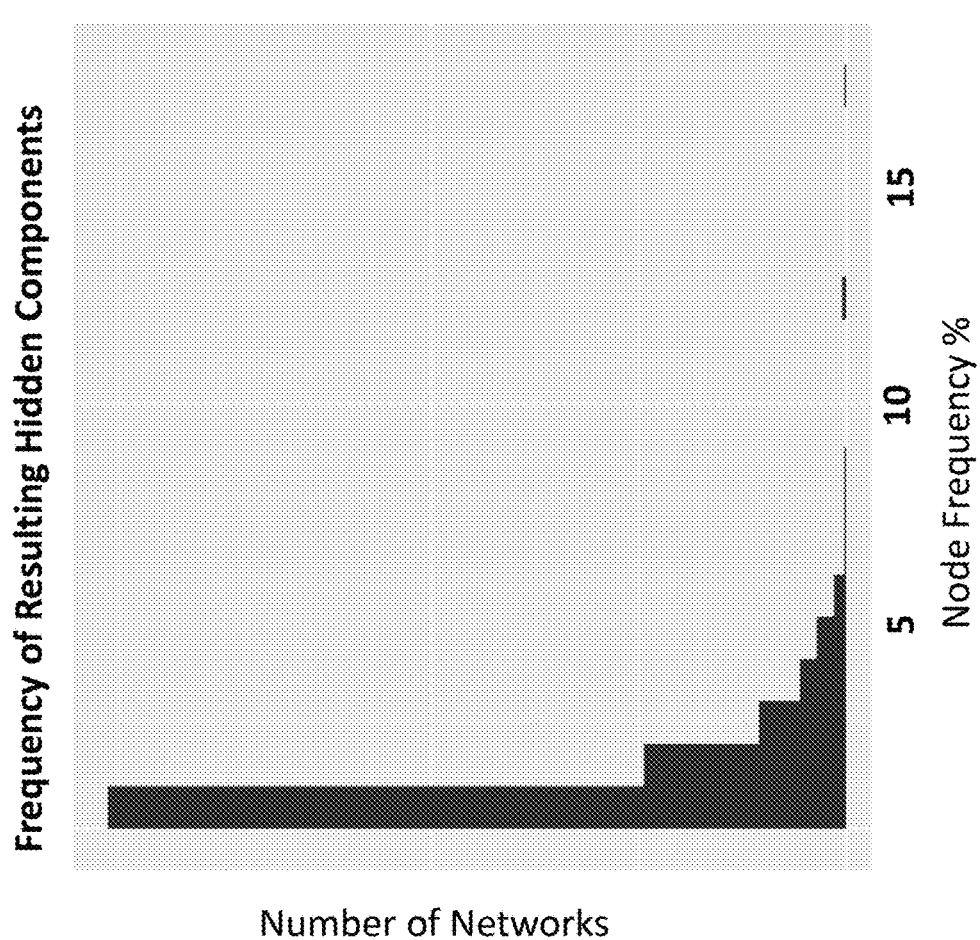
FIG. 31 is a plot illustrating the frequency of Steiner and terminal nodes of a network obtained from alterations in lipid metabolism and protein phosphorylation data in the randomly resulting networks in accordance with some embodiments.

FIG. 31 is a plot illustrating the frequency of Steiner and terminal nodes of a network obtained from alterations in lipid metabolism and protein phosphorylation data in the randomly resulting networks in accordance with some embodiments.

Multiparameter, High Content Imaging for the Analysis of Cell Apoptosis

According to some embodiments, STHdhQ7/Q7 and STHdhQ111/Q111 striatal cells were trypsinized, harvested in pre-warmed growth medium and quantified using an automated cell counter (available from, e.g., Countess II, Life Technologies). Six thousand cells per well were seeded in sterile, black 96-well microplates with flat, clear bottom. After 24 hours, the complete medium was removed and replaced with phenol red- and serum-free medium containing either FTY720 phosphate (available from Sigma-Aldrich) or vehicle (e.g., DMSO, available from Sigma-Aldrich) and cells were incubated for 24 hours at 33° C. A multiple staining solution containing 1 µg/ml calcein-AM, 2 µg/ml propidium iodide and 1.5 µg/ml Hoechst 333442 (all available from Life Technologies) was added to detect and quantify live, dead, and total cells, respectively. After 20 minutes in incubation, a Cellomics Arrayscan Platform (available from Thermo Scientific) was used for imaging acquisition. Seven fields per well were imaged at 10× magnification. Analysis was carried out using the Cellomics algorithm for cell viability. Cell loss was expressed as the percentage of propidium iodide-positive cells. Two independent experiments were performed, with twenty replicates each.

Integrating Metabolomics with Other "Omics"

To test the ability of PIUMet to integrate untargeted lipidomics and global phosphoproteomic data, global levels of phosphoproteins were measured in STHdh Q7 and STHdh Q111 cells by affinity purification followed by mass spectrometry in accordance with some embodiments. Thirty-one proteins showed significant changes in phosphorylation levels between the lines (P-value≤0.01; see TABLE 9 below). The integrative analysis of disease features with phosphoproteomics provided a more comprehensive picture of disease-associated pathways and components. The networks obtained by analyzing lipidomics and proteomics separately had little overlap. By contrast, multi-omic analysis not only inferred the majority of hidden components obtained from the analysis of lipidomics and phosphoproteomics individually, but it also revealed new disease-associated molecules. These results emphasize that each type of molecular data resulted in identification of limited and distinct biological processes.

Figure 32:
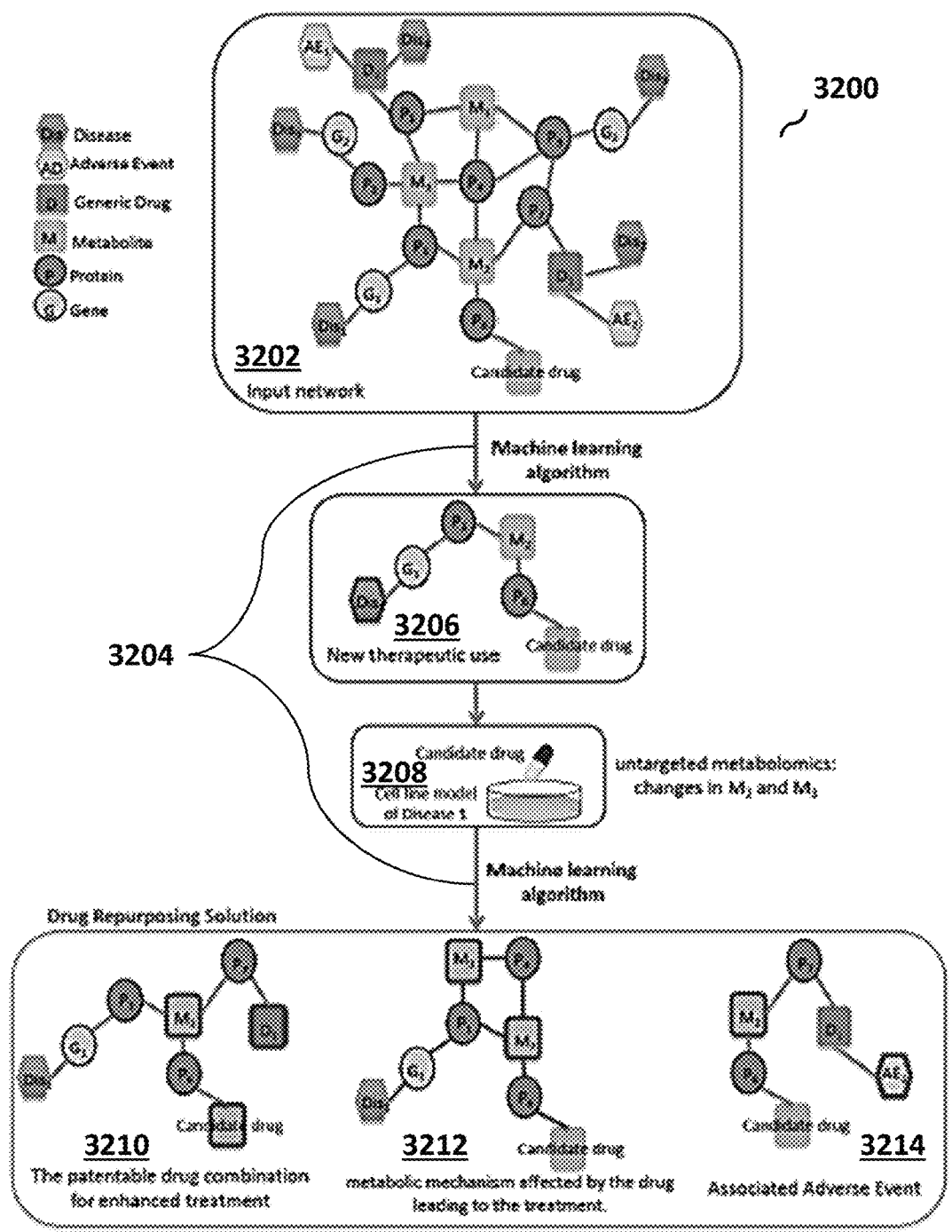
FIG. 32 is a flow diagram illustrating application of a machine-learning algorithm to a network to provide a drug repurposing solution in accordance with some embodiments.

FIG. 32 is a flow diagram illustrating application of a machine-learning algorithm to a network to provide a drug repurposing solution in accordance with some embodiments.

CONCLUSION

PIUMet is a network-based algorithm for integrative analysis of untargeted metabolomic data. Even with high-mass-accuracy instruments, most features detected in untargeted metabolomic experiments cannot be identified uniquely, and typically only a few are characterized unambiguously via additional time-consuming and costly MS/MS experiments. PIUMet leverages known metabolic reactions and protein-protein interactions to analyze the ambiguous assignment of metabolomics features. It can be used to identify dysregulated metabolic networks containing metabolites that are possible matches to the metabolomic features, and determine the robustness and disease-specificity of the results.

PIUMet is a general approach. Although its utility has been demonstrated by analyzing data for HD, the algorithm was not tailored to HD in any way. In fact, metabolomics changes in HD are studied relatively poorly compared to many other diseases such as diabetes, and even cancer. Therefore, PIUMet algorithms are expected to be equally effective in identifying altered pathways using untargeted metabolomics from any disease, or any comparison of two biological states.

Untargeted metabolomics has an important role in understanding disease, because targeted metabolomic profiling captures few of the relevant metabolites. Only eight of 296 metabolites assigned to disease features in the data were detected with a targeted metabolomic platform, reflecting the bias of targeted platforms toward well-studied metabolites. As a result, methods such as PIUMet for analyzing untargeted metabolomics have great potential to systematically discover new molecular mechanisms.

PIUMet does not replace MS/MS for identifying metabolite peaks, but it prioritizes metabolite features for experimental validation, and provides the protein and small molecule context of these features. Considering the costs and time associated with performing these experiments6, PIUMet could make a considerable impact in current metabolomic studies.

PIUMet algorithms fill an important need by translating untargeted metabolomic data into relevant biological knowledge and contextualizing metabolomics with other system-level molecular data. This integrative approach may be crucial for understanding a complete picture of disease-associated processes. Although the integrative analysis of untargeted metabolomics was established with proteomics data, PIUMet can be also applied to analyze metabolomics in conjunction with genomic data, and further extended to include transcriptional data. Therefore, a multi-omic, integrative approach in accordance with some embodiments is likely to be of even greater use as more data are generated.

Integrative analysis of metabolomic data in a disease provides information about dysregulated signaling pathways that can be targeted for therapeutic approaches. According to some embodiments described above, a new systems biology approach may overcome barriers in translating metabolomic data to relevant biological contexts and understanding the biological mechanisms altering metabolites. For example, network-based algorithms may be used to identify disease modifying pathways and key components linking the dysregulation of metabolomics to other classes of molecules. An inferred network shows pathways that connect experimentally identified dysregulated molecules via protein and metabolites there were not originally detected by the experiments. These molecules are linked via highly probable network of protein-protein and protein-metabolite interactions. In some embodiments, the integration of metabolomics with other 'omics may result in inferring the comprehensive picture of dysregulated pathways in cells that can be targeted for therapeutic purposes.

The performance of a PIUMet algorithm has been established in accordance with some embodiments, for example, in identification of dysregulated pathways in STHdh cell line model of Huntington's disease. The application of the algorithm in analysis of untargeted lipid data measured resulted in the identifying sphingolipid pathways dysregulation. Sphingosine-1-phosphate (S1P) key metabolites were identified in pathways that were not originally detected through experiments, and S1P level was shown to be significantly downregulated, contributing to disease pathogenesis, in which treating cells with FTY720-P, an analogue of S1P, has neuroprotective effects. In some embodiments, integrative analysis of untargeted metabolomic data with other-omic data is performed using PIUMet by inferring dysregulated pathways linking the changes in lipids to changes in phospho-proteins in STHdh cells. The integrative analysis of 'omic data was demonstrated to lead to identification of novel dysregulated components of the disease signaling pathways that cannot be distinguished by individual analysis of each 'omic data.

Thus, at least some embodiments facilitate inferring dysregulated pathways and their key components causing these alterations by integrative analysis of differential metabolite features in a disease with other 'omic data such as proteomics. At least some embodiments may be used to select metabolite features for further experimental validation and identification of therapeutics.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways.

For example, embodiments disclosed herein may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All publications, patent applications, patents, and other references mentioned herein are incorporated by reference in their entirety. In particular, the following sources are incorporated herein by reference in their entirety:

1. Alfarano et al., "The Biomolecular Interaction Network Database and Related Tools 2005 Update," *Nucleic Acids Res.* 33(Database issue):D418-424 (2005).
2. Aranda et al., "PSICQUIC and PSISCORE: Accessing and Scoring Molecular Interactions," *Nat. Methods* 8:528-529 (2011).
3. Babnigg et al., "A Database of Unique Protein Sequence Identifiers for Proteome Studies," *Proteomics* 6(16):4514-4522 (2006).
4. Bader et al., "BIND: The Biomolecular Interaction Network Database," *Nucleic Acids Res.* 31(1):248-250 (2003).
5. Bailly-Bechet et al., "Inference of Sparse Combinatorial-Control Networks from Gene-Expression Data: A Message Passing Approach," *BMC Bioinformatics* 11:355 (2010).
6. Baker et al., "Metabolomics: From Small Molecules to Big Ideas," *Nat. Methods* 8:117-121 (2011).
7. Block et al., "Altered Cholesterol and Fatty Acid Metabolism in Huntington Disease," *J. Clin. Lipidol.* 4:17-23 (2010).
8. Bornstein et al., "LibSBML: An API Library for SBML," *Bioinformatics* 24:880-881 (2008).
9. Brown, "Jurisica I: Online Predicted Human Interaction Database," *Bioinformatics* 21(9):2076-2082 (2005).
10. Chatraryamontri et al., "MINT: The Molecular INTeraction Database," *Nucleic Acids Res.* 35(Database issue):D572-574 (2007).
11. Cho et al., "After the Feature Presentation: Technologies Bridging Untargeted Metabolomics and Biology," *Curr. Opin. Biotechnol.* 28:143-48 (2014).
12. DeBerardinis et al., "Cellular Metabolism and Disease: What Do Metabolic Outliers Teach Us?" *Cell* 148:1132-44 (2012).
13. Deogracias et al., "Fingolimod, a Sphingosine-1 Phosphate Receptor Modulator, Increases BDNF Levels and Improves Symptoms of a Mouse Model of Rett Syndrome," *Proc. Natl. Acad. Sci.* 109:14230-35 (2012).
14. Di Menna et al., "Fingolimod Protects Cultured Cortical Neurons Against Excitotoxic Death," *Pharmacol. Res.* 67:1-9 (2013).
15. Di Pardo et al., "FTY720 (Fingolimod) Is a Neuroprotective and Disease Modifying Agent in Cellular and Mouse Models of Huntington Disease," *Hum. Mol. Genet.* 23:2251-65 (2014).
16. Dunn et al., "Mass Appeal: Metabolite Identification in Mass Spectrometry-Focused Untargeted Metabolomics," *Metabolomics* 9:44-66 (2013).
17. Frolkis et al., "SMPDB: The Small Molecule Pathway Database," *Nucleic Acids Res.* 38, D480-D487 (2010).
18. Gnad et al., "*PHOSIDA* 2011: The Posttranslational Modification Database," *Nucleic Acids Res.* 39:D253-60 (2011).

19. Grapov et al., "MetaMapR: Pathway Independent Metabolomic Network Analysis Incorporating Unknowns," *Bioinformatics* 31:2757-60 (2015).
20. Guldener et al., "MPact: The MIPS Protein Interaction Resource on Yeast," *Nucleic Acids Res.* 34(Database issue):D436-441 (2006).
21. Hermjakob et al., "IntAct: An Open Source Molecular Interaction Database," *Nucleic Acids Res.* 32(Database issue):D452-455 (2004).
22. Huang et al., "Integrating Proteomic, Transcriptional, and Interactome Data Reveals Hidden Components of Signaling and Regulatory Networks," *Sci. Signaling* 2:81 (Jul. 28, 2009), available at sciencesignaling.org (ra40).
23. Huang et al., "Linking Proteomic and Transcriptional Data Through the Interactome and Epigenome Reveals a Map of Oncogene-Induced Signaling," *PLoS Comput. Biol.* 9:2 (February 2013), available at ploscompbiol.org (e1002887).
24. Huang et al., "Systematic and Integrative Analysis of Large Gene Lists Using DAVID Bioinformatics Resources," *Nat. Protocol* 4:44-57 (2009).
25. Hucka et al., "SBML Forum. The Systems Biology Markup Language (SBML): A Medium for Representation and Exchange of Biochemical Network Models," *Bioinformatics* 19:524-31 (2003).
26. Johnson et al., "Bioinformatics: The Next Frontier of Metabolomics," *Anal. Chem.* 87:147-156 (2015).
27. Karnovsky et al., "Metscape 2 Bioinformatics Tool for the Analysis and Visualization of Metabolomics and Gene Expression Data," *Bioinformatics* 28:373-80 (2012).
28. Kerrien et al., "IntAct—Open Source Resource for Molecular Interaction Data," *Nucleic Acids Res.* 35(Database issue):D561-565 (2007).
29. Khurana et al., "Genome-Scale Networks Link Diverse Neurodegenerative Disease Genes to Alpha-Synuclein Through Distinct Cellular Pathologies" (unpublished) (on file with Applicant).
30. Kreilaus et al., "Brain Cholesterol Synthesis and Metabolism Is Progressively Disturbed in the R6/1 Mouse Model of Huntington's Disease: A Targeted GC-MS/MS Sterol Analysis," *J. Huntingtons Dis.* 4:305-18 (2015).
31. Krumsiek et al., "Mining the Unknown: A Systems Approach to Metabolite Identification Combining Genetic and Metabolic Information," *PLoS Genet.* 8, e1003005 (2012).
32. Kuo et al., "3Omics: A Web-Based Systems Biology Tool for Analysis,
Integration and Visualization of Human Transcriptomic, Proteomic and Metabolomic Data," *BMC Syst. Biol.* 7:64 (2013).
33. Li et al., "Huntingtin-Protein Interactions and the Pathogenesis of Huntington's Disease," *Trends Genet.* 20:146-54 (2004).
34. Li et al., "Predicting Network Activity from High Throughput Metabolomics," *PLoS Comput. Biol.* 9 (2013), available at ploscompbiol.org (e1003123).
35. López et al., "Brain Lipogenesis and Regulation of Energy Metabolism," *Curr. Opin. Clin. Nutr. Metab. Care* 11:483-90 (2008).
36. Maceyka et al., "Sphingosine-1-phosphate Signaling and Its Role in Disease," *Trends Cell Biol.* 22:50-60 (2012).
37. Mishra et al., "Human Protein Reference Database—2006 Update," *Nucleic Acids Res.* 34(Database issue):D411-414 (2006).
38. NCBI Resource Coordinators, "Database Resources of the National Center for Biotechnology Information," *Nucleic Acids Res.* 41:D8-D20 (2013).
39. Ng et al., "Extensive Changes in DNA Methylation Are Associated with Expression of Mutant Huntingtin," *Proc. Natl. Acad. Sci.* 110:2354-59 (2013).
40. Pagel et al., "The MIPS Mammalian Protein-Protein Interaction Database," *Bioinformatics* 21(6):832-834 (2005).
41. Patti et al., "Innovation: Metabolomics: The Apogee of the Omics Trilogy," *Nat. Rev. Mol. Cell Biol.* 13:263-69 (2012).
42. Peri et al., "Development of Human Protein Reference Database as an Initial Platform for Approaching Systems Biology in Humans," *Genome Res.* 13(10):2363-2371 (2003).
43. Puri et al., "Ethyl-EPA in Huntington Disease: A Double-Blind, Randomized, Placebo-Controlled Trial," *Neurol.* 65:286-92 (2005).
44. Puri et al., "Reduction in Cerebral Atrophy Associated with Ethyl-eicosapentaenoic Acid Treatment in Patients with Huntington's Disease," *J. Int. Med. Res.* 36:896-905 (2008).
45. Razick et al., "iRefIndex: A Consolidated Protein Interaction Database with Provenance," *BMC Bioinformatics* 9(1):405 (2008).
46. Ruepp et al., "CORUM: The Comprehensive Resource of Mammalian Protein Complexes," *Nucleic Acids Res.* 36(Database issue):D (Jan. 1, 2008).
47. Saghatelian et al., "Assignment of Endogenous Substrates to Enzymes by Global Metabolite Profiling," *Biochem.* 43:14332-39 (2004).
48. Salwinski et al., "The Database of Interacting Proteins: 2004 Update," *Nucleic Acids Res.* 32(Database issue): D449-451 (2004).
49. Schreiber et al., "Rapid Detection of Octamer Binding Proteins with 'Mini-Extracts,' Prepared from a Small Number of Cells," *Nucleic Acids Res.* 17:6419 (1989).
50. Stark et al., "BioGRID: A General Repository for Interaction Datasets," *Nucleic Acids Res.* 34(Database issue):D535-539 (2006).
51. Stevnsner et al., "The Role of Cockayne Syndrome Group B (CSB) Protein in Base Excision Repair and Aging," *Mech. Ageing Dev.* 129:441-48 (2008).
52. Subba Rao, "Mechanisms of Disease: DNA Repair Defects and Neurological Disease," *Nat. Clin. Pract. Neurol.* 3:162-72 (2007).
53. Tautenhahn et al., "XCMS Online: A Web-Based Platform to Process Untargeted Metabolomic Data," *Anal. Chem.* 84:5035-39 (2012).
54. Thiele et al., "A Community-Driven Global Reconstruction of Human Metabolism," *Nat. Biotechnol.* 31:419-25 (2013).
55. Trettel et al., "Dominant Phenotypes Produced by the Huntington's Disease Mutation in STHdh(Q111) Striatal Cells," *Hum. Mol. Genet.* 9:2799-809 (2000).
56. Tuncbag et al., "Simultaneous Reconstruction of Multiple Signaling Pathways Via the Prize-Collecting Steiner Forest Problem," *J. Comput. Biol.* 20:124-36 (2013).
57. U.S. Pat. No. 8,612,160, entitled "Identifying Biological Response Pathways," filed as U.S. patent application Ser. No. 12/618,915 on Nov. 16, 2009, and issued on Dec. 17, 2013;
58. Valenza et al., "Emerging Roles for Cholesterol in Huntington's Disease," *Trends Neurosci.* 34:474-86 (2011).
59. Wishart et al., "HMDB 3.0—The Human Metabolome Database in 2013," *Nucleic Acids Res.* 41(D1):D801-7 (January 2013).

60. Yeger-Lotem, et al., "Bridging High-Throughput Genetic and Transcriptional Data Reveals Cellular Responses to Alpha-Synuclein Toxicity," *Nat. Genet.* 41:316-23 (2009).

61. Yehuda et al., "Essential Fatty Acids and the Brain: From Infancy to Aging," *Neurobiol. Aging* 26(Suppl. 1):98-102 (2005).

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A method for unbiasedly identifying at least one of a metabolic pathway altered in a disease model and a protein that alters a level of a metabolite feature in a disease model, the method comprising:
   A) obtaining a protein-protein-metabolite interactome (PPMI) network, the PPMI network including a graph with a first set of nodes, a second set of nodes, and a plurality of edges, each node of the first set of nodes representing a metabolite, each node of the second set of nodes representing a protein, and each edge of the plurality of edges connecting two nodes representing a known interaction between at least one of:
      a metabolite represented by a first node of the first set of nodes and a protein represented by a first node of the second set of nodes; and
      two proteins respectively represented by two nodes of the second set of nodes;
   B) identifying a difference between a first level of the metabolite feature acquired from a disease sample and a second level of the metabolite feature acquired from a control sample based at least in part on liquid chromatography and mass spectrometry;
   C) adding a sample node to the PPMI network, the sample node representing an unknown metabolite associated with the diseased sample having the first level of the metabolite feature;
   D) connecting the sample node representing the unknown metabolite with an edge to each node representing a known metabolite having a level of the metabolite feature that is within a predetermined range that includes the first level of the metabolite feature;
   E) assigning a penalty to each node in the PPMI network with a number of edges above a threshold so as to remove bias, each penalty being associated with at least one of:
      a degree of the second set of nodes; and
      a square degree of the first set of nodes;
   F) generating a recurrence score for each node and each edge in the PPMI network by applying a prize-collecting Steiner forest (PCSF) algorithm modified by adding random noise to each edge weight to the PPMI network;
   G) generating a family of solutions to the modified PCSF algorithm to infer a complex topology of metabolic interactions; and
   H) performing background corrections for the family of solutions to calculate a significance of each solution so as to identify at least one of the altered metabolic pathway altered in the disease model and the protein that alters the level of the metabolite feature in the disease model.

2. The method of claim 1, the obtaining the PPMI network at step (A) further including generating the PPMI network based on a weighted bipartite graph of known protein-protein interactions and known protein-metabolite interactions.

3. The method of claim 1, wherein at least one node of the each node at step (E) includes a highly connected node, the removing the bias of the each node at step (E) further including eliminating the bias of the highly connected node.

4. The method of claim 1, the inferring the complex topology at step (G) further including identifying a subset of nodes from the first set of nodes and the second set of nodes, and identifying a subset of edges from the plurality of edges, having a minimum aggregate cost.

5. The method of claim 4, the identifying the subset of nodes further including:
identifying a source node representing a source of flow;
identifying a destination node representing a destination of flow; and
associating a quantity of flow with the source of flow.

6. The method of claim 5, wherein the identified subset of nodes minimizes an aggregate cost of an objective function, the objective function based on the quantity of flow between the source node and the destination node.

7. The method of claim 1, the identifying the altered metabolic pathway at step (H) further including identifying a minimum cost pathway having a minimum aggregate cost as the altered metabolic pathway.

8. The method of claim 7, the identifying the minimum cost pathway further including:
identifying a source node representing a source of flow;
identifying a destination node representing a destination of flow; and
associating a quantity of flow with the source of flow.

9. The method of claim 1, wherein in (E), the penalty of a node is associated with an anticipated performance of a molecule associated with that node during a signaling event.

10. The method of claim 1, further comprising assigning a penalty to each edge in the PPMI network, the penalty of the each edge associated with a reliability of an interaction between molecules connected by that edge.

11. A system for unbiasedly identifying at least one of a metabolic pathway altered in a disease model and a protein that alters a level of a metabolite feature in a disease model, the system comprising:
at least one communication interface;
at least one memory device for storing processor-executable instructions; and
at least one processor communicatively coupled to the at least one communication interface and the at least one memory device, wherein upon executing the processor-executable instructions, the at least one processor:
A) obtains a protein-protein-metabolite interactome (PPMI) network, the PPMI network including a graph with a first set of nodes, a second set of nodes, and a plurality of edges, each node of the first set of nodes representing a metabolite, each node of the second set of nodes representing a protein, and each edge of the plurality of edges connecting two nodes representing a known interaction between at least one of:
a metabolite represented by a first node of the first set of nodes and a protein represented by a first node of the second set of nodes; and
two proteins respectively represented by two nodes of the second set of nodes;
B) identifies a difference between a first level of the metabolite feature acquired from a disease sample and a second level of the metabolite feature acquired from a control sample based at least in part on liquid chromatography and mass spectrometry;
C) adds a sample node to the PPMI network, the sample node representing an unknown metabolite associated with the diseased sample having the first level of the metabolite feature;
D) connects the sample node representing the unknown metabolite with an edge to each node representing a known metabolite having a level of the metabolite feature that is within a predetermined range that includes the first level of the metabolite feature;
E) assigns a penalty to each node in the PPMI network with a number of edges above a threshold so as to remove bias, each penalty being associated with at least one of:
a degree of the second set of nodes; and
a square degree of the first set of nodes;
F) generates a recurrence score for each node and each edge in the PPMI network by applying a prize-collecting Steiner forest (PCSF) algorithm modified by adding random noise to each edge weight to the PPMI network;
G) generates a family of solutions to the modified PCSF algorithm to infer a complex topology of metabolic interactions; and
H) performs background corrections for the family of solutions to calculate a significance of each solution so as to identify at least one of the altered metabolic pathway altered in the disease model and the protein that alters the level of the metabolite feature in the disease model.

12. The system of claim 11, wherein the processor infers the complex topology at step (G) by identifying a subset of nodes from the first set of nodes and the second set of nodes, and identifying a subset of edges from the plurality of edges, having a minimum aggregate cost.

13. The system of claim 12, wherein the processor identifies the subset of nodes by:
identifying a source node representing a source of flow;
identifying a destination node representing a destination of flow; and
associating a quantity of flow with the source of flow.

14. The method of claim 13, wherein the identified subset of nodes minimizes an aggregate cost of an objective function, the objective function based on the quantity of flow between the source node and the destination node.

* * * * *